(12) United States Patent
Song et al.

(10) Patent No.: US 8,586,020 B2
(45) Date of Patent: *Nov. 19, 2013

(54) POLY(ORGANOPHOSPHAZENE) COMPOSITION FOR BIOMATERIALS

(75) Inventors: Soo-Chang Song, Seoul (KR); Thrimoorthy Potta, Seoul (KR); Mi-Ran Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 43 days.

This patent is subject to a terminal disclaimer.

(21) Appl. No.: 13/173,783

(22) Filed: Jun. 30, 2011

(65) Prior Publication Data

US 2013/0004455 A1 Jan. 3, 2013

(51) Int. Cl.
*A61K 31/74* (2006.01)
*C12N 9/96* (2006.01)
*C08G 69/48* (2006.01)
*C08G 63/91* (2006.01)
*A61K 47/48* (2006.01)

(52) U.S. Cl.
USPC ....... 424/78.17; 435/188; 525/421; 525/54.1; 525/54.2

(58) Field of Classification Search
USPC ............... 424/78.17; 435/188; 525/421, 54.1, 525/54.2
See application file for complete search history.

(56) References Cited

U.S. PATENT DOCUMENTS

2010/0297155 A1* 11/2010 Song et al. ................. 424/184.1

FOREIGN PATENT DOCUMENTS

WO   WO 2008/153277 A1 * 12/2008

* cited by examiner

Primary Examiner — Blessing M Fubara
(74) Attorney, Agent, or Firm — Staas & Halsey LLP

(57) ABSTRACT

Provided are a use of chemically-crosslinkable, poly(organophosphazene)s for biomaterials, chemically-crosslinkable poly(organophosphazene)s with a physiologically active substance covalently-bonded thereto, a use thereof for biomaterials, and a process for preparing the same. The chemical crosslinkings can be made by UV irradiation, and/or a crosslinker, and/or an additive, and/or an enzyme, and/or a mixing of at least one polymer.

3 Claims, 12 Drawing Sheets

Example 22

Example 22 + Vinyl sulfone crosslinker

Example 22 + Polyethyleneglycol vinylsulfone crosslinker

POLY(ORGANOPHOSPHAZENE) COMPOSITION FOR BIOMATERIALS

BACKGROUND OF THE INVENTION (a) Field of the Invention

The present invention relates to a use of chemically-crosslinkable, poly(organophosphazene)s for biomaterials, chemically-crosslinkable, poly(organophosphazene)s with a physiologically active substance covalently-bonded thereto, a use thereof for biomaterials, and a process for preparing the same.

(b) Description of the Related Art

In chemically-crosslinked polymer hydrogels, chemical crosslinkings are either generated from a polymerization in a polymer set off by UV irradiation or produced from Michael-Addition between thiols and acrylate, acrylamide or vinyl sulfone group or from an enzyme, developing a network structure to change an aqueous polymer solution into a gel. (see, Biomaterials 29, 2153 (2008), Biomacromolecules 4, 713 (2003)). However, the chemically-crosslinked polymer hydrogels have limitations in their use for injectionable biomaterials since during their preparation, their gelation behavior and physical properties of the resulting gel are not easy to control and the formation of the gel requires a lot of time. (see, Biomaterials 24, 11 (2003), Biomaterials 26, 4495 (2005)).

In case of thermosensitive polymer hydrogels, the aqueous polymer solution maintains its liquid phase at a low temperature, but it changes into a gel with a increasing temperature. Such sol-gel behavior can be observed in a reversible manner. The thermosensitive polymer hydrogels can be simply injected into a required site without needing to perform a surgical operation and quickly form a gel of three dimensional structure at a body temperature, which makes their chance strong to be used for the injectionable biomaterials such as a delivery system for a physiologically active substance including drugs. (see, Nature, 388, 860 (1997), U.S. Pat. No. 6,201,072).

The present inventors have already reported as follows: poly(organophosphazene)s obtained by making a substitution on dichloro phosphazene linear polymers with amino acid esters and methoxy polyethylene glycols have the characteristics of the thermosensitive polymer with sol-gel behavior, being in an aqueous solution state below a certain temperature while turning into a three-dimensional gel above the certain temperature. Moreover, such thermosensitive poly(organophosphazene)s are slowly hydrolyzed in an aqueous solution. (see, Macromolecules 32, 2188 (1999), Macromolecules 32, 7820 (1999), Macromolecules 35, 3876 (2002), Korean Patent Nos. 259,367, and 315,630, U.S. Pat. No. 6,319,984).

However, these thermosensitive polymer hydrogels fail to have a sufficiently high level of solidity. This have limited their application in the biomaterials that are required to have satisfactory gel solidity, such as materials for plastic surgery and orthopedics including a filler, tissue engineering biomaterials including artificial cartilage, dental materials, materials for preventing stenosis including stent, adhesion barriers, and vasoocclusion materials. In addition, it takes a lot of time for these thermosensitive polymer hydrogels to form a gel after injection, which limit their use for injectionable biomaterials. Therefore, in order to make an improvement with respect to the foregoing problems, it is demanded to develop a biodegradable, thermosensitive poly(organophosphazene) with crosslinkings, the polymer not only exhibiting sol-gel behavior with a change in a temperature, but also being able to form crosslinkings, and possessing a higher level of gel solidity and controllable pore sizes.

SUMMARY OF THE INVENTION

The present inventors have found that when chemically-crosslinkable, poly(organophosphazene)s with biodegradability and thermosensitivity are chemically crosslinked, their gel solidity is superior to the one without chemical crosslinkings and the resulting polymers are very useful for biomaterials, to complete the present invention.

Therefore, an embodiment of the present invention provides poly(organophosphazene)s (phosphazene polymers) with a physiologically active substance covalently-bonded thereto as represented by a structure of Chemical Formula 1, which is chemically-crosslinkable by UV irradiation and/or addition of a crosslinker, and/or addition of an additive, and/or addition of an enzyme, and/or mixing with other chemically-crosslinkable poly(organophosphazene)s, a process for preparing the same, and their use for various biomaterials.

Other embodiment provides hydrogels possessing excellent strength and exhibiting sol-gel behavior in a body wherein the poly(organophosphazene)s with a physiologically active substance covalently-bonded thereto are included at a certain concentration and chemical crosslinkings are formed within or between the poly(organophosphazene)(s) by UV irradiation and/or addition of a crosslinker, and/or addition of an additive, and/or addition of an enzyme, and/or mixing with other chemically-crosslinkable poly(organophosphazene)s, a process for preparing the same, and their use for various biomaterials.

Another embodiment provides a use for biomaterials of chemically-crosslinkable poly(organophosphazene)s or hydrogels comprising the same at a certain concentration wherein chemical crosslinkings within or between the poly(organophosphazene)(s) are formed by UV irradiation and/or addition of a crosslinker, and/or addition of an additive, and/or addition of an enzyme, and/or mixing with other chemically-crosslinkable poly(organophosphazene)s.

Still other embodiment provides a method of forming chemical crosslinkings within or between the polymer(s) by treating chemically-crosslinkable poly(organophosphazene)s with at least one of the additives selected from the group consisting of a pH regulator, a catalyst, and an organic solvent, and a hydrogel comprising the chemically-crosslinked, poly(organophosphazene)s thus obtained.

DETAILED DESCRIPTION OF THE EMBODIMENT

The crosslinkable poly(organophosphazene)s of the present invention not only exhibit sol-gel behavior by chemical crosslinkings but also have thermosensitivity as their sol-gel behavior varies with a temperature. Therefore, after easily forming a gel by a temperature change, they can be chemically-crosslinked by UV irradiation and/or addition of a crosslinker, and/or addition of an additive, and/or addition of an enzyme, and/or mixing with the poly(organophosphazene)s to form a gel with a higher level of gel solidity. As a result, they can be utilized not only as delivery materials for a physiologically active substance such as drugs but also as biomaterials that are required to have a sufficiently high level of gel solidity, such as materials for plastic surgery and orthopedics including a filler, tissue engineering biomaterials including artificial cartilage, dental materials, stenosis preventing materials including stent, adhesion barriers, vasoocclusion materials, and the like.

Due to their loose network structure, conventional thermosensitive polymers showing sol-gel behavior have a low level of gel solidity and thus their applications as biomaterials have been limited. In contrast, after being gelled by a temperature, the poly(organophosphazene)s according to the present invention are chemically-crosslinked to constitute a denser network between the polymers, and the methods and the degree of crosslinking can be extensively controlled depending on their applications. Therefore, they can deliver a wider range of drugs when being used as a delivery system for physiologically active substances and the polymers have an increased hardness so that they also can be utilized as biomaterials that are required to have a sufficiently high level of gel solidity such as materials for plastic surgery and orthopedics including a filler, tissue engineering biomaterials including artificial cartilage, dental materials, stenosis preventing materials including stent, adhesion barriers, vasoocclusion materials, and the like. In addition, besides the high level of gel strength, since one can directly bond a physiologically-active and functional substance as necessary depending on the types of a desired biomaterial to the polymers, they can be used as various biomaterials, having a wide range of applicability and functionality and excellent biocompatibility.

First, an embodiment of the present invention provides at least one poly(organophosphazene) of Chemical Formula 1 that is chemically-crosslinkable and has a physiologically active substance covalently-bonded thereto, and a chemically-crosslinkable poly(organophosphazene) of Chemical Formula 1 wherein g, h, and i are 0.

The physiologically active substances can be any of physiologically active substances having at least one functional group selected from the group consisting of a hydroxyl, an amide, an amino, a carboxyl, a thiol, a vinyl, an aldehyde, a halogen, and a ketone groups and being capable of forming a covalent bond. For example, they are at least one selected from the group consisting of a protein, a polypeptide, a peptide, an antibody, a hormone, a vaccine, a gene, an anti-cancer drug, an angiogenesis inhibitor, and the like having at least one functional group selected from the group consisting of a hydroxyl, an amide, an amino, a carboxyl, a thiol, a vinyl, an aldehyde, a halogen, and a ketone groups. The physiologically active substances are characterized in that they are bonded to the poly(organophosphazene) through covalent bonds between the functional groups described above and the functional group of at least one of $R^6$, $R^9$ and $R^{10}$ of the poly(organophosphazene) selected from the group consisting of a hydroxyl, an amide, an amino, a carboxyl, a thiol, a vinyl groups and the like.

Other embodiment of the present invention provides a hydrogel containing a poly(organophosphazene) with a physiologically active substance covalently-bonded thereto, wherein the hydrogel comprises a solution of at least one chemically-crosslinkable, poly(organophosphazene) of Chemical Formula 1 with a physiologically active substance covalently-bonded thereto and/or at least one poly(organophosphazene) of Chemical Formula 1 in which g, h, and i are 0 (See, Chemical Formula 1-2), and chemical crosslinkings are formed within and/or between the poly(organophosphazene)(s) by UV irradiation and/or addition of a crosslinker, and/or addition of an additive, and/or addition of an enzyme, and/or mixing with other chemically-crosslinkable poly(organophosphazene)s, and wherein the hydrogel shows temperature-dependant sol-gel behavior and has excellent gel solidity.

Chemical Formula 1-1 comprises both of the poly(organophosphazene) of Chemical Formula 1 with a physiologically active substance covalently-bonded thereto and the poly(organophosphazene) of Chemical Formula 1 wherein g, h, and i are zero (0) (See, Chemical Formula 1-2).

[Chemical Formula 1]

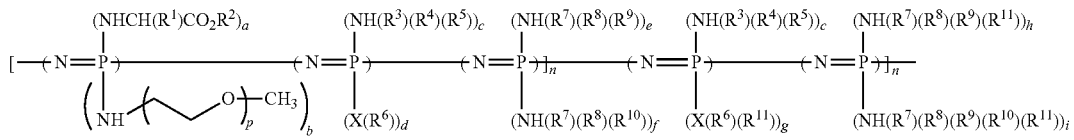

In the above formula, p represents the number of the repeating unit of ethylene glycol ranging from 7 to 50, $NHCH(R^1)CO_2R^2$ is a hydrophobic amino acid ester, wherein $R^1$ is selected from the group consisting of H, $CH_3$, $CH_2SH$, $CH_2OH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2H_2C_6H_4$, and $R^2$ is selected from the group consisting of $CH_3$, $C_2H_5$, $C_3H_7$, $C_4H_9$, $CH_2C_6H_5$ and $CH_2CHCH_2$, $NH(R^3)(R^4)(R^5)$ is an amino acid, a peptide, or a depsipeptide ester, wherein $R^3$ is $CH(W)$, $R^4$ is selected from the group consisting of $CO_2$, $CONHCH(Q)CO_2CO_2$, $CH_2CO_2$ and $CO_2CH(CH_3)CO_2$, $R^5$ is selected from the group consisting of H, $CH_3$ and $C_2H_5$, in which each of W and Q is independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $XR^6$ is a substituent having a thiol group or a vinyl group that can be crosslinked by UV irradiation, and/or addition of a crosslinker, and/or addition of an additive, and/or addition of an enzyme, and/or mixing with other chemically crosslinkable poly(organophosphazene)s, or a substituent having tyrosine, tyramine, or a phenyl derivative that can be crosslinked by an enzyme, wherein X represents N or O, and $R^6$ is a compound with a thiol or vinyl group, a compound with the thiol or vinyl group protected with a protecting group, or a compound with tyrosine, tyramine or a phenyl derivative, which is selected from the group consisting of an acrylate compound, a methacrylate compound, an acrylamide compound, a vinyl sulfone compound, a thiol compound, a cysteine compound, a cisteamine compound, a mercaptic acid compound, an allyl pyrimidine compound, and a compound having a thiol or vinyl group protected by a protecting group, or is selected from the group consisting of a tyramine compound, a tyrosine compound, and a phenol derivative, wherein the protecting group for the thiol group may be any one of an alkyl group, a benzyl group (e.g., p-methoxybenzyl, o- or p-hydroxyl or acetoxybenzyl, p-nitrobenzyl, 2,4,6-trimethylbenzyl, 2,4,6-trimethoxybenzyl, 4-pycoryl, 2-quinolinyl methyl, 2-pycoryl-N-oxydo, 9-anthryl methyl, 9-fluorenyl methyl, xanthenyl, p-ferrocenyl methyl), diphenylmethyl, triphenylmethyl thioether (e.g., diphenylmethyl, bis(4-methoxyphenyl)methyl, 5-dibenzosurberyl, triphenylmethyl, diphenyl-4-pyridylmethyl, phenyl, 2,3-dinitrophenyl, t-butyl, 1-adamantyl), a substituted methyl derivative (e.g., methoxymethyl, isobutoxymethyl, benzyloxymethyl, 2-tetrahydropyranyl, benzylthiomethyl, phenylthiomethyl, thiazolidine, acetamidomethyl, trimethylacetamidomethyl, benzamidomethyl, allyloxycarbonylamidomethyl, phenylacetamidomethyl, phthalimidomethyl, acetyl, carboxyl, cyanomethyl), an ethyl derivative (e.g., 2-nitro-1-phenylethyl, 2-(2,4-dinitrophenyl) ethyl, 2-(4'-pyridyl)-ethyl, 2-cyanoethyl, 2-(trimethylsilyl) ethyl, 2,2-bis(carboethoxy)ethyl, (1-m-nitrophenyl-2-benzoyl)ethyl, 2-phenylsulfonylethyl, 1-(4-methylphenylsulfonyl)-2-methylprop-2-yl), thioester group (e.g., acetyl, benzoyl, trifluoroacetyl, N-[[(p-biphenylyl)isopropoxy]carbonyl]-N-methyl-γ-aminothiobutyrate), thiocarbonate derivative 2,2,2-trichloroethoxycarbonyl, t-butoxycarbonyl, benzyloxycarbonyl, p-methoxybenzyloxycarbonyl), a thiocarbamate derivative (e.g., N-ethyl, N-methoxymethyl), a miscellaneous derivative, an asymmetric disulfide (e.g., ethyl, t-butyl substituted S-phenyl disulfide), and sulphenyl derivative (e.g., sulfonate, sulphenyl thiocarbonate, 3-nitro-2-pyridinesulphenyl sulfide, S4-tricarbonyl[1,2,3,4,5-η]-2,4-cyclohexadien-1-A-iron(1+), oxathiolone), and the protecting group of the vinyl group may be O-nitrophenyl selenoethyl.

$NH(R^7)(R^8)(R^9)$ is a substituent having a functional group, in which $R^7$ is $CH(Y)$, $R^8$ is selected from the group consisting of $CH_2$, $C_2H_4$, $C_3H_6$, $C_4H_8$, $CH_2C_6H_4$, $CH_2CO_2$, $CH_2OCOCH_2CH_2CO$, $CH_2OCOCH_2CH_2CH_2CO$, $CH_2OCOCH_2CH_2CH_2CH_2CO$, $CH_2CH_2OCOCH_2CH_2CO$, $CH_2CH_2OCOCH_2CH_2CO$, $CH_2CH_2OCOCH_2CH_2CH_2CO$, O, CONHCH(Z)O, CONHCH(Z)CONHCH(M)O, CONHCH(Z)CONHCH(M) CONHCH(L)O, CO, $CO_2$, S, CONHCH(Z)S, CONHCH(Z) CONHCH(M)S, CONHCH(Z)CONHCH(M)CONHCH(L) S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)$CO_2$, COCHNH(Z) CONHCH(M)$CO_2$, COCHNH(Z)CONHCH(M)CONHCH(L)$CO_2$, $[OCH(CH_3)CO]_q$, $(OCH_2CO)_q$, $[(OCH(CH_3)CO]_q$, $[OCO(CH_2)_8CO]_q$, $[OCOC_6H_5O(CH_2)_3OC_6H_5CO]_q$ and $[OCOC_6H_5O(CH_2)_6OC_6H_5CO]_q$, and $R^9$ is selected from the group consisting of functional groups such as OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_qH$, $[NHCH(C_4H_8NH_2)CO]_qOH$, $[NHCH[(CH_2)_3C(=NH)(NH_2)]CO]_qOH$, folic acid, hyaluronic acid, cyclodextrin, an imidazole compound, histidine, lysine, arginine, cysteine, thioalkyl amine, spermine, spermidine, various molecular weights of polyethyleneimine, polyhistidine, polylysine, polyarginine, heparin, chitosan, and protamine, and a protecting group for a typical functional group, in which each of Y, Z, M, and L is independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2 CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$ and $CH_2SH$, and q represents the number of the repeating unit ranging from 1 to 18000, $NH(R^7)(R^8)(R^{10})$ is a substituent with a thiol group, a vinyl group, tyrosine, tyramine or a phenyl derivative triggering crosslinkings by UV irradiation and/or addition of a crosslinker, and/or addition of an enzyme, and/or addition of an additive, and/or mixing with other crosslinkable poly(organophosphazene)s, wherein $R^7$ and $R^8$ are the same as defined in the above substituent, $NH(R^7)(R^8)(R^9)$, and $R^{10}$ represents a compound capable of triggering crosslinkings by UV irradiation and/or addition of a crosslinker, and/or addition of an additive, and/or addition of an enzyme, and/or mixing with other crosslinkable poly(organophosphazene)s, which is selected from the same group as defined for $R^6$ and is the same as or different from $R^6$, $X(R^6)(R^{11})$ is a substituent chemically bonded to a physiologically active substance such as drugs, wherein X and $R^6$ are the same as defined in $X(R^6)$, and $R^{11}$ represents a physiologically active substance which is at least one selected from the group consisting of a protein, a polypeptide, a peptide, a fusion protein, an antibody, a hormone, a vaccine, a gene, an anticancer drug, and an angiogenesis inhibitor having various functional groups such as a hydroxyl, an amide, an amino, a carboxylic, a thiol, a vinyl, an aldehyde, a halogen and a ketone groups, $NH(R^7)(R^8)(R^9)(R^{11})$ is a substituent chemically bonded to the physiologically active substance such as drugs, wherein $R^7$, $R^8$, $R^9$, and $R^{11}$ are the same as defined above, $NH(R^7)(R^8)(R^{10})(R^{11})$ is a substituent chemically bonded to the physiologically active substance such as drugs, in which $R^7$, $R^8$, $R^{10}$, and $R^{11}$ are the same as defined above, a, b, c, d, e, f, g, h, and i represent a content of each substituent, in which a and b range from 0.01 to 1.9, respectively, c, d, e, f, g, h, and i range from 0 to 1.9, respectively, d and f cannot be simultaneously zero, and g, h, and i cannot be simultaneously zero, and a+b+c+d+e+f+g+h+i=2.0, and n represents a degree of polymerization of the poly(organophosphazene), ranging from 5 to 100000.

[Chemical Formula 1-1]

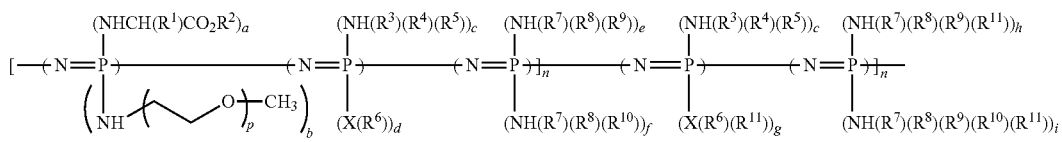

In the above Formula, a, b, c, d, e, f, g, h, and i represent a content of each substituent, in which a and b range from 0.01 to 1.9, respectively, c, d, e, f, g, h, and i range from 0 to 1.9, respectively, d and f cannot be simultaneously zero, and a+b+c+d+e+f+g+h+i=2.0, and besides the foregoing, the definitions for other substituents and symbols are the same as defined in Chemical Formula 1.

[Chemical Formula 1-2]

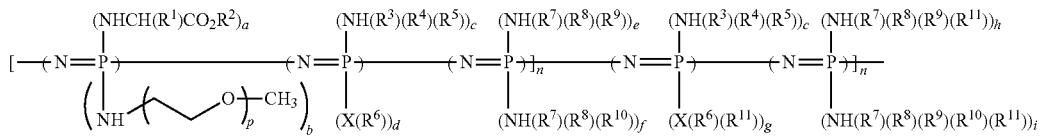

In the above Formula, a, b, c, d, e, f, g, h, and i represent a content of each substituent, in which a and b range from 0.01 to 1.9, respectively, c, d, e, f, g, h, and i range from 0 to 1.9, respectively, d and f cannot be simultaneously zero, g, h, and i are simultaneously zero, and a+b+c+d+e+f+g+h+i=2.0, and besides the foregoing, the definitions for other substituents and symbols are the same as defined in Chemical Formula 1.

As $R^9$, one can use any of folic acid, hyaluronic acid, cyclodextrin, an imidazole compound (dacarbazine, 1-(3-aminopropyl)imidazole, methyl histamine dihydrochloride, 4-(1H-imidazol-1-yl)aniline, histamine, imiquimod, biotin ethylenediamine, 2-(2-methylimidazolyl)ethylamine dihydrochloride, 5-amino-4-imidazolecarboxamide hydrochloride, 5-aminoimidazole-4-carboxamide, 4-imidazole acrylic acid, 4-imidazole carboxylic acid, 2-iminobiotin, L-(+)-ergothioneine, 4,5-imidazole dicarboxylic acid, 1-(2-hydroxyethyl)imidazole, 4(5)-(hydroxymethyl)imidazole, 4-imidazolemethanol hydrochloride, etanidazole, 4-(imidazol-1-yl) phenol), HMMNI (2-hydroxymethyl-1-methyl-5-nitro-1H-imidazole), 2-mercaptoimidazole, 1-(4-Hydroxybenzyl)imidazole-2-thiol, thiabendazole, 1,1'-thiocarbonyldiimidazole, 2-mercapto-1-methylimidazole, 2-mercaptoimidazole, methimazole, 1-(2,3,5,6-tetrafluorophenyl)imidazole, 1-(heptafluorobutyryl)imidazole, 1-(pentafluoropropionyl)imidazole, 1-(trifluoroacetyl)imidazole), 1-(trifluoromethanesulfonyl)imidazole), 1-[2-(trifluoromethyl)phenyl]imidazole, 2-bromo-1H-imidazole, 2-butyl-4-chloro-5-(hydroxymethyl)imidazole, 2-butyl-5-chloro-1H-imidazole-4-carboxaldehyde, 2-chloro-1H-imidazole, 4-(4-bromophenyl)-1H-imidazole, 4-(4-chlorophenyl)-1H-imidazole, 4-(4-fluorophenyl)-1H-imidazole, 5-bromo-1-methyl-1H-imidazole, 6-bromo-1H-benzimidazole, cyazofamid, imazalil, ketoconazole, fenobam, imazalil sulfate, losartan potassium, neurodazine, nutlin-3, SB 220025 trihydrochloride, SB 202190 (4-(4-fluorophenyl)-2-(4-hydroxyphenyl)-5-(4-pyridyl)-1H-imidazole), PD 169316 (4-(4-fluorophenyl)-2-(4-nitrophenyl)-5-(4-pyridyl)-1H-imidazole), SB 239063 (trans-1-(4-hydroxycyclohexyl)-4-(4-fluorophenyl)-5-(2-methoxypyrimidin-4-yl)imidazole), tioconazole, triflumizole, 2,4,5-tribromoimidazole, 5-chloro-1-methyl-4-nitroimidazole, 2-ethyl-4-methyl-1H-imidazole-1-propanenitrile, 4,5-dicyanoimidazole, 5-ethynyl-1-methyl-1H-imidazole, etc), histidine, lysine, arginine, cysteine, thioalkyl amine (for example C1 to C50), spermine, spermidine, TAT peptide, various molecular weights of polyethyleneimine, polyhistidine, polylysine, polyarginine, heparin, chitosan, and protamine with no limitation on the weight-average molecular weight. Preferably, the weight-average molecular weight thereof may ranges from 50 to 100,000, but the present invention is not limited thereto.

The protecting group for the typical functional group available for $R^9$ may be any of generally known protecting groups, and for example, it can be selected from the following Table 1.

TABLE 1

| Functional group | Protecting group (R'=$R^8$) |
|---|---|
| Carboxyl group (RCOOR') | Fluorenylmethyl ester, Methoxymethyl ester ($CH_2OCH_3$), Methylthiomethyl ester ($CH_2SCH_3$), Tetrahydrofuranyl ester, Methoxyethoxymethyl ester ($CH_2OCH_2CH_2OCH_3$), 2-(trimethylsilyl)ethoxymethyl ester ($CH_2OCH_2CH_2Si(CH_3)_3$), Benzyloxymethyl ester ($CH_2OCH_2C_6H_5$), Pivaloxyloxymethyl ester ($CH_2O_2CC(CH_3)_3$), Phenylacetoxymethyl ester ($CH_2O_2CCH_2Ph$), Triisopropylsilylmethyl ester ($CH_2Si$—i-$Pr_3$), Cyanomethyl ester ($CH_2CN$), Acetol ester ($CH_2COCH_3$), Phenacyl ester ($CH_2COC_6H_5$), p-Bromophenacyl ester ($CH_2COC_6H_4$—p-Br), α-Methylphenacyl ester ($CH(CH_3)COC_6H_5$). p-Methoxyphenacyl ester ($CH_2COC_6H_4$—p-$OCH_3$), Desyl ester, Carboxamidomethyl ester ($CH_2CONH_2$), p-Azobenzenecarboxamidomethyl ester ($CH_2(O)CNHC_6H_4N$=$NC_6H_5$), N-Phthalimidomethyl ester, 2,2,2-Trichloroethyl ester ($CH_2CCl_3$), 2-Haloethyl ester ($CH_2CH_2X$, X = I, Br, Cl), ω-Chloroalkyl ester (($CH_2)_nCl$, n = 4, 5), 2-(trimethylsilyl)ethyl ester ($CH_2CH_2Si(CH_3)_3$), 2-Methylthioethyl ester ($CH_2CH_2SCH_3$), 1,3-Dithianyl-2-methyl ester, 2-(p-Nitrophenylsulfenyl)ethyl ester ($CH_2CH_2SC_6H_4$—p-$NO_2$), 2-(p-Toluenesulfonyl)ethyl ester ($CH_2CH_2SO_2C_6H_4$—p-$CH_3$), 2-(2'-Pyridyl)ethyl ester ($CH_2CH_2$-2-$C_5H_4N$), 2-(p-Methoxyphenyl)ethyl ester ($CH_2CH_2C_6H_4O$—p-$CH_3$), 2-(diphenylphosphino)ethyl ester ($CH_2CH_2P(C_6H_5)_2$), 1-Methyl-1-phenylethyl ester ($C(CH_3)_2C_6H_5$), 2-(4-Acetyl-2-nitrophenyl)ethyl ester, 2-Cyanoethyl ester ($CH_2CH_2CHN$), t-Butyl ester ($C(CH_3)_3$), 3-Methyl-3-pentyl ester ($CCH_3(C_2H_4)_2$), Dicyclopropylmethyl ester, 2,4-Dimethyl-3-pentyl ester ($CH(i-Pr)_2$), Cyclopentyl ester (c-$C_5H_9$), Cyclohexyl ester (c-$C_6H_{11}$), Allyl ester ($CH_2CH$=$CH_2$), Methallyl ester ($CH_2(CH_3)C$=$CH_2$), 2-Methylbut-3-en-2-yl ester ($C(CH_3)_2CH$=$CH_2$), 3-Methylbut-2-enyl ester ($CH_2CH$=$C(CH_3)_2$), 3-Buten-1-yl ester ($CH_2CH_2CH$=$CH_2$), 4-(Trimethylsilyl)-2-buten-1-yl ester ($CH_2CH$=$CHCH_2Si(CH_3)_3$), Cinnamyl ester ($CH_2CH$=$CHC_6H_5$), α-Methylcinnamyl ester ($CH(CH_3)CH$=$CHC_6H_5$), Prop-2-ynyl ester ($CH_2C$≡$CH$), Phenyl ester ($C_6H_5$), 2,6-Dimethylphenyl ester, 2,6-Diisopropylphenyl ester, 2,6-Di-t-butyl-4-methylphenyl ester, 2,6-Di-t-Butyl-4-methoxyphenyl ester, p-(Methylthio)phenyl ester ($C_6H_4$—p-$SCH_3$), Pentafluorophenyl ester ($C_6F_5$), Benzyl ester ($CH_2C_6H_5$), Triphenylmethyl ester ($C(C_6H_5)_3$), Diphenylmethyl ester ($CH(C_6H_5)_2$) Bis(o-nitrophenyl)methyl ester ($CH(C_6H_4$—o-$NO_2)_2$), 9-Anthrylmethyl ester ($CH_2$-9-Anthryl), 2-(9,10-Dioxo)anthrylmethyl) ester, 5-dibenzosuberyl ester, 1-Pyrenylmethyl ester, 2-(trifluoroaceticmthyl)-6-chromonylmethyl ester, 2,4,6-Trimethylbenzyl ester ($CH_2C_6H_2$-2,4,6-$(CH_3)_3$), p-Bromobenzyl ester ($CH_2C_6H_4$—p-Br), o-Nitrobenzyl ester ($CH_2C_6H_4$—o-$NO_2$), p-Nitrobenzyl ester ($CH_2C_6H_4$—p-$NO_2$), p-Methoxybenzyl ester ($CH_2C_6H_4$—p-$OCH_3$), 2,6-Dimethoxybenzyl ester ($CH_2C_6H_3$-2,6-$(OCH_3)_2$), 4-(Methylsulfinyl)benzyl ester ($CH_2C_6H_4(O)S$-4-$CH_3$), 4-Sulfobenzyl ester ($CH_2C_6H_4SO_3^-Na^+$), 4-Azidomethoxybenzyl ester ($CH_2C_6H_4OCH_2N_3$), 4-{N-[1-(4,4-Dimethyl-2,6-dioxocyclohexylidene)-3-methlbutyl]amino}benzyl ester, Piperonyl ester, 4-Picolyl ester ($CH_2$-4-pyridyl), p-P-Benzayl ester ($CH_2C_6H_4$—p-P), Trimethylsilyl ester ($Si(CH_3)_3$), Triethylsilyl ester ($Si(C_2H_5)_3$), t-Butyldimethylsilyl ester ($Si(CH_3)_2C(CH_3)$, i-Propyldimethylsilyl ester ($Si(CH_3)_2CH(CH_3)_2$), Phenyldimethylsilyl ester ($Si(CH3)_2C_6H_5$), Di-t-butylmethylsilyl ester ($SiCH_3(t-Bu)_2$), Triisopropylsilyl ester |

TABLE 1-continued

| Functional group | Protecting group (R'=R$^8$) |
|---|---|
| Thiol group (RSR') | S-Alkyl thioether (C$_n$H$_{2n+1}$), S-Benzyl thioether (CH$_2$Ph), S-p-Methoxylbenzyl thioether (CH$_2$C6H4—p-OCH$_3$), S-o- or p-Hydroxy-or-Acetoxybenzyl thioether (CH$_2$C6H4-o-(or p-)-OR', R' = H or Ac), S-p-Nitrobenzyl thioether (CH$_2$C$_6$H$_4$—p-NO$_2$), S-2,4,6-Trimethylbenzyl thioether (CH$_2$C$_6$H$_2$-2,4,6-Me$_3$), S-2,4,6-Trimethoxybenzyl thioether (CH$_2$C$_6$H$_2$-2,4,6-(OMe)$_3$), S-4-Picolyl thioether (CH$_2$-4-pyridyl), S-2-Quinolinylmethyl thioether, S-2-Picolyl N-Oxide thioether (CH$_2$-2-pyridyl N-Oxide), S-9-Anthrylmethyl thioether (CH$_2$-9-anthtyl), S-9-Fluorenylmethyl thioether, S-Xanthenyl thioether, S-Ferrocenylmethyl thioether, S-Diphenylmethyl thioether (CH(C$_6$H$_5$)$_2$), S-Bis(4-methoxyphenyl)methyl thioether (CH(C$_6$H$_4$-4-OCH$_3$)$_2$), S-Bis(4-methoxyphenyl)phenylmethyl thioether, S-5-Dibenzosuberyl thioether, S-Triphenylmethyl thioether (C(C$_6$H$_5$)$_3$), S-Diphenyl-4-pyridylmethyl thioether (C(C$_6$H$_5$)$_2$-4-pyridyl), S-Phenyl thioether (C$_6$H$_5$), S-2,4-Dinitrophenyl thioether (C$_6$H$_3$-2,4-(NO$_2$)$_2$), S-t-Butyl thioether (C(CH$_3$)$_3$), S-1-Adamantyl thioether, S-Methoxymethyl monothioacetal (CH$_2$OCH$_3$), S-Isobutoxymethyl monothioacetal (CH$_2$OCH$_2$CH(CH$_3$)$_2$), S-Benzyloxymethyl monothioacetal (CH$_2$OBn), S-2-Tetrahydropyranyl monothioacetal, S-Benzylthiomethyl dithioacetal (CH$_2$SCH$_2$C$_6$H$_5$), S-Phenylthiomethyl dithioacetal (CH$_2$SC$_6$H$_5$), S-Acetamidomethyl thioacetal (CH$_2$NHCOCH$_3$), S-Trimethylacetamidomethyl thioacetal (CH$_2$NHCOC(CH$_3$)$_3$), S-Benzamidomethyl (thioacetalCH$_2$NHCOC$_6$H$_5$), S-Allyloxycarbonylaminomethyl thioacetal (CH$_2$NH(O)COCH$_2$CH=CH$_2$), S-Phenylacetamidomethyl thioacetal (CH$_2$NH(O)CCH$_2$C$_6$H$_5$), S-Phthalimidomethyl thioacetal,S-Acetyl, S-Carboxy, and S-Cyanomethyl thioether (CH$_2$X, X = —COCH$_3$, —CO$_2$H, —CN), S-(2-Nitro-1-phenyl)ethyl thioether (CH(C$_6$H$_5$)CH$_2$NO$_2$), S-2-(2,4-Dinitrophenyl)ethyl thioether, S-2-(4'-Pyridyl)ethyl thioether (CH$_2$CH$_2$NC$_4$H$_4$), S-2-Cyanoethyl thioether (CH$_2$CH$_2$CN), S-2-(Trimethylsilyl)ethyl thioether (CH$_2$CH$_2$TMS), S-2,2-Bis(carboethoxy)ethyl thioether (CH$_2$CH(COOC$_2$H$_5$)$_2$), S-(1-m-Nitrophenyl-2-benzoyl)ethyl thioether (CH(C$_6$H$_4$—m-NO$_2$)CH$_2$COC$_6$H$_5$), S-2-phenylsulfonylethyl thioether (CH$_2$CH$_2$SO$_2$Ph), S-1-(4-Methylphenylsulfonyl)-2-methyl-prop-2-yl thioether (C(CH$_3$)$_2$CH$_2$SO$_2$C$_6$H$_4$-4-CH$_3$), Triisopropylsilyl thioether, S-Acetyl derivatives (COCH$_3$), S-Benzoyl derivatives (COC$_6$H$_5$), S-Trifluoroaceticacetyl derivatives (COCF$_3$), S-2,2,2-Trichloroethoxycarbonyl derivatives (COOCH$_2$CCl$_3$), S-t-Butoxycarbonyl derivatives (COOC(CH$_3$)$_3$), S-Benzyloxycarbonyl derivatives (COOCH$_2$C$_6$H$_5$), S-p-Methoxybenzyloxycarbonyl derivatives (COOCH$_2$C$_6$H$_4$—p-OCH$_3$), S-(N-Ethyl-carbamate)(CONHC$_2$H$_5$), S-(N-Methoxymethylcarbamate) (CONHCH$_2$OCH$_3$), S-Ethyl disulfide (SC$_2$H$_5$), S-t-Butyl disulfide (SC(CH$_3$)$_3$) |
| Hydroxy group (ROR') | Methyl ether (CH$_3$), Methoxymethyl ether (CH$_2$OCH$_3$), Methylthiomethyl ether (CH$_2$SCH$_3$), (Phenyldimethylsilyl)methoxy-methyl ether (CH$_2$OCH$_2$Si(CH$_3$)$_2$C$_6$H$_5$), Benzyloxymethyl ether (CH$_2$OCH$_2$Ph), p-Methoxybenzyloxymethyl ether (CH$_2$OCH$_2$C$_6$H$_4$O—p-Me), p-Nitrobenzyloxymethyl ether (CH$_2$OCH$_2$C$_6$H$_4$-4-NO$_2$), o-Nitrobenzyloxymethyl ether (CH$_2$OCH$_2$C$_6$H$_4$-2-NO$_2$), (4-Methoxyphenoxy)methyl ether (CH$_2$OC$_6$H$_4$-4-OCH$_3$), Guaiacolmethyl ether (CH$_2$OC$_6$H$_4$-2-OMe), t-Butoxymethyl ether (CH$_2$O—t-Bu), 4-Pentenyloxy-methyl ether (CH$_2$OCH$_2$CH$_2$CH$_2$CH=CH$_2$), Siloxymethyl ether (CH$_2$OSiR'R'', R' = t-Bu, R'' = Me; R' = Thexyl, R'' = Me; R' = t-Bu, R'' = Ph), 2-Methoxyethoxymethyl ether (CH$_2$OCH$_2$CH$_2$OCH$_3$), 2,2,2-Trichloroethoxymethyl ether (CH$_2$OCH$_2$CCl$_3$), Bis(2-chloroethoxy)methyl ether (CH(OCH$_2$CH$_2$Cl)$_2$), 2-(Trimethylsilyl)ethoxymethyl ether (CH$_2$OCH$_2$CH$_2$SiMe$_3$), Methoxymethyl ether, Tetrahydropyranyl ether, 3-Bromotetrahydropyranyl ether, Tetrahydrothiopyranyl ether, 1-Methoxycyclohexyl ether, 4-Methoxytetrahydropyranyl ether, 4-Methoxytetrahydrothiopyranyl ether, 1-[(2-Chloro-4-methyl)phenyl]-4-methoxypiperidin-4-yl ether, 1-(2-Fluorophenyl)-4-methoxypiperidin-4-yl ether, 1,4-Dioxan-2-yl ether, Tetrahydrofuranyl ether, Tetrahydrothiofuranyl ether, 2,3,3a,4,5,6,7,7a-octahydro-7,8,8-trimethyl-4,7-methanobenzofuran-2-yl ether, 1-Ethoxyethyl ether (CH(OC$_2$H$_5$)CH$_3$), 1-(2-Chloroethoxy)ethyl ether (CH(CH$_3$)OCH$_2$CH$_2$Cl), 1-[2-(Trimethylsilyl)ethoxy]ethyl ether, 1-Methyl-1-methoxyethyl ether (C(OCH$_3$)(CH$_3$)$_2$), 1-Methyl-1-benzyloxyethyl ether (C(OBn)(CH$_3$)$_2$), 1-Methyl-1-benzyloxy-2-fluoroethyl ether (C(OBn)(CH$_2$F)(CH$_3$)), 1-Methyl-1-phenoxyethyl ether (C(OPh)(CH$_3$)$_2$), 2,2,2-trichloro-ethyl ether (CH$_2$CCl$_3$), 1,1-Dianisyl-2,2,2-trichloro-ethyl ether, 1,1,1,3,3,3-Hexafluoro-2-phenylisopropyl ether (C(CHF$_3$)$_2$Ph), 2-Trimethylsilylethyl ether (CH$_2$SiMe$_3$), 2-(Benzylthio)ethyl ether (CH$_2$CH$_2$SBn), 2-(Phenylselenyl)ethyl ether (CH$_2$CH$_2$SePh), t-Butyl ether, Allyl ether (CH$_2$CH=CH$_2$), Propargyl ether (CH$_2$C≡CH), p-Methoxyphenyl ether (C$_6$H$_4$O—p-Me), p-Nitrophenyl ether (C$_6$H$_4$—p-NO$_2$), 2,4-Dinitrophenyl ether (C$_6$H$_3$-2,4-(NO$_2$)$_2$), 2,3,5,6-Tetrafluoro-4-(trifluoroacetitcmethyl)phenyl ether (C$_6$F$_4$CF$_3$), Benzyl ether (CH$_2$Ph), p-Methoxybenzyl ether (CH$_2$C$_6$H$_4$—p-OMe), 3,4-Dimethoxybenzyl ether (CH$_2$C$_6$H$_3$-3,4-(OMe)$_2$), o-Nitrobenzyl ether (CH$_2$C$_6$H$_4$—o-NO$_2$), p-Nitrobenzyl ether (CH$_2$C$_6$H$_4$—p-NO$_2$), p-Halobenzyl ether (CH$_2$C$_6$H$_4$—p-X, X = Br, Cl), 2,6-Dichlorobenzyl ether (CH$_2$C$_6$H$_3$-2,6-Cl$_2$), p-Cyanobenzyl ether (CH$_2$C$_6$H$_4$—p-CN), p-Phenylbenzyl ether (CH$_2$C$_6$H$_4$—p-C$_6$H$_5$), 2,6-Difluorobenzyl ether (CH$_2$C$_6$H$_4$F$_2$), p-Acylamino-benzyl ether (CH$_2$C$_6$H$_3$—p-NHCOR'), p-Azidobenzyl ether (CH$_2$C$_6$H$_4$-4-N$_3$),4-Azido-3-chlorobenxyl ether (CH$_2$C$_6$H$_3$-3-Cl-4-N$_3$), 2-Trifluoroacetitcmethylbenzyl ether (CH$_2$C$_6$H$_4$-2-CF$_3$), p-(Methylsulfinyl)benzyl ether (CH$_2$C$_6$H$_4$—p-(MeS(O)), 2- and 4-Picolyl ether(CH$_2$C$_5$H$_4$N), 3-Methyl-2-picolyl N-Oxido ether, 2-Quinolinylmethyl ether, 1-Pyrenylmethyl ether, Diphenylmethyl ether (CHPh$_2$), p,p'-Dinitrobenzhydryl ether (CH(C$_6$H$_4$—p-NO$_2$)$_2$), 5-Dibenzosuberyl ether, Triphenyl-methyl ether, p-Methoxyphenyldiphenylmethyl ether (C(Ph)$_2$C$_6$H$_4$—p-OMe), Di(p-methoxyphenyl)phenylmethyl ether (CPh(p-MeOC$_6$H$_4$)$_2$), Tri(p-methoxyphenyl)methyl ether (C(p-MeOC$_6$H$_4$)$_3$), 4-(4'-Bromophenacyloxy)phenyldiphenyl-methyl ether (C(Ph)$_2$C$_6$H$_4$—p-(OCH$_2$(O)CC$_6$H$_4$—p-Br), 4,4',4''-Tris(4,5-dichlorophthalimidophenyl)methyl ether, 4,4',4''-Tris(levulinoyloxyphenyl)methyl) ether, 4,4'4''-Tris(benzoyloxyphenyl)methyl) ether, 4,4'-Dimethoxy-3''-[N-(imidazolylmethyl)]trityl ether, 4,4'-Dimethoxy,3''-[N-(imidazolylethyl)carbamoyl)trityl ether, 1,1-Bis(4-methoxyphenyl)-1-pytenylmethyl ether, 4-(17-tetrabenzo[a,c,g,i]fluorenyl-methyl)-4',4''-dimethoxytrityl ether, 9-Anthryl ether, 9-(9-Phenyl)xanthenyl ether, Tritylone ether, 1,3-Benzodithiolan-2-yl ether, Benziisothiazolyl-S,S-dioxido ether, Trimethylsilyl (e.g., Si(CH$_3$)$_3$) ether, Triethylsilyl (SiEt$_3$) ether, Triisopropyl-silyl (Si(i-Pr)$_3$) ether, Dimethylisopropylsilyl (SiMe$_2$—i-Pr) ether, Diethylisopropylsilyl (SiEt$_2$—i-Pr) ether, Dimethyl-thesilyl ether ((CH$_3$)$_2$Si(CH$_3$)$_2$CCH(CH$_3$)$_2$), t-Butyldimethyl-silyl ether (SiMe$_2$—t-Bu),t-Butyldiphenylsilyl ether (SiPh$_2$—t-Bu), Tribenxylsily ether (Si(CH$_2$C$_6$H$_5$)$_3$), Tri-p-xylylsilyl ether (Si(CH$_2$C$_6$H$_4$—p-CH$_3$)$_3$), Triphenylsilyl ether (SiPh$_3$), Di-phenylmethylsilyl ether (SiMePh$_2$), Di-t-butylmethylsilyl ether (SiMe(t-Bu)$_2$),Tris(trimethylsilyl)silyl ether ([Si[Si(CH$_3$)$_3$]$_3$), (2-Hydroxystyryl)dimethylsilyl ether, (2-Hydroxystyryl)diiso-propylsilyl ether, t-Butylmethoxyphenylsilyl ether (SiPh(OCH$_3$)—t-Bu), t-Butoxydiphenylsilyl ether (Si(t-OBu)Ph$_2$), Formate ester (CHO), Benzoylformate ester (COCOPh), Acetate ester (COCH$_3$), Chloroacetate ester (COCH$_2$Cl), Dichloroacetate ester (COCHCl$_2$), Trichloro-acetate ester (COCCl$_3$), Trifluoroaceticacetate ester (COCF$_3$), Methoxyacetate ester (COCH$_2$OMe), Triphenylmethoxyacetate ester (COCH$_2$OCPh$_3$), Phenoxyaetate ester (COCH$_2$OPh), p-chlorophenoxyacetate ester (COCH$_2$OC$_6$H$_4$—p-Cl), phenyl-acetate ester (COCH$_2$Ph), P-P-Phenylacetate ester (COCH$_2$C$_6$H$_4$—p-P), Diphenylacetate ester (COCHPh$_2$), Nicotinate ester, 3-Phenylpropionate ester (COCH$_2$CH$_2$Ph), 4-Pentenoate ester (COCH$_2$CH$_2$CH=CH$_2$), 4-Oxopentanoate ester (COCH$_2$CH$_2$COCH$_3$), 4,4-(Ethylenedithio)pentanoate ester, 5-[3-Bis(4-methoxyphenyl)hydroxymethyl-phenoxy]levulinic acid ester, Pivaloate (COC(CH$_3$)$_3$) ester, Crotonate ester (COCH=CHCH$_3$), 4-Methoxycrotonate ester (COCH=CHCH$_2$OCH$_3$), Benzoate ester (COPh), p-Phenyl-benzoate ester (COC$_6$H$_4$—p-C$_6$H$_5$), 2,4,6-Trimethylbenzoate ester (COC$_6$H$_2$-2,4,6-Me$_3$), Alkyl methyl carbonate (CO$_2$CH$_3$), Methoxymethyl carbonate (CO$_2$CH$_2$OCH$_3$), alkyl 9-fluor-enylmethyl carbonate, Alkyl ethyl carbonate (CO$_2$Et), Alkyl 2,2,2-Trichloroethyl carbonate (CO$_2$CH$_2$CCl$_3$), 1,1-Dimethyl-2,2,2-trichloroethyl carbonate (CO$_2$C(CH$_3$)$_2$CCl$_3$), Alkyl 2-(trimethylsilyl)ethyl carbonate (CO$_2$CH$_2$CH$_2$SiMe$_3$), Alkyl 2-(phenylsulfonyl)ethyl caronate (CO$_2$CH$_2$CH$_2$SO$_2$Ph), Alkyl isobutyl carbonate (CO$_2$CH$_2$CH(CH$_3$)$_2$), Alkyl vinyl carbonate |

TABLE 1-continued

| Functional group | Protecting group (R'=R⁸) |
|---|---|
| | (CO₂CH=CH₂), Alkyl allyl carbonate (CO₂CH₂CH=CH₂), Alkyl p-nitrophenyl carbonate (CO₂C₆H₄—p-NO₂), Alkyl benzyl carbonate (CO₂Bn), Alkyl p-methoxybenzyl carbonate (CO₂CH₂C₆H₄—p-OMe), Alkyl 3,4-dimethoxybenzyl carbonate (CO₂CH₂C₆H₃-3,4-(OMe)₂), Alkyl o-nitrobenzyl carbonate (CO₂CH₂C₆H₄—o-NO₂), Alkyl p-nitrobenzyl carbonate (CO₂CH₂C₆H₄—p-NO₂), 2-Dansylethyl carbonate, 2-(4-Nitrophenyl)ethyl carbonate (CO₂CH₂CH₂C₆H₄-4-NO₂), 2-(2,4-dinitrophenyl)ethyl carbonate (CO₂CH₂CH₂C₆H₃-2,4-(NO₂)₂), 2-Cyano-1-phenylethyl carbonate (CO₂(C₆H₅)CHCH₂CN), Alkyl S-Benzyl thiocarbonate (COSCH₂Ph), Alkyl 4-ethoxy-1-naphthyl carbonate, Alkyl methyl dithiocarbonate (SCSCH₃), 2-iodobenzoate ester (COC₆H₄-2-I), 4-Azidobutyrate ester (CO(CH₂)₃N₃), 4-Nitro-4-methylpentanoate ester, o-(dibromomethyl)benzoate ester (COC₆H₄—o-(CHBr₂)), 2-Formylbenzenesulfonate ester, Alkyl 2-(methylthiomethoxy)ethyl carbonate (CO₂CH₂CH₂OCH₂SCH₃), 4-(Methylthiomethoxy)butyrate ester (CO(CH₂)₃OCH₂SCH₃), 2-(Methylthiomethoxymethyl)benzoate ester (COC₆H₄-2-(CH₂OCH₂SCH₃)), 2-(Chloroacetoxymethyl)benzioate ester, 2-[(2-chloroacetoxy)ethyl]benzoate ester, 2-[2-(Benzyloxy)ethyl]benzoate ester, 2-[2-(4-Methoxybenzyloxy)ethyl]benzoate ester, 2,6-Dichloro-4-methylphenoxyacetate ester, 2,6-Dichloro-4-(1,1,3,3-tetramethylbutyl)phenoxyacetate ester, 2,4-Bis(1,1-dimethylpropyl)phenoxyacetate ester, Chlorodiphenylacetate ester, Isobutyrate ester, Monosuccinoate ester, (E)-2-Methyl-2-Butenoate ester, o-(Methoxycarbonyl)benzoate ester, p-P-Benzoate ester, α-Naphthoate ester, Nitrate ester, Alkyl N,N,N',N'-tetramethylphosphorodiamidate, 2-Chlorobenzoate ester, 4-Bromobenzoate ester, 4-Nitrobenzoate ester, 3,5-Dimethoxybenzoin carbonate, A wild and woolly photolabile fluorescent ester, Alkyl N-phenylcarbamate, Borate ester, Dimethylphosphinothioyl ester ((S)P(CH₃)₂), Alkyl 2,4-dinitrophenylsulfenate (SC₆H₃-2,4-(NO₂)₂), Sulfate, Allylsulfonate (SOCH₂CH=CH₂), Methanesulfonate (SO₂Me), Benzylsulfonate (SO₂Bn), Tosylate (SO₂C₆H₄CH₃), 2-[(4-Nitrophenyl)ethyl]sulfonate (SO₂CH₂CH₂C₆H₄-4-NO₂) |
| Amino group (RNR') | Formamide (CHO), Acetamide (Ac), Chloroacetamide (COCH₂Cl), Trichloroacetamide (COCCl₃), Trifluoroacetic-acetamide (COCF₃), Phenylacetamide (COCH₂C₆H₅), 3-Phenylpropanamide (COCH₂CH₂C₆H₅), Pent-4-enamide ((O)CH₂CH₂CH=CH₂), Picolinamide (CO-2-pyridyl), 3-Pyridylcarboxamide (CO-3-Pyridyl), N-Benzoylphenylalanyl derivatives (COCH(NHCOC₆H₅)CH₂C₆H₅), Benzamide (COC₆H₅), p-Phenbenzamide (COC₆H₄—p-C₆H₅) |
| Amide group (CORNR') | N-Allylamide (CH₂CH=CH₂), N-t-Butylamide (t-Bu), N-Dicyclopropylmethylamide (CH(C₃H₅)₂), N-Methoxymethylamide (CH₂OCH₃), N-Methylthiomethylamide (CH₂SCH₃), N-Benzyloxymethylamide (CH₂OCH₂C₆H₅), N-2,2,2-Trichloroethoxymethylamide (CH₂OCH₂CCl₃), N-t-Butyldimethyl-siloxymethylamide (CH₂OSi(CH3)₂—y-C₄H₉), N-Pivaloyloxymethylamide (CH₂CO₂C(CH₃)₃), N-Cyanomethylamide (CH₂CHN), N-Pyrrolidinomethylamide, N-Methoxyamide (OMe), N-Benzyloxyamide (OCH₂C₆H₅), N-Methylthioamide (SMe), N-Triphenylmethylthioamide (SCPh₃), N-t-Butyldiethylsilylamide (Si(CH₃)₂—t-C₄H₉), N-Triisopropylsilylamide (Si(i-Pr)₃), N-4-Methoxyphenylamide (C₆H₄-4-OCH₃), N-4-(Methoxymethoxy)phenylamide (C₆H₄(OCH₃)₂), N-2-Methoxy-1-naphthylamide (C₁₀H₆-2-OCH₃), N-Benzylamide (CH₂C₆H₅), N-4-Methoxybenzylamide (CH₂C₆H₄-4-OCH₃), N-2,4-Dimethoxybenzylamide N-3,4-Dimethoxybenzylamide (CH₂C₆HH₃-2,4(3,4)-(OCH₃)₂), N-2-Acetoxy-4-methoxybenzylamide (CH₂C₆HH₃-4-OMe-2-Ac), N-o-nitrobenzylamide (CH₂C₆H₄-2-NO₂), N-Bis(4-methoxyphenyl)methylamide (CH(C₆H₄-4-OMe)₂), N-Bis(4-(methoxyphenyl)phenylmethyl-amide (CPh—(C₆H₄-4-OMe)₂), N-Bis(4-methylsulfinyl-phenyl)methylamide (CH(C₆H₄(O)S-4-Me)₂), N-Triphenyl-methylamide (C(C₆H₅)₃), N-9-Phenylfluorenylamide, N-t-Butoxycarbonylamide (CO—t-OC₄H₉), N-benzyloxycarbonylamide, N-Methoxycarbonylamide (COOMe), N-Ethoxycarbonylamide (COOEt), N-p-Toluenesulfonylamide, N-Butenylamide (CH=CHCH₂CH₃), N-[(E)-2-(Methoxycarbonyl)vinyl]amide (CH=CCO₂Me), N-Diethoxymethyl-amide (CH(OEt)₂), N-(1-Methoxy-2,2-dimethylpropyl)amide, N-2-(4-Methylphenylsulfonyl)ethylamide (CH₂CH₂SO₂C₆H₄-4-CH₃) |

More preferably, among the definitions for $R^6$ and $R^{10}$, the acrylate compound may be an acrylate; an acrylate with a C1 to C30, substituted or unsubstituted, linear or branched alkyl group unsubstituted or substituted with at least one selected from the group consisting of a halogen atom, a C1 to C12 alkoxy, an acryloyloxy, and an amino acid (e.g., ethyl acrylate, ethoxyethyl acrylate, diethoxyethyl acrylate, butyl acrylate, propyl acrylate, hexyl acrylate, 3-chloro-2-propyl acrylate, 3-(acryloyloxy)-2-propyl acrylate, glycine ethyl acrylate, and the like); an acrylate having an amino acid group (e.g., glycidyl acrylate and the like); ethylene glycol acrylate; or a polyethyleneglycol acrylate having polyethyleneglycol of the weight-average molecular weight of 200 to 2,500, the methacrylate compound may be a methacrylate; a methacrylate having a C1 to C30, substituted or unsubstituted, linear or branched alkyl group unsubstituted or substituted with at least one selected from the group consisting of a halogen atom, a C1 to C12 alkoxy, an acryloyloxy, and an amino acid (e.g., ethyl methacrylate, ethoxyethyl methacrylate, diethoxyethyl methacrylate, butyl methacrylate, propyl methacrylate, hexyl acrylate, 3-chloro-2-propyl methacrylate, 3-(acryloyloxy)-2-propyl methacrylate, glycine ethyl methacrylate, and the like); methacrylate having an amino acid group (e.g., glycidyl methacrylate, and the like); ethyleneglycol methacrylate; or polyethyleneglycol methacrylate having polyethyleneglycol of the weight-average molecular weight of 200 to 2,500, the acrylamide compound may be an acryl amide; an acryl amide having a C1 to C30, substituted or unsubstituted, linear or branched alkyl group unsubstituted or substituted with at least one selected from the group consisting of a halogen atom, a C1 to C12 alkoxy, acryloyloxy, and an amino acid (e.g., ethyl acrylamide, ethoxyethyl acrylamide, diethoxyethyl acrylamide, butyl acrylamide, propyl acrylamide, hexyl acrylamide, 3-chloro-2-propyl acrylamide, 3-(acryloyloxy)-2-propyl acrylamide, N-isopropyl acrylamide, glycyl ethyl acrylamide, and the like); an acrylamide having an amino acid group (e.g., glycidyl acrylamide, and the like); ethylene glycol acrylamide; or polyethyleneglycol amide having polyethyleneglycol of the weight-average molecular weight of 200 to 2,500, the vinyl sulfone compound may be vinyl sulfone, vinyl sulfone-ethylene glycol, vinyl sulfone-polyethyleneglycol having polyethyleneglycol of the weight-average molecular weight of 200 to 2,500, a vinyl sulfone-alkylate having a C1 to C30 alkyl group, a vinyl sulfone-amino acid (e.g., vinyl sulfone-cysteine, and the like), or a vinyl sulfone-peptide, the thiol compound may be thiol-polyethyleneglycol having polyethylene glycol of the weight-average molecular weight of 200 to 2,500, or a thiol-alkylate having a C1 to C30 alkyl group, the cysteine compound may be cysteine, N-acetyl-cysteine, or N-acetyl-cysteine alkyl ester having a C1 to C30 alkyl (e.g., N-acetyl-cysteine methyl ester or N-acetyl-cysteine ethyl ester), the cisteamine compound may be cisteamine, or N-acetyl-cisteamine, the mercaptic acid compound may be 2-mercapto succinic acid, the allyl pyrimidine compound may be 1-allyl-2-aminopyridinium, or 1-allyl-6-amino-3-ethyl-5-nitrosouracil, the tyramine compound may be tyramine, 3-methoxy-tyramine, or the like, the tyrosine compound may be tyrosine, or tyrosine methyl ester, or tyrosine ethyl ester, and the phenol derivative may be 2-amino-4-phenylphenol, 2-amino-4-tertiaryamylphenol, 2-amino-4-tert-butylphenol, 8-amino-2-naphthol, 5-amino-1-naphthol, 4-amino-1-naphthol, 3-amino-2-naphthol, 1-amino-2-naphthol, 4-amino 2,5 dimethyl phenol, 5-amino-2-methoxyphenol, 5-amino-2-methylphenol, 4-amino-3-methylphenol, 4-amino-2-methylphenol, 2-amino-5-methylphenol, 2-amino-4-methyl phenol, 2-amino-3-methylphenol, 2,4-diaminophenol, 2,3-diaminophenol, 4-aminophenol, 3-aminophenol, 2-aminophenol, 4-amino-3-nitrophenol, 4-amino-2-nitro phenol, 2-amino-5-nitrophenol, 2-amino-4-nitrophenol, 2-amino-4-fluorophenol, 4-amino-3-chlorophenol, 4-amino-2-chlorophenol, 3-amino-4-chlorophenol, 2-amino-5-chlorophenol, 2-amino-4-chlorophenol, 5-amino-2,4-dichlorophenol, 4-amino-3,6-dichlorophenol, 2-amino-4-chloro-6-nitrophenol, 4-amino-2,6-dibromophenol, or the like.

The physiologically active substance that can be used as $R^{11}$ may be selected from the group consisting of a protein, a polypeptide, a peptide, an antibody, a fusion protein, a hormone, a vaccine, a gene, an anti-cancer drug, an angiogenesis inhibitor, and the like having various functional groups such as a hydroxyl, an amide, an amino, a carboxylic, a thiol, a vinyl, an aldehyde, a halogen, a ketone groups, or the like.

The protein, the polypeptide, the peptide, the antibody, and the fusion protein may be at least one selected from the group consisting of erythropoietin (EPO), interferon-α, interferon-β, interferon-γ, a growth hormone releasing factor, a nerve growth factor (NGF), Granulocyte-colony stimulating factor (G-CSF), Granulocyte macrophage-colony stimulating factor (GM-CSF), macrophage-colony stimulating factor (M-CSF), a blood clotting factor, insulin, albumin (human, serum, etc.), botulinum toxin, oxytocin, vasopressin, a fibroblast growth factor (FGF), a epidermal growth factor (EGF), a platelet-derived growth factor (PDGF), a keratinocyte growth factor, an insulin-like growth factor (IGF), vascular endothelial growth factor (VEGF), a transforming growth factor-beta (TGF-β), a nerve growth factor, a brain-derived neurotrophic factor (BDNF), neurotrophin-3 (NT-3), neurotrophin-4/5, prolactin, luliberin, LHRH agonists, LHRH antagonists, glucagon, interleukin-2 (IL-2), interleukin-11 (IL-11), gastrin, tetragastrin, pentagastrin, urogastrone, secretin, enkephalins, endorphins, angiotensins, tumor necrosis factor (TNF), tumor necrosis factor related apoptosis inducing ligand (TRAIL), heparinase, bone morphogenic proteins (BMPs), hANP (human atrial natriuretic peptide), glucagon-like peptide (GLP-1), exnatide, calcitonin (human or salmon), teriparatide, coagulation factors such as Factor VII or Factor IX, hirudin, anakinra, renin, bradykinin, bacitracins, polymyxins, colistins, tyrocidine, gramicidins, cyclosporins, neurotensin, tachykinin, neuropeptide Y (NPY), peptide YY (PYY), vasoactive intestinal polypeptide (VIP), pituitray adenylate cyclase-activating polypeptide (PACAP) and synthetic analogue thereof, a peptide including RGD sequences, extracellular matrix proteins and peptides such as various types of collagen, fibronectin, laminin, vitronectin, proteoglycan, and the like, a monoclonal antibody (bevacizumab, cetuximab, panitunumab, trastuzumab, rituximab, adalimumab, infliximab, efalizumab, natalizumab, etc.), fusion proteins (etanercept, abatacept, alefacept, etc.), modified or drug-effective moieties, β-glucocerebrosidase, lactase, alglucosidase-α, α-galactosidase A, lipase, amylase, protease, hyaluronidase, $_L$-asparaginase, cytokines, and the like.

The hormone can be at least one selected from the group consisting of growth hormones or somatotropins (human, porcine, bovine, and the like), luteinizing hormone releasing hormone (LHRH), somatostatin, thyrotropin releasing hormone (TRH), adrenocorticotropic hormone, follicle-stimulating hormone (FSH), human chorionic gonadotropin (HCG), Lutropin-α, testosterone, estradiol, progesterones, prostaglandins, and their synthetic analogs, and modified or equivalent-efficacy substances.

The vaccine can be at least one selected from the group consisting of a hepatitis vaccine, HPV vaccine, and a lime disease vaccine, and the like.

The gene can be at least one selected from the group consisting of small interference RNA (siRNA), small hairpin RNA (shRNA), micro RNA (miRNA), aptamer, plasmid DNA, antisense oligodeoxynucleotide (AS-ODN), and the like.

The anti-cancer drug can be at least one selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxypogexterone acetate, epirubicin, letrozole, pirarubicin, topotecan, altretamine, toremifene citrate, BCNU, taxotere, actinomycin D, anasterozole, belotecan, imatinib, floxuridine, gemcitabine, hydroxyurea, zoledronate, vincristine, flutamide, valrubicin, streptozocin, silibinin, polyethyleneglygol conjugated anti-cancer drug, and their synthetic analogues, and modified or equivalent efficacy substances.

The angiogenesis inhibitor is BMS-275291 (Bristol-Myers Squibb, New York, N.Y.), clodronate, 6-deoxy-6-demethyl-4-dedimethylaminotetracycline (COL-3), doxycycline, marimastat, 2-methoxyestradiol, squalamine, SU5164, thalidomide, TNP-470 (methionine aminopeptidase-2 (MetAP-2) inhibitor), combretastatin A4, soy isoflavone, enzastaurin, CC 5013 (Revimid; Celgene Corp, Warren, N.J.), celecoxib, ZD 6474 (inhibitor of vascular endothelial growth factor receptor tyrosine kinase), halofuginone hydrobromide, interferon-α, bevacizumab, AE-941(Neovastat), interleukin-12, vascular endothelial growth factor-trap (VEFG-trap), cetuximab, rebimastat, matrix metalloproteinases (MMP) inhibitor (e.g., BMS-275291 (matrix metalloproteinases (MMPs) inhibitor, Bristol-Myers Squibb, New York, N.Y.), S-3304 (matrix metalloproteinases (MMPs) inhibitor) etc.), Protein kinase C beta inhibitor, (e.g., LY317615), endostatin, vatalanib (PTK787/ZK 222584), sunitinib malate (SU11248), cilenqitide (EMD-121974), humanized monoclonal antibody MEDI-522, EOS-200-4, Integrin alpha-5-beta-1 antagonist (ATN-161), and their synthetic analogues, and modified or equivalent efficacy substances.

In the poly(organophosphazene) according to the present invention, in order to impart to the polymer both of the thermosensitivity and the biodegradability, a hydrophobic amino acid ester [NHCH($R^1$)$CO_2R^2$ in the above Formula 1] and a hydrophilic molecule, methoxy polyethylene glycol, having the weight-average molecular weight ranging 350 to 10,000 are introduced into a dichlorophosphazene linear polymer; furthermore, an amino acid, a peptide, or a depsipeptide ester [NH($R^3$)($R^4$)($R^5$) in the above Formula 1], which can control the degradation rate of the polymer, may be partially introduced thereto.

Also, a functional group may be introduced into the poly(organophosphazene) of the present invention by directly introducing a substituent with a functional group such as hydroxyl group, amide group, amino group, thiol group, or carboxyl group to the polymer main chain at its side chain [NH($R^7$)($R^8$)($R^9$) in the above Chemical Formula 1]; or by introducing an amino acid ester or a peptide ester with the foregoing functional group substituted with a protecting group to the polymer main chain, and then deprotecting the same; or by introducing a substituent with a hydroxyl group to the polymer main chain, and then changing it into a carboxyl group through an esterification reaction.

Also, one can further introduce other functional group to the polyphosphazene by reacting the poly(organophosphazene) having carboxylic acid with folic acid, hyaluronic acid, cyclodextrin, an imidazole compound, histidine, lysine, arginine, cysteine, thioalkyl amine, spermine, spermidine, various molecular weights of polyethyleneimine, polyhistidine, polylysine, polyarginine, heparin, chitosan, protamine, or the like.

Protecting groups available in the present invention can be any of protection groups typically used for protecting each functional group (see, Protective groups in organic synthesis, Theodora W. Greene, Peter G. M. Wuts, Wiley-interscience, Third Edition), and any one ordinary skilled in the art could easily choose one of them for one's use.

Also, when $R^6$, $R^9$, or $R^{10}$ as introduced into the polymer has various functional groups such as a hydroxyl, an amide, an amino, a carboxyl, a thiol, or a vinyl group, one can introduce a range of physiologically active functional substances such as a protein, a polypeptide, a peptide, an antibody, a hormone, a vaccine, a gene, an anticancer drug, and an angiogenesis inhibitor that have various functional groups such as a hydroxyl, an amide, an amino, a carboxyl, a thiol, a vinyl, an aldehyde, a halogen, a keton groups into the polymers through covalent bonds.

Also, in the poly(organophosphazene) according to the present invention, one can control a temperature for sol-gel behavior (i.e., a gelling temperature), gel solidity, and/or biodegradation rate by adjusting the types of the hydrophobic amino acid ester, the types of the amino acid, the peptide, or the depsipeptide ester capable of controlling a degradation rate, the types of the substituent having the functional groups, the chain length of the methoxypolyethylene glycol, the compositions of all substituents, the weight-average molecular weights of the poly(organophosphazene), the polydispersity index, the concentration of the poly(organophosphazene) solution or the like. For example, increasing the composition of hydrophobic amino acid lowers the gelling temperature. As the concentration of the poly(organophosphazene) solution increases, the gelling temperature decreases and the gel solidity increases. As the chain length of methoxy polyethyleneglycol becomes longer, the gel solidity and the gelling temperature increase and the dissolution rate of the gel becomes faster. The poly(organophosphazene) comprising a depsipeptide ester biodegrades more rapidly than the poly(organophosphazene) having no depsipeptide ester. The poly(organophosphazene) comprising a substituent with a functional group of carboxylic acid biodegrades faster than the poly(organophosphazene) comprising no substituent with a functional group of carboxylic acid.

According to the present invention, both of the hydrophobic material and the hydrophilic material are introduced into the poly(organophosphazene). The polymer of the present invention may comprise a material for controlling degradation rate selected from the group consisting of an amino acid, a peptide, and a depsipeptide, and/or any of the functional groups selected from the group consisting of a hydroxyl, an amide, an amino, a thiol, and a carboxyl groups at its side chain. The polymer of the present invention shows sol-gel behavior at a temperature ranging from 5 to 70° C., more preferably from 15 to 50° C., possibly having the weight-average molecular weight of 3,000 to 1,500,000.

The poly(organophosphazene) is gelled at a body temperature either in itself as represented by Chemical Formula 1 or in the form of a hydrogel wherein chemical crosslinkings are formed within or between the poly(organophosphazene)(s) by the aforementioned manners. Therefore, when being injected into the body, the polymer forms a three-dimensional gel by the body temperature, and the hydrogel has crosslinkings developed by UV irradiation and/or the additives therein so that it has enhanced gel solidity. Furthermore, such a high level of gel solidity in the body can last for at least two months, preferably for over one year.

Therefore, according to the present invention, the crosslinked phosphazen polymers and/or the poly(organophosphazene)s with physiologically active substances covalently-bonded thereto are very useful for biomaterials implanted in a body, for example biomaterials that are required to have a sufficiently high gel solidity, such as materials for plastic surgery and orthopedics including a filler, tissue engineering biomaterials including artificial cartilage, dental materials, materials for preventing stenosis including stent, adhesion barriers, vasoocclusion materials, and the like. Also, when the physiologically active substance is simply mixed and carried in the hydrogels prepared by using them, a more compact inner-structure of the hydrogel can prevent the substance from being released early in a body in an excessively large amount when compared with the hydrogels without crosslinkings. Also, when the hydrogel made from the poly(organophosphazene)s has the physiologically active substance covalently-bonded thereto, one can control a release rate with a covalent bond breakage rate, making it possible to achieve more persistent and more effective release than the hydrogel containing a physiologically active substance simply mixed therein, and to provide excellent efficacy for delivering the physiologically active substances.

In this regard, other embodiment of the present invention provides a biomaterial which comprises at least one selected from the group consisting of:

a phosphazen polymer-containing hydrogel which comprises a solution containing a poly(organophosphazene) of Chemical Formula 1 wherein all of g, h, and i are simultaneously zero (0) (Chemical Formula 1-2) (i.e., having no physiologically active substance) at a concentration of 1 to 50 wt %; and chemical crosslinkings formed within or between the poly(organophosphazene)(s) by at least one treatment selected from the group consisting of UV irradiation; addition of one or more crosslinker selected from the group consisting of a thiol-based crosslinker and a vinyl-based crosslinker; addition of one or more additive selected from the group consisting of a pH regulator, a catalyst and an organic solvent; addition of an enzyme; and using a mixture of a solution of at least one poly(organophosphazene) with a thiol group and a solution of at least one poly(organophosphazene) with a vinyl group as the solution containing the poly(organophosphazene), a poly(organophosphazene) of Chemical Formula 1 with a physiologically active substance covalently-bonded thereto, and a phosphazen polymer-containing hydrogel with a physiologically active substance covalently-bonded thereto which comprises a solution containing a poly(organophosphazene) of Chemical Formula 1 at a concentration of 1 to 50 wt %, and chemical crosslinkings formed within or between the poly (organophosphazene)(s) by at least one treatment selected from the group consisting of UV irradiation; addition of one or more crosslinker selected from the group consisting of a thiol-based crosslinker and a vinyl-based crosslinker; addition of one or more additive selected from the group consisting of a pH regulator, a catalyst and an organic solvent; addition of an enzyme; and using a mixture of a solution of at least one poly(organophosphazene) with a thiol group and a solution of at least one poly(organophosphazene) with a vinyl group as the solution containing a poly(organophosphazene).

The biomaterial of the present invention can be at least one selected from the group consisting of materials for plastic surgery and orthopedics including a filler, tissue engineering biomaterials including artificial cartilage, various dental materials, materials for preventing stenosis including stent, vasoocclusion materials, adhesion barriers, and the like.

The hydrogel containing the poly(organophosphazene) of Chemical Formula 1 may comprise the poly(organophosphazene) of Chemical Formula 1 as dissolved in at least one suitable solvent selected from the group consisting of water, a buffered solution, an acidic solution, an alkaline solution, a salt solution, a saline solution, water for injection, and a glucose-saline solution at a concentration of 1 to 50 wt %, preferably at a concentration of 3 to 30 wt %. Since the poly(organophosphazene) of the present invention shows sol-gel behavior at a temperature of 5 to 70° C., and preferably at a temperature of 15 to 50° C., it can form a gel at a body temperature range, and thus it can be utilized for various types of injectionable biomaterials.

As described above, the hydrogel of the present invention is advantageous in that chemical crosslinkings are formed in the polymer of the above chemical formula by UV irradiation and/or a crosslinker, and/or an additive, and/or an enzyme, and/or mixing of at least one poly(organophosphazene) having the above chemical formula, and thereby it shows temperature-dependant sol-gel behavior and also has the gel solidity strong enough for various biomaterials. Furthermore, thanks to the chemical crosslinkings, the network structure becomes more compact and the pore sizes become smaller, making it possible to maintain a proper strength and volume for an extended period of time.

In the hydrogels of the present invention, the chemical crosslinkings can be formed by at least one among five conditions as follows:

(1) forming chemical crosslinkings by using as the solution of the poly(organophosphazene) a mixture of a solution of at least one poly(organophosphazene) having a thiol substituent and a solution of at least one poly(organophosphazene) having a vinyl substituent;

(2) forming chemical crosslinkings by UV irradiation;

(3) forming chemical crosslinkings by addition of a crosslinker;

(4) forming chemical crosslinkings by addition of an additive; and (5) forming chemical crosslinkings by an enzyme.

First, (1) when the chemical crosslinkings are formed by mixing the solution of the poly(organophosphazene) with a thiol substituent and the solution of the poly(organophosphazene) with a vinyl substituent, one can mix the solution of at least one poly(organophosphazene) whose $R^6$ and/or $R^{10}$ in Chemical Formula 1 is a substituent having a thiol group with the solution of at least one poly(organophosphazene) whose $R^6$ and/or $R^{10}$ in Chemical Formula 1 is a substituent having vinyl group to form chemical crosslinkings through Michael-Addition between the thiol group and the vinyl group. In order to aid or promote the formation of crosslinkings, additional treatments can be conducted with at least one photoinitiator, and/or at least one crosslinker, and/or at least one additives, which will be described hereinbelow.

Also, (2) when the poly(organophosphazene) whose $R^6$ and/or $R^{10}$ in Chemical Formula 1 is a substituent having a vinyl group, chemical crosslinkings can be made by UV irradiation and thus, the chemical crosslinkings can be made by UV irradiation and an optional addition of a photoinitiator. Therefore, the hydrogel may comprise a solution of at least one poly(organophosphazene) of Chemical Formula 1 and a photoinitiator. The photoinitiator may be contained in an amount of $1 \times 10^{-6}$ to 10% by weight, preferably $1 \times 10^{-3}$ to 1% by weight based on the total weight of the poly(organophosphazene)s. If the amount of photoinitiator is less than the foregoing range, a desired effect of the photoinitiator may not be obtained. On the other hand, if the amount exceeds the foregoing range, it may disadvantageously have an effect on the efficacy of active ingredients and/or the properties of the polymers showing the sol-gel behavior according to the present invention.

Photoinitiators suitable for use in the present invention can be any compound capable of forming radicals via light irradiation, and for example, at least one selected from the group consisting of ketone compounds, phosphine oxide compounds, alkyl ester compounds, benzoyl compounds, titanate salts, iodonium salts, dibenzoyl compounds, thiocarbonate compounds, dion compounds, and potassium sulfates. More preferably, the photoinitiator can be at least one selected from the group consisting of benzoyl peroxide, 2,2-dimethoxy-2-phenyl acetophenone, 2-hydroxy-1-[4-(2-hydroxytoxy)phenyl]-2-methyl-1-propanone, acylphosphineoxide compounds, methylbenzoylformate, oxy-phenyl-acetic acid 2-[2-oxo-2-phenyl-acetoxy-ethoxy]ethyl ester, oxy-phenyl-acetic 2-[2-hydroxy-ethoxy]-ethyl ester, α,α-dimethoxy-α-phenylacetophenone, 2-benzyl-2-(dimethylamino)-1-[4-(4-morpholinyl)phenyl]1-butanone, benzophenone, 2-hydroxy-4'-(2-hydroxyethoxy)-2-methylpropiophenone, 1-hydroxycyclohexyl-phenyl-ketone, 2-methyl-1-[4-(methylthio)phenyl]-2-(4-morpholinyl)1-propanone, 1-[4-(2-hydroxyethoxy)-phenyl]-2-hydroxy-2-methyl-1-propan-1-one, 2-hydroxy-2-methyl-1-phenyl-1-propanone, diphenyl (2,4,6-trimethylbenzoyl)-phosphine oxide, phosphine oxide, phenyl bis(2,4,6-trimethyl benzoyl), bis(eta 5-2,4-cyclopentadien-1-yl)titanium, bis[2,6-difluoro-3-(1H-pyrrol-1-yl) phenyl]titanium, iodonium, (4-methylphenyl)[4-(2-methylpropyl)phenyl iodonium salt, hexafluorophosphate iodonium salt, dibenzoyl disulfide compounds, diphenyl thiocarbonate, 2,2'-azobisisobutyronitrile, camphorquinone, dye eosin, potassium persulfate, potassium peroxodisulfate, and the like.

For the poly(organophosphazene) of Chemical Formula 1 wherein $R^6$ and/or $R^{10}$ is a substituent having a thiol group, crosslinkings can be made by carrying out UV irradiation and the addition of the photoinitiator, together with adding a crosslinker having a vinyl group capable of forming crosslinkings with the thiol group.

(3) In case of forming chemical crosslinkings by a crosslinker, the hydrogel of the present invention may include at least one poly(organophosphazene)s of Chemical Formula 1 and at least one crosslinker selected from the group consisting of a thiol-based crosslinker and a vinyl-based crosslinker. In this case, in order to form crosslinkings, the thiol-based crosslinker triggers Michael Addition with the vinyl group of the poly(organophosphazene) while the vinyl-based crosslinker triggers Michael Addition with the vinyl or thiol group of the poly(organophosphazene). The crosslinker can be used in an amount of $1 \times 10^{-6}$ to 30% by weight, preferably $1 \times 10^{-3}$ to 10% by weight based on the total weight of the poly(organophosphazene)s. If the amount of the crosslinker is below the foregoing range, one cannot obtain a desired effect thereof; on the other hand, if it is above the foregoing range, it may disadvantageously have an effect on the efficacy of active ingredients and/or the sol-gel behavior properties of the polymers according to the present invention.

Crosslinkers suitable for use in the present invention can be any one capable of triggering Michael Addition together with a thiol group or a vinyl group of the Chemical Formula 1, and thus one can use any compound that has two or more thiol groups and/or vinyl groups. Therefore, the crosslinker may be at least one selected from the group consisting of all compounds having at least two thiol groups and/or vinyl groups, and for example, at least one selected from the group consisting of compounds having a thiol group such as thiol compounds, dithiol compounds, and mercapto compounds; and compounds having a vinyl group such as a sulfur-containing amino acid, a sulfur-containing oligopeptide, acrylate compounds, diacrylate compounds, triacrylate compounds, tetraacrylate compounds, pentaacrylate compounds, hexaacrylate compounds, methacrylate compounds, dimethacrylate compounds, (di)vinyl compounds, protoporphyrin compounds, (di)vinyl-polyethyleneglycol compounds, (di)vinyl-sulfone-polyethyleneglycol compounds, diol compounds, allyl compounds, diallyl compounds, triallyl compounds, and the like.

More preferably, the crosslinker may be at least one selected from the group consisting of toluene-3,4-dithiol, 4-amino-4H-1,2,4-triazole-3,5-dithiol, (1,2,4) thiadiazole-3,5-dithiol, 5-(4-chloro-phenyl)-pyrimidine-4,6-dithiol, 7-H-purine-2,6-dithiol, M-carborane-1,7dithiol, O-carborane-1,2-dithiol, 1,3,4-thiadiazole, 1,6-hexanedithiol, 2,5-dithiol, benzene-1,2-dithiol, benzene-1,3-dithiol, biphenyl-4,4'-dithiol, bismuthiol, 2,3-dimercapto-1-propane sulfonic acid sodium salt monohydrate, 2,4-dimercapto-5-methylpyrimidine, 2,6-dimercapto-7-methyl purine, 2,8-dimercapto-6-hydroxy purine, 6,8-dimercapto-2-hydroxy purine, 2,2'-(ethylenedioxy)diethane thiol, 1,3-dimercapto-1-propanol, 1,2-ethanedithiol, ethylene glycol dithioacetate, 1,5-dimercaptopentane, 1,3-propanedithiol, dimercaptomethane, pentaerythritol tetrakis (2-mercaptopropinonate), pentaerythritol tetrakis(3-mercaptopropinonate), trimethylolpropane tris(2-mercaptoacetate), trimethylolpropane tris(3-mercaptoacetate), dithiothreitol, thiol-substituted poly(ethyleneglycol) derivatives such as a poly(ethyleneglycol)-dithiol compound having the weight-average molecular weight of 200 to 2,500, a N-thiol-glycylglycylglycyl-terminated poly(ethyleneglycol) compounds, thiol-substituted poly(ethyleneglycol) derivatives such as a 3-arm poly(ethyleneglycol)-thiol compound having the weight-average molecular weight of 1,000 to 20,000, a 4-arm poly(ethyleneglycol)-thiol compound having the weight-average molecular weight of 2000 to 20,000, a 8-arm poly(ethyleneglycol)-thiol compound having the weight-average molecular weight of 10,000 to 40,000, thiol-substituted polymers such as poly(ethyleneglycol-2-mercaptosuccinic acid) having the weight-average molecular weight of 200 to 25,000, biscysteine-oligopeptide, propylene glycol glycerolate diacrylate, di(ethyleneglycol)diacrylate, tri(propylene glycol)diacrylate, tetra(ethyleneglycol)diacrylate, tri(propylene glycol)glycerolate diacrylate, trimethylolpropane benzoate diacrylate, trimethylolpropane etoxylate methyl ether diacrylate, bisphenol A propoxylate diacrylate, bisphenol A propoxylate glycerolate diacrylate, bisphenol F etoxylate diacrylate, fluorescein O,O'-diacrylate, neopentyl glycol diacrylate, neopentyl glycol propoxylate diacrylate, pentaerythritol diacrylate monostearate, ethylene diacrylate, oxydiethylene diacrylate, 3-hydroxy-2,2-dimethylpropyl 3-hydroxy-2,2-dimethylpropinonate diacrylate, glycerol 1,3-diglycerolate diacrylate, 1,3-butanediol diacrylate, 1,4-butanediol diacrylate, 1,6-hexanediol diacrylate, 1,6-hexanediol etoxylate diacrylate, 1,6-hexanediol propoxylate diacrylate, bisphenol A etoxylate diacrylate having the weight-average molecular weight of 200 to 40,000, bisphenol A glycerolate diacrylate, pentaerythritol propoxylate triacrylate, pentaerythritol tetraacrylate, pentaerythritol triacrylate, trimethylpropane deoxylate triacrylate, trimethylolpropane propoxylate triacrylate, trimethylolpropane triacrylate, poly(ethyleneglycol)triacrylate having the weight-average molecular weight of 200 to 2,500, poly(ethyleneglycol)tetraacrylate having the weight-average molecular weight of 200 to 2,500, poly(ethyleneglycol) octaacrylate having the weight-average molecular weight of 200 to 2,500, acrylated 1,6-bis(p-carboxylphenoxy)hexane, acrylate 1,3-bis(p-carboxylphenoxy)propane, acrylate sebacic acid, poly(propyleneglycol)diacrylate having various molecular weights, poly(ethyleneglycol)-acrylate compounds having the weight-average molecular weight of 200 to 2,500, N-acrylate-glycylglycylglycyl-terminated poly(ethyleneglycol) compounds, acrylate-substituted poly(ethyleneglycol) derivatives such as 3-arm poly(ethyleneglycol)-acrylate compounds having the weight-average molecular weight of 1,000 to 20,000, 4-arm poly(ethyleneglycol)-acrylate compounds having the weight-average molecular weight of 2000 to 20,000, 8-arm poly(ethyleneglycol)acrylate compounds having the weight-average molecular weight of 10,000 to 40,000, a polymer having an acrylate substituent such as poly(ethyleneglycol)-b-poly(lactic acid)-diacrylate having the weight-average molecular weight of 2,000 to 40,000, poly(ethyleneglycol)-b-poly(glycolide)-diacrylate, poly(ethyleneglycol)-b-poly(alpha-hydroxyl acid)-diacrylate having the weight-average molecular weight of 2,000 to 40,000, ethylene glycol dimethacrylate, bisphenol A dimethacrylate, 1,3-bis(3-metaacryloxyloxypropyl)-1,1,3,3-tetramethyldisiloxane, 1,3-butanediol dimethacrylate, 1,4-butanediol dimethacrylate, bisphenol A etoxylate dimethacrylate, bisphenol A glycerolate dimethacrylate, di(ethylene glycol)dimethacrylate, diurethane dimethacrylate, fluorescein O,O'-dimethacrylate, glycerol dimethacrylate, neopentyl glycol dimethacrylate, ethylene dimethacrylate, oxydiethylene dimethacrylate, di(ethylene glycol) dimethacrylate, poly(lauryl methacrylate-co-ethylene glycol dimethacrylate) having the weight-average molecular weight of 200 to 40,000, poly(methyl methacrylate-co-ethylene glycol dimethacrylate) having the weight-average molecular weight of 200 to 40,000, poly(propylene glycol)dimethacrylate having the weight-average molecular weight of 200 to 2,500, tetraethylene glycol dim ethacrylate, triethylene glycol dimethacrylate, 2,2-bis[4-(2-hydroxy-3-methacryloyloxypropyl)phenyl]propane, etoxylate 2,2-bis[4-(2-hydroxy-3-methacryloyloxypropyl)phenyl]propane, 1,6-bis-[2-methacryloyloxyethoxycarbonylamino]2,4,4-trimethylhexane, dodecanediol dimethacrylate, trimethylolpropane trimethacrylate, methacrylated 1,6-bis(p-carboxylphenoxy)hexane, methacrylate 1,3-bis(p-carboxylphenoxy)propane, methacrylate sebacic acid, polyethylene glycol derivatives substituted with methacrylate such as poly (ethyleneglycol)-methacrylate compounds having the weight-average molecular weight of 200 to 2,500, N-methacrylate-glycylglycylglycyl-terminated poly(ethyleneglycol) compounds, 3-arm poly(ethyleneglycol)-methacrylate compounds having the weight-average molecular weight of 1,000 to 20,000, 4-arm poly(ethyleneglycol)-methacrylate compound having the weight-average molecular weight of 2000 to 20,000, 8-arm poly(ethyleneglycol)-methacrylate compounds having the weight-average molecular weight of 10,000 to 40,000, polymers substituted with methacrylate such as poly(ethyleneglycol)-b-poly(lactic acid)-dimethacrylate having the weight-average molecular weight of 200 to 40,000, poly(ethyleneglycol)-b-poly(glycolid)-dimethacrylate having the weight-average molecular weight of 200 to 40,000, poly(ethyleneglycol)-b-poly(α-hydroxylic acid)-dimethacrylate having the weight-average molecular weight of 200 to 40,000, diethylene glycol divinyl ether, triethylene glycol divinyl ether, divinylbenzene, poly (1,4-butanediol)divinyl ether, polytetrahydrofuran divinyl ether, 1,6-hexanediol divinyl ether, 1,1,3,3,-tetramethyl-1,3-divinyldisiloxane, 1,3-divinyltetramethyldisiloxane, 1,4-pentadiene-3-ol, 1,4-divinyl-1,1,2,2,3,3,4,4-octamethyltetrasilane, 2,5-divinyltetrahydropyran, 3,9-divinyl-2,4,8,10-tetraoxaspiro[5,5]undecane, 3,6-divinyl-2-methyltetrahydrofuran, divinylphenylphosphine, poly (ethyleneglycol)divinyl ethers having the weight-average molecular weight of 200 to 2,500, poly(styrene-co-bromostyrene-co-divinylbenzene), poly(styrene-co-divinylbenzene), protoporphyin IX, protoporphyin IX dimethyl ester, protoporphyin IX disodium salt, protoporphyin IX zinc, a 3-arm poly(ethyleneglycol)-vinyl compound having molecular weight 1,000 to 20,000, a 4-arm poly(ethyleneglycol)-vinyl compound having the weight-average molecular weight of 2000 to 20,000, a 8-arm poly(ethyleneglycol)-vinyl compound having the weight-average molecular weight 10,000 to 40,000, triallyl-1,3,5-triazine-2,4,6-(1H,3H,5H)-trione, trimethylopropane diallyl ether, 1,6-hexadiene, divinyl sulfoxide, sulfone-poly(ethyleneglycol), vinyl sulfone-3-arm poly (ethyleneglycol) having the weight-average molecular weight of 1000 to 20,000, vinyl sulfone-4-arm poly(ethyleneglycol) having the weight-average molecular weight of 2000 to 20,000, vinyl sulfone-8-arm poly(ethyleneglycol) having the weight-average molecular weight of 10,000 to 40,000, and 1,6-hexanediol di-(endo, exo-norborne-2-en-5-carboxylate), and the like.

Also, (4) in case of forming crosslinkings by additives, the additives can control the formation of crosslinkings either in a mixture of a solution of at least one polymer of Chemical Formula 1 wherein $R^6$ and/or $R^{10}$ is a substituent having a thiol group and a solution of at least one polymer of Chemical Formula 1 wherein $R^6$ and/or is a substituent having a vinyl group or in a solution of the poly(organophosphazene) of Chemical Formula 1 wherein $R^6$ and/or $R^{10}$ is a substituent having a thiol group. The content of the additives can range from $1\times10^{-6}$ to 10% by weight, preferably $1\times10^{-3}$ to 1% by weight based on the total weight of the poly(organophosphazene)s. If the content of additives is below the foregoing range, one cannot obtain a desired effect thereof; on the other hand, if it is above the foregoing range, it may disadvantageously have an effect on the efficacy of active ingredients and/or the properties of the polymers showing the sol-gel behavior according to the present invention.

Suitable additives for use in the present invention comprise any additive promoting the formation of the crosslinkings between a thiol group and a vinyl group or between the thiol groups in Chemical Formula 1. For example, one can use a compound capable of changing pH into a weak base such as sodium hydroxide, ammonia, potassium hydroxide, triethyl amine, sodium phosphate, trisbase, and HEPES and/or a catalyst such as hydrogen peroxide and ammonium peroxide, and/or an organic solvent such as DMSO.

Also, (5) in case of forming crosslinkings by an enzyme, the hydrogel according to the present invention can include at least one poly(organophosphazene) of Chemical Formula 1 and hydrogen peroxide and an oxydoreductase enzyme. The oxydoreductase enzyme refers to all enzymes capable of triggering an enzyme-substrate reaction with tyramine or tyrosine in the poly(organophosphazene) to form enzymatic crosslinkings. For example, it comprises transglutaminase, laccase, bilirubin oxidase (BOD), manganese (II), hematin, horseradish peroxidase, and the like. Preferably, horseradish peroxidase can be used. The content of the enzyme ranges from $1\times10^{-6}$ to 200% by weight, preferably from $1\times10^{-3}$ to 100% by weight based on the total weight of the poly(organophosphazene)s. If the content of the enzyme is below the foregoing range, one cannot obtain a desired effect thereof; on the other hand, if it is above the foregoing range, the enzyme may disadvantageously have an effect on the efficacy of active ingredients and/or the sol-gel behavior properties of the polymers according to the present invention. Therefore, the foregoing ranges are desirable.

Also, the poly(organophosphazene)s with physiologically active substances covalently-bonded thereto and/or the hydrogels comprising the poly(organophosphazene)s with physiologically active substances covalently-bonded thereto can contribute to enhancing biocompatibility and functionality of biomaterials by the physiologically active substance covalently-bonded thereto. Also, when the biomaterial aiming for a use as a composition for delivering a physiologically active substance is injected into a body, the covalent bonds between the physiologically active substance and the polymers can suppress the early release of an excessively large amount of the physiologically active substance. Moreover, since the physiologically active substance is not released until the breakage of the covalent bond, one can control the release rate of the physiologically active substance by changing the types of the covalent bonds.

Therefore, another embodiment of the present invention provides a composition for delivering physiologically active substances which comprises the poly(organophosphazene)s with the physiologically active substance covalently-bonded thereto and/or the hydrogel containing the poly(organophosphazene)s with the physiologically active substance covalently-bonded thereto.

The physiologically active substances covalently-bonded to the poly(organophosphazene)s refer to any materials having a beneficial effect in a body and for example, they may be drugs having various functional groups such as a hydroxyl, an amide, an amino, a carboxyl, a thiol, a vinyl, an aldehyde, a halogen, and a ketone groups. The drugs can be at least one selected from the group consisting of a protein, a polypeptide, a peptide, a fusion protein, an antibody, a hormone, a vaccine, a gene, an anticancer drug, an angiogenesis inhibitor, and the like.

The protein, the polypeptide, the peptide, the antibody, and the fusion protein may be at least one selected from the group consisting of erythropoietin (EPO), interferon-α, interferon-β, interferon-γ, a growth hormone releasing factor, a nerve growth factor (NGF), a granulocyte-colony stimulating factor (G-CSF), a granulocyte macrophage-colony stimulating factor (GM-CSF), a macrophage-colony stimulating factor (M-CSF), a blood clotting factor, insulin, albumin (human, serum, etc.), botulinum toxin, oxytocin, vasopressin, a fibroblast growth factor (FGF), a epidermal growth factor (EGF), a platelet-derived growth factor (PDGF), a keratinocyte growth factor, an insulin-like growth factor (IGF), vascular endothelial growth factor (VEGF), a transforming growth factor-beta (TGF-β), a nerve growth factor, a brain-derived neurotrophic factor (BDNF), neurotrophin-3 (NT-3), neurotrophin-4/5, prolactin, luliberin, LHRH agonists, LHRH antagonists, glucagon, interleukin-2 (IL-2), interleukin-11 (IL-11), gastrin, tetragastrin, pentagastrin, urogastrone, secretin, enkephalins, endorphins, angiotensins, tumor necrosis factor (TNF), tumor necrosis factor related apoptosis inducing ligand (TRAIL), heparinase, bone morphogenic proteins (BMPs), hANP (human atrial natriuretic peptide), glucagon-like peptide (GLP-1), exnatide, calcitonin (human or salmon), teriparatide, coagulation factors such as Factor VII or Factor IX, hirudin, anakinra, renin, bradykinin, bacitracins, polymyxins, colistins, tyrocidine, gramicidins, cyclosporine, neurotensin, tachykinin, neuropeptide Y (NPY), peptide YY (PYY), vasoactive intestinal polypeptide (VIP), pituitray adenylate cyclase-activating polypeptide (PACAP) and synthetic analogue thereof, RGD, extracellular matrix proteins and peptides such as various types of collagen, fibronectin, laminin, vitronectin, and proteoglycan, a monoclonal antibody such as bevacizumab, cetuximab, panitunumab, trastuzumab, rituximab, adalimumab, infliximab, efalizumab, natalizumab and the like, antibodies of fusion proteins such as etanercept, abatacept, and alefacept, modified or drug-effective moieties, enzymes such as β-glucocerebrosidase, lactase, alglucosidase-α, α-galactosidase A, lipase, amylase, protease, hyaluronidase, and $_L$-asparaginase, cytokines, and the like.

The hormone can be at least one selected from the group consisting of growth hormones or somatotropins (human, porcine, bovine, and the like), luteinizing hormone releasing hormone (LHRH), somatostatin, thyrotropin releasing hormone (TRH), adrenocorticotropic hormone, follicle-stimulating hormone (FSH), human chorionic gonadotropin (HCG), lutropin-α, testosterone, estradiol, progesterones, prostaglandins, and their synthetic analogs, and modified or equivalent efficacy substances.

The vaccine can be at least one selected from the group consisting of a hepatitis vaccine, HPV vaccine, and a lime disease vaccine, and the like.

The gene can be at least one selected from the group consisting of micro RNA (miRNA) including small interference RNA (siRNA), small hairpin RNA (shRNA), and the like, aptamers, plasmid DNA, antisense oligodeoxynucleotide (AS-ODN), and the like.

The anticancer drug can be at least one selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxypogexterone acetate, epirubicin, letrozole, pirarubicin, topotecan, altretamine, toremifene citrate, BCNU, taxotere, actinomycin D, anasterozole, belotecan, Imatinib, floxuridine, gemcitabine, hydroxyurea, zoledronate, vincristine, flutamide, valrubicin, streptozocin, silibinin, polyethyleneglygol conjugated anticancer drug, and their synthetic analogs, and modified or equivalent efficacy substances.

The angiogenesis inhibitor is BMS-275291 (Bristol-Myers Squibb, New York, N.Y.), clodronate, 6-deoxy-6-demethyl-4-dedimethylaminotetracycline (COL-3), doxycycline, marimastat, 2-methoxyestradiol, squalamine, SU5164, thalidomide, TNP-470, combretastatin A4, soy isoflavone, enzastaurin, CC 5013 (Revimid; Celgene Corp, Warren, N.J.), celecoxib, ZD 6474, halofuginone hydrobromide, interferon-α, bevacizumab, AE-941, interleukin-12, vascular endothelial growth factor-trap (VEFG-trap), cetuximab, rebimastat, matrix metalloproteinases (MMP) inhibitor (e.g., BMS-275291 (Bristol-Myers Squibb, New York, N.Y.), S-3304, etc.), protein kinase C beta inhibitor, (e.g., LY317615), endostatin, vatalanib (PTK787/ZK 222584), sunitinib malate (SU11248), cilenqitide (EMD-121974), humanized monoclonal antibody MEDI-522, EOS-200-4, Integrin alpha-5-beta-1 antagonist (ATN-161), and their synthetic analogues, and modified or equivalent efficacy substances.

In case of simply mixing an additional drug and/or an additional therapeutic cell with the delivery composition for physiologically active substances in accordance with the present invention, the drugs (i.e., the simply-mixed one) are advantageously contained in an amount of $1 \times 10^{-8}$ to 50% by volume, preferably $1 \times 10^{-4}$ to 20% by volume based on the total volume in the delivery system for the physiologically active substances. Also, when the delivery system for the physiologically active substance comprises cells as the physiologically active substance, the cells are included preferably in an amount of $1 \times 10^{-8}$ to 50% by volume based on the total volume in the delivery system for the physiologically active substances. If the content of the drugs or the cells is below the foregoing range, one cannot obtain a desired effect thereof; on the other hand, if it is above the foregoing range, the drugs or the cells may disadvantageously have an effect on the efficacy of active ingredients and/or the properties of the polymers.

The drugs can be at least one selected from the group consisting of a protein, a polypeptide, a peptide, an antibody, a hormone, a vaccine, a gene, an anticancer drug, and an angiogenesis inhibitor, the types of which are the same as described above.

The therapeutic cells can be at least one selected from the group consisting of preosteoblasts, chondrocytes, umbilical vein endothelial cells (UVEC), osteoblasts, adult stem cells, schwann cells, oligodendrocytes, hepatocytes, mural cells (remedy in combination with UVEC), myoblasts, insulin-secreting cells, endothelial cells, smooth muscle cells, fibroblasts, β cells, endodermal cells, hepatic stem cells, juxraglomerular cells, skeletal muscle cells, keratinocytes, melanocytes, langerhans cells, merkel cells, dermal fibroblasts, preadipocytes, adipocytes and the like.

The physiologically active substances may be added alone to the poly(organophosphazene)s. Alternatively, they can be added and mixed prior to, after, or at the same time of adding the photoinitiators, and/or UV irradiation and/or the crosslinkers and/or the additives and/or the enzymes and/or the poly(organophosphazene)s having functional groups. After being injected into the body, the physiologically active substances can be effectively carried in the polymers thanks to the gelation of the polymers in combination with the crosslinkings by the action of the photoinitiators and/or the crosslinkers and/or the additives and/or the enzymes and/or the poly(organophosphazene)s having functional groups.

The poly(organophosphazene)s of Chemical Formula 1 with the physiologically active substances covalently-bonded thereto or the hydrogels comprising the same may further comprise the additives as described hereinafter. Further comprising such additives may have an advantageous effect on the use of the polymers and/or the hydrogels for the biomaterials.

As previously mentioned, adding the additives such as various salts to the poly(organophosphazene)s or the hydrogels of the present invention enables one to control the sol-gel behavior of the aqueous solution of the poly(organophosphazene) and to obtain a desired level of gel solidity and a desired degree of the temperature for sol-gel transition (See, Macromolecules 32, 7820, 1999). Also, among the uses of the poly(organophosphazene) of the present invention, the delivery system of the physiologically active substance may further comprise a range of additives, increasing the utility of the polymer hydrogel as a delivery material for a physiologically active substance such as drugs. If the polypeptide or protein drug is to be delivered, introducing suitable additives makes it possible to maintain the drug safety in the hydrogel, and the chemical bonds induced thereby such as an ionic bond between these drugs and the additives enable one to control the release rate of the drug from the hydrogels. Also, if the therapeutic cells are to be delivered, the additives as introduced into the hydrogels may enhance the activity of the cells as delivered to a body.

In other words, the additives can induce a range of interactions for chemical bonding such as ionic bondings between the poly(organophosphazene)s or the hydrogels thereof and the physiologically active substances such as drugs so as to control the release of the physiologically active substances and/or to enhance in vivo activity of the physiologically active substances such as therapeutic cells.

In the present invention, the content of the additive may be from $1 \times 10^{-6}$ to 30% by weight, preferably $1 \times 10^{-3}$ to 10% by weight based on the total weight of the physiologically active substance. If the content of the additives is below the foregoing range, one cannot obtain a desired effect thereof; on the other hand, if it is above the foregoing range, the additives may disadvantageously have an effect on the efficacy of active ingredients and/or the properties of the polymers according to the present invention.

Such additives can be any materials inducing a range of interactions between the poly(organophosphazene)s and the physiologically active substances, and at least one selected from the group consisting of neutral, cationic, or anionic polymers with the weight-average molecular weight of 200 to 750,000, amino acids, peptides, proteins, fatty acids, phospholipids, vitamins, drugs, poly(ethyleneglycol) esters, steroids, amine compounds, acrylic copolymers, organic solvents, preservatives, sugars, polyols, sugar-containing polyols, sugar-containing amino acids, surfactants, sugar-containing ions, silicates, metal salts, and ammonium salts.

More specifically, the additives can be at least one selected from the group consisting of neutral polymers (for example, having the weight-average molecular weight of 200 to 750,000) such as poly(ethyleneglycol) and poly (vinyl pyrrolidone); cationic polymers (for example having the weight-average molecular weight of 200 to 750,000) such as poly-$_L$-arginine, poly-$_L$-lysine, polyethylenimine, chitosan, protamine, and the like; anionic polymers (for example, having the weight-average molecular weight of 200 to 750,000) such as polyvinylacetate (PVA), hyaluronic acid, chondroitin sulphate, dextran sulfate, heparin, alginate, sodium carboxymethyl cellulose and the like; amiloride, procainamide, acetyl-beta-methylcholine, spermine, spermidine, lysozyme, fibroin, albumin, collagen, growth factors such as transforming growth factor-beta (TGF-beta), fibroblast growth factor (bFGF), and vascular endothelial growth factor (VEGF), proteins such as bone morphogenetic proteins (BMPs), dexamethason, fibronectin, fibrinogen, and thrombin, dexrazoxane, leucovorin, ricinoleic acid, phospholipid, small intestinal submucosa, vitamin E, polyglycerol ester of fatty acids, labrafil, labrafil M1944CS, cardioxane, glutamic acid, hydroxypropyl methylcellulose, gelatin, isopropyl myristate, eudragit, tego betain, dimyristoylphosphatidylcholine, scleroglucan, demineralized bone matrix (DBM), biomaterials; an organic solvent such as chromophore EL, ethanol, dimethyl sulfoxide; preservatives such as methylparaben: sugars such as starch, cyclodextrin and its derivatives, lactose, glucose, dextran, mannose, sucrose, trehalose, maltose, and ficoll; polyols such as innositol, mannitol, and sorbitol; sugar-containing polyols such as sucrose-mannitol, and glucose-mannitoal; amino acids such as alanine, arginine, glycine; polymer-containing polyols including trehalose-PEG, sucrose-PEG, and sucrose-dextran; sugar-containing amino acids such as sorbitol-glycine, and sucrose-glycine; poloxamer of various molecular weights, surfactants such as tween 20, tween 80, triton X-100, sodium dpdecyl sulfate (SDS), and Brij; sugar-containing ions including trehalose-$ZnSO_4$, and maltose-$ZnSO_4$; and salts such as silicates, NaCl, KCl, NaBr, NaI, LiCl, n-$Bu_4NBr$, n-$Pr_4NBr$, $Et_4NBr$, $Mg(OH)_2$, $Ca(OH)_2$, $CaHPO_4$, $Ca_3(PO_4)_2$, $Ca_4(PO_4)_2O$, $Ca_5(PO_4)_3(OH)$, $ZnCO_3$, $Ca_3(PO_4)_2$, $ZnCl_2$, $Zn(O_2CCH_3)_2$ $(C_2H_3O_2)_2Zn$, $ZnCO_3$, $CdCl_2$, $HgCl_2$, $CoCl_2$, $(CaNO_3)_2$, $BaCl_2$, $MgCl_2$, $PbCl_2$, $AlCl_3$, $FeCl_2$, $FeCl_3$, $NiCl_2$, $AgCl$, $AuCl_3$, $CuCl_2$, sodium dodecyl sulphate, sodium tetradecyl sulphate, dodecyltrimethylammonium bromide, dodecyltrimethylammonium chloride, and tetradecyltrimethylammonium bromide.

According to the present invention, biomaterials such as materials for plastic surgery and orthopedics including a filler, tissue engineering biomaterials including artificial cartilage, dental materials, materials for preventing stenosis including stent, adhesion barriers, and vasoocclusion materials and/or a delivery composition for the physiologically active substances is in a sol-phase of a liquid state at room temperature due to the sol-gel behavior by the crosslinkings of the poly(organophosphazene) as contained and the sol-gel behavior by the temperature change. Therefore, they are readily injected via various routes such as an injection. Also, when being injected to a body, they turn into a gel phase at a body temperature and have an enhanced solidity thanks to the crosslinkings of the hydrogel so that they have an excellent applicability for a wide range of biomaterials as previously enumerated. Also, the polymer can be crosslinked after the physiologically active substances with various functional groups are directly introduced therein and thus its functionality and biocompatibility as a biomaterial can be further improved. The hydrogels of the present invention can be injected into the body by any administration method such as oral administration, buccal administration, mucosal administration, intranasal administration, intraperitoneal administration, a hypodermic injection, an intramuscular injection, transdermal administration, intraarticular administration, intravascular administration, intratumor administration, or other administration to a required site. In particular, preference is made for local administration such as a hypodermic injection, an intramuscular injection, transdermal administration, intraarticular administration, or intratumor administration.

In accordance with the present invention, depending on the types of the substituents and the composition ratio, the crosslinkable poly(organophosphazene)s and the poly(organophosphazene) solution (the hydrogel) comprising the same can be changed into a gel phase not only by a temperature change but also by the UV irradiation and/or the addition of the crosslinkers and/or the addition of the additive and/or the addition of the enzyme, and/or the formation of the crosslinkings between the substituents of the phosphazene polymer. Therefore, their sol-gel behavior and their gel properties can be easily controlled so that they can be utilized for many industrial uses.

In another embodiment, the present invention provides a process for preparing a poly(organophosphazene) with physiologically active substances covalently-bonded thereto, which has Chemical Formula 1 and can be chemically-crosslinked by the UV irradiation and/or the addition of the crosslinkers and/or the addition of the enzymes and/or the addition of the additives, and/or the mixing with the chemically-crosslinkable poly(organophosphazene)s. The preparation process of the present invention may comprise the following steps:

(1) carrying out either a thermal polymerization with a phosphazene trimer of Chemical Formula 2, or a cationic polymerization or other conventional polymerization with phosphoranamine to give dichlorophosphazene linear polymers of Chemical Formula 3;

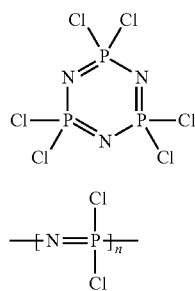

[Chemical Formula 2]

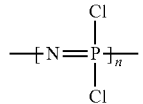

[Chemical Formula 3]

(where, n ranges from 1 to 100000)

(2) subjecting the compound of Chemical Formula 3 prepared in Step (1) to a reaction with an amino acid ester represented by Chemical Formula 4 or a salt thereof;

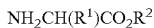  $NH_2CH(R^1)CO_2R^2$  [Chemical Formula 4]

(3) subjecting the product of Step (2) to a reaction with an amino acid, a peptide, or a depsipeptide ester represented by Chemical Formula 5, or a salt thereof;

$NH_2(R^3)(R^4)(R^5)$  [Chemical Formula 5]

(4) subjecting the product of Step (2) or Step (3) to a reaction with a substituent having a crosslinkable functional group represented by Chemical Formula 6 or a salt thereof;

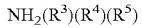  $NH_2(R^6)$ or $OH(R^6)$  [Chemical Formula 6]

(5) subjecting the product of Step (3) or Step (4) to a reaction with a substituent having a functional group represented by Chemical Formula 7 or a salt thereof;

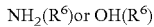  $NH_2(R^7)(R^8)(R^9)$  [Chemical Formula 7]

(6) subjecting the product of Step (4) or Step (5) to a reaction with aminomethoxy polyethyleneglycol of Chemical Formula 8 or a salt thereof;

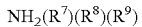  $NH_2(CH_2CH_2O)_pCH_3$  [Chemical Formula 8]

(7) subjecting the compound obtained as above to a reaction with a compound having a thiol group, a vinyl group, tyramine, tyrosine, and a phenyl derivative which is selected either from the group consisting of an acrylate compound, a methacrylate compound, an acrylamide compound, a vinylsulfone compound, a thiol compound, a cysteine compound, a cisteamine compound, a mercaptic acid compound, an allyl pyrimidine compound, and a compound belonging to one of the foregoing compounds and having a thiol- or vinyl-group protected with a protecting group, or from the group consisting of a tyramine compound, a tyrosine compound, and a phenyl derivative; and (8) covalently-bonding at least one physiologically active substance selected from the group consisting of a protein, a polypeptide, a peptide, a fusion protein, an antibody, a hormone, a vaccine, a gene, an anticancer drug, and an angiogenesis inhibitor having various functional groups such as a hydroxyl group, an amide group, an amino group, a carboxyl group, a thiol group, a vinyl group, an aldehyde group, a halogen group, or a keton group to a functional group of at least one of $R^6$, $R^9$, and $R^{10}$ of the product as obtained above selected from the group consisting of a hydroxyl group, an amide group, an amino group, a carboxylic group, a thiol group, and a vinyl group.

Among the above steps, Step (4) or Step (5) and Step (6) can be carried out in a different order.

When $R^9$ in Chemical Formula 7 is selected from the group consisting of $CH_2C_6H_5$, $CH_2CHCH_2$, OH or a protecting group, the preparation process according to the present invention may further comprise a step for obtaining a poly(organophosphazene) whose $R^9$ has a hydrogen (H) functional group or various functional groups [Step (6-1)], wherein the polymer prepared in Step (6) is subjected to a dehydrogen reaction (when $R^9$ is $CH_2C_6H_5$), a de-allylesterification reaction (when $R^9$ is $CH_2CHCH_2$), a deprotecting reaction or an esterification reaction.

In addition, the present invention may comprise Step (6-2) for preparing a poly(organophosphazene) whose $R^9$ have various functional groups such as $NHCH(SH)CO_2H$, $NH(CH_2)_qSH$, $NH(CH_2CH_2NH)_rH$, $[NH(CH_2)_4CH(NH_2)CO]_rOH$, $[NHC(=NH)(CH_2)_3CH(NH_2)CO]_rOH$, folic acid, hyaluronic acid, cyclodextrin, an imidazole compound, histidine, lysine, arginine, cysteine, thioalkyl amine, spermine, spermidine, various molecular weights of polyethyleneimine, polyhistidine, polylysine, polyarginine, heparin, chitosan, protamine, or the like. In this step, the product of Step (6) comprising carboxylic acid or the product of Step (6-1) resulting from the dehydrogen reaction, the de-allylesterification reaction, or the esterification reaction is subjected to a reaction with a compound having a functional group such as folic acid, hyaluronic acid, cyclodextrin, an imidazole compound, histidine, lysine, arginine, cysteine, thioalkyl amine, spermine, spermidine, various molecular weights of polyethyleneimine, polyhistidine, polylysine, polyarginine, heparin, chitosan, protamine, or the like.

As $R^{10}$, a functional group capable of triggering crosslinking by UV irradiation and/or addition of the crosslinker and/or addition of the additives and/or addition of the enzyme and/or the mixing with a poly(organophosphazene)s, the poly(organophosphazene)s having various functional groups prepared from Step (6), Step (6-1) or Step (6-2) are also subjected to a reaction either with a compound having a thiol- or vinyl-group or a compound belonging to the aforementioned compound and having a thiol- or vinyl-group protected by a protection group including an acrylate compound, a methacrylate compound, an acrylamide compounds, a vinyl sulfone compound, a thiol compound, a cysteine compound, a cysteamine compound, a mercaptic acid compound, an ally pyrimidine compound, and a compound belonging to one of the foregoing compounds and having the thiol- or vinyl-group protected by a protection group, or with a compound having tyrosine, tyramine, or a phenyl derivative. As a result of this, one can obtain the poly(organophosphazene) with a crosslinkable functional group directly attached thereto through a chemical bond [Step (7)].

Step (4) and/or Step (7) may further comprise adding a polymerization inhibitor in an amount of $10^{-4}$ to $10^{-2}\%$ by weight based on the total weight of the reactant for the corresponding step.

If $R^6$ and/or $R^{10}$ is (are) protected with a protection group in Chemical Formula 6 or in Step (7), the preparation process of the present invention can further comprise a step for deprotecting the polymers obtained from Step (7) to obtain a poly(organophosphazene) whose $R^6$ and $R^{10}$ have a thiol group or various vinyl groups [Step (7-1)].

Also, in Step (4), Step (5), Step (6), Step (6-1), Step (6-2), Step (7), or Step (7-1), if $R^6$, $R^9$, and $R^{10}$ has a range of functional groups such as a hydroxyl, an amide, an amino, a thiol, or a carboxylic, a thiol, or a vinyl group, one can further include a step of covalently-bonding to the polymers prepared from those steps the physiologically active substance with various functional groups, for example a protein, a polypeptide, a peptide, an antibody, a hormone, a vaccine, a gene, an anticancer drug, or an angiogenesis inhibitor having various functional groups such as a hydroxyl, an amide, an amino, a carboxylic, a thiol, a vinyl, an aldehyde, a halogen, or a ketone [Step (8)].

The process for preparing the crosslinkable poly(organophosphazene) of Chemical Formula 1 can be summarized as in the following Reaction Scheme 1:

thereof in the presence of 4 equiv. of triethylamine. Preferably, the salt of Chemical Formula 4 is a hydrogen chloride salt or a sulfuric acid salt. As a reaction solvent, one can use tetrahydrofuran (THF), dioxane, chloroform, or toluene, but the present invention is not limited thereto. The reaction can be carried out at a temperature of −60 to 50° C. for about 8 to 72 hours.

Step (3) can be carried out by subjecting the product from Step (2) to a reaction with 0 to 1.9 equiv. of an amino acid, a peptide, or a depsipeptide ester represented by Chemical Formula 5, or a salt thereof in the presence of 4 equiv. of triethylamine. Preferably, the salt of the compound of Chemical Formula 5 is an oxalate, a hydrogen chloride salt, or a trifluoric acid salt. As a reaction solvent, one can use acetonitrile, tetrahydrofuran, dioxane, chloroform, or toluene, but the present invention is not limited thereto. Preferably, the reaction temperature is 0 to 50° C. and the reaction may take about 1 to 72 hours.

Step (4) can be carried out by subjecting the product from Step (3) to a reaction with 0.01 to 1.9 equiv. of a substituent having a crosslinkable functional group represented by Chemical Formula 6, or a salt thereof in the presence of 4 equiv. of triethylamine. Preferably, the salt of the compound of Chemical Formula 6 may be an oxalate, a hydrogen chlo-

[Reaction Scheme 1]

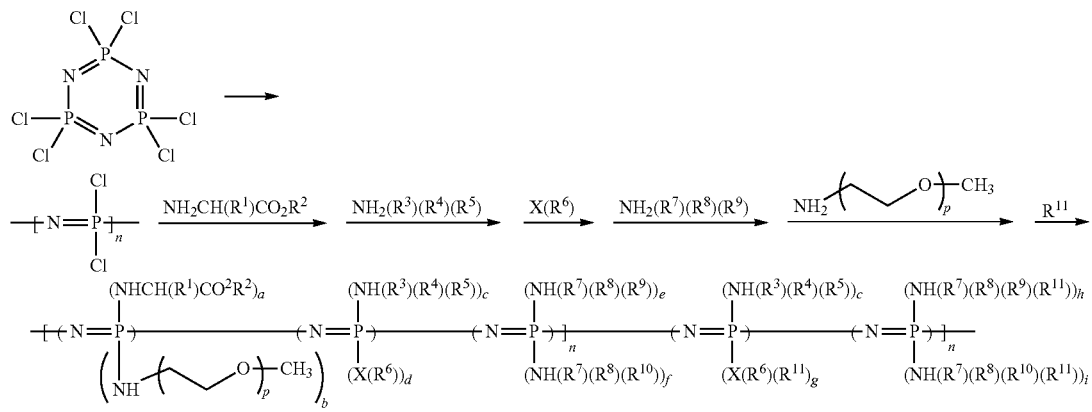

In the above Formulae 4, 5, 6 and 7 and in Reaction Scheme 1, $R^1$, $R^2$, $R^3$, $R^4$, $R^5$, $R^6$, $R^7$, $R^8$, $R^9$, $R^{10}$, $R^{11}$, a, b, c, d, e, f, g, h, i, n, and p are the same as defined in the compound of Chemical Formula 1.

Hereinafter, methods of preparing a chemically-crosslinkable poly(organophosphazene) with a physiologically active substance covalently-bonded thereto as represented by Chemical Formula 1 of the present invention will be described in more detail. In order to prevent moisture from being introduced, a vacuum and/or nitrogen line is preferably used during all of the preparation process. All sorts of solvents used in the reactions are sufficiently dried according to a typical method.

Step (1) can be carried out by placing the compound of Chemical Formula 2 and 0.1 to 10 wt % of $AlCl_3$ in a glass reactor tube, and sealing and reacting the same at 200 to 250° C. for 4 to 8 hours while rotating it at a rate of one cycle per a minute.

Step (2) can be carried out by subjecting one equiv. of the product from Step (1) to a reaction with 0.01-1.9 equiv. of the amino acid ester represented by Chemical Formula 4 or a salt ride salt, or a trifluoric acid salt. Preferably, the reaction temperature is 25 to 50° C. and the reaction may take about 12 to 72 hours.

Step (5) can be carried out by subjecting the product of Step (3) and the product of Step (4) to a reaction with 0.01 to 1.9 equiv. of a substituent having a functional group represented by Chemical Formula 7, or a salt thereof in the present of 4 equiv. of triethylamine. Preferably, the salt of the compound of Chemical Formula 7 is an oxalate, a hydrogen chloride salt, or a trifluoric acid salt. As a reaction solvent, one can use acetonitrile, tetrahydrofuran, dioxane, chloroform, or toluene, but the present invention is not limited thereto. In order to sufficiently proceed with the reaction and to properly inhibit polymerization, the reaction temperature is preferably from 25 to 50° C. and the reaction may take about 12 to 72 hours.

In Step (6), the product of Step (4) or Step (5) and 2 equiv. (based on the remaining chlorine in the product) of an aminomethoxy polyethylene glycol of Chemical Formula 8 react in the presence of 4 equiv. of triethylamine to substitute all the remaining chlorine groups in the products of Step (4) or Step (5). As a reaction solvent, one can use at least one selected from the group consisting of tetrahydrofuran, dioxane, chloroform, and toluene, but the present invention is not limited thereto. Preferably, the reaction temperature is 25 to 50° C. and the reaction may take about 24 to 72 hours.

Among these steps, Step (4) or Step (5) and Step (6) can be carried out in a different order.

When $R^9$ is $CH_2C_6H_5$ in Chemical Formula 7, Step (6-1) is carried out by subjecting the product of Step (6) to a dehydrogenation reaction with palladium/charcoal or palladium black (50-90% by weight of the product of Step (6)) in the presence of 30-80 psi of a hydrogen gas to make a substitution to a carboxylic group. As a reaction solvent, one can use methyl alcohol and/or ethyl alcohol, but the present invention is not limited thereto. Preferably, the reaction temperature is 10 to 35° C. and the reaction can take about 1 to 24 hours. Also, when $R^9$ is $CH_2CHCH_2$ in Chemical Formula 7, it is carried out by subjecting the reaction product of Step (6) to a de-allylesterification reaction with 10-20 mol % of tetrakistriphenylphosphine palladium(0) in the presence of 10-20 equiv. of morpholine to make a substitution to a carboxylic group. As a reaction solvent, one can use at least one selected from the group consisting of tetrahydrofurane, dioxane, chloroform, and toluene, but the present invention is not limited thereto. Preferably, the reaction temperature is 0 to 25° C. and the reaction can take about 1 to 24 hours. When $R^9$ is OH in Chemical Formula 7, it is carried out by subjecting the product of Step (5) to an esterification reaction with 1 to 5 times by mole of a cyclic anhydride in the presence of 1 to 5 times by mole of 4-methylamino pyridine to make a substitution to a carboxylic group. The cyclic anhydride may be any of typically available cyclic anhydrides. For example, it may be at least one selected from the group consisting of succinic anhydride, maleic anhydride, 2,3-dichloromaleic anhydride, tetrafluorosuccinic anhydride, diglycolic anhydride, citraconic anhydride, itaconic anhydride, glutaric anhydride, adipic anhydride, cis-aconitic anhydride, dimethylmaleic anhydride, 1-cyclopentene-1,2-dicarboxylic anhydride, phthalic anhydride, 3,6-dichlorophthalic anhydride, 3-fluorophthalic anhydride, 4-fluorophthalic anhydride, 3-nitrophthalic anhydride, 4-nitrophthalic anhydride, 3-hydroxyphthalic anhydride, isatoic anhydride, and the like, but the present invention is not limited thereto. The cyclic anhydride refers to all types of cyclic anhydrides. The reaction solvent available in this step comprise, but are not limited to, tetrahydrofuran and dioxane. Preferably, the reaction temperature is 20 to 50° C. and the reaction can take about 1 to 48 hours.

In Step (6-2), the product of Step (6) or Step (6-1) including carboxylic acid is reacted with folic acid, hyaluronic acid, cyclodextrin, an imidazole compound, histidine, lysine, arginine, cysteine, thiol alkylamine, spermine, spermidine, or various molecular weights of polyethyleneimine, polyhistidine, polylysine, polyarginine, heparin, chitosan, or protamine in the presence of 1 to 3 equiv. of dicyclohexyl carbodiimide and 1 to 3 equiv. of hydroxyl succinimide to yield a poly(organophosphazene) having various functional groups. As a reaction solvent, one can use tetrahydrofuran and/or chloroform, but the present invention is not limited thereto. Preferably, the reaction temperature is 0 to 25° C. and the reaction may take about 1 to 48 hours.

In Step (7), the substituents having a crosslinkable, functional groups and the product of Step (6), Step (6-1), or Step (6-2) having various functional groups can be linked to the poly(organophosphazene) through a disulfide bond [Int. J. Cancer, 73, 859-864 1997], a carbamite bond [I. Biochem. Pharmacol, 34, 289 1985], or a hydrazone bond [J. Control Release, 73, 89-102 2001].

Also, when $R^6$ and $R^{10}$ is a group consisting of protecting groups in Step (6) and Step (7), Step (7-1) is carried out by subjecting the polymer obtained from Step (6) and Step (7) to a deprotection reaction, allowing $R^6$ and $R^{10}$ to have a thiol functional group or various vinyl functional groups.

When $R^6$, $R^9$, and $R^{10}$ in Step (5), Step (6), Step (6-1), Step (6-2), Step (7), and Step (7-1) have various functional groups such as a hydroxyl, an amide, an amino, a carboxylic, a thiol, or a vinyl groups, Step (8) can be carried out by further subjecting the polymers prepared from those steps to a reaction for forming covalent bonds with physiologically active substances having a range of functional groups such as a protein, a polypeptide, a peptide, a fusion protein, an antibody, a hormone, a vaccine, a gene, an anticancer drug, or an angiogenesis inhibitor having various functional groups such as a hydroxyl, an amide, an amino, a carboxylic, a thiol, a vinyl, an aldehyde, a halogen, or a ketone groups to, allowing them to have a range of physiologically active functions.

In Step (4) and/or Step (7), polymerization inhibitors may be added in an amount of $10^{-4}$ to $10^{-2}$% by weight based on the total weight of the reactants for a corresponding step. During a synthesis process, an elevated temperature and exposure to UV may cause the vinyl compounds crosslinkable by UV irradiation to go through a crosslinking reaction prior to the formation of a desired crosslinkings and thus unintentional crosslinkings between the polymers can be produced before obtaining a final product. The polymerization inhibitor plays a role to suppress a spontaneous crosslinking reaction between the polymers before such crosslinking reactions. The amount of the polymerization inhibitor is determined at a proper amount for suppressing the crosslinking while having no effect on the synthesis reaction. The polymerization inhibitor can be any of typically available materials, and for example, at least one selected from the group consisting of nitrobenzene, 1,3,5-trinitrobenzenebenzene, p-benzoquinone, chloranil, 1,1-diphenyl-2-picrylhydrazyl, ferric chloride, copper chloride, oxygen, sulfur, aniline, phenol, p-dihydroxybenzene, 1,2,3-trihydroxybenzene, 2,4,6-trimethylphenol, monomethyl ether hydroquinone, methoxy hydroquinone, 2,2-diphenyl-1-picrylhydrazyl, 2,2-di(4-tert-octylphenyl)-1-picrylhydrazyl, 3-carboxyl-proxyl, 3-cyanoproxy(, 3-(2-iodoacetylamido)-proxyl, 3-maleimido-proxyl, garbinoxyl, 2,2,3,4,5,5-hexamethyl-3-imidazolinium-1-yloxy methyl sulfate, 4-(1-hydroxy-1-methylethyl)-2,2,5,5-tetramethyl-3-imidazolinium-1-yloxy, 4-phenacylidene-2,2, 5,5-tetramethylimidazolidin-1-yloxy, 4-phenyl-2,2,5,5-tetramethyl-3-imidazolin-1-yloxy, tris (4-bromophenyl) ammoniumyl hexachloroantimonate, 3β-DOXYL-5α-cholestane, 5-DOXYL-stearic acid, 16-DOXYL-stearic acid, methyl 5-DOXYL-stearate, 4-acetamido-TEMPO, 4-acetamido-2,2,6,6-tetramethylpiperidine 1-oxyl purum, 4-(2-bromoacetamido)-TEMPO, 4-carboxyl-TEMPO, 4-carboxyl-2, 2,6,6-tetramethylpiperidine 1-oxyl, 4-(2-chloroacetamido)-2,2,6,6-tetramethylpiperidine 1-oxyl purum, 4-cyano-TEMPO, 4-hydroxy-TEMPO purum, 4-hydroxy-TEMPO benzoate, 4-(2-idoacetylamido)-TEMPO, 4-maleimido-TEMPO, 4-methoxy-TEMPO97, 4-oxo-TEMPO, TEMPO, 4-isothiocyanato-2,2,6,6-tetramethylpiperidine 1-oxyl purum, 2,2,6,6-tetramethyl-4-(methylsulfonyloxy)-1-piperidinoxy, and 2,2,6,6-tetramethylpiperidine 1-oxyl purum, but the present invention is not limited thereto. As a reaction solvent, one can use at least one selected from the group consisting of acetonitrile, tetrahydrofuran, dioxane, chloroform, and toluene.

In Steps (1) to (6), the product obtained from each step may be used for a reaction in a subsequent step without purification. A pure target product from the reaction products of Step (6), Step (7), Step (7-1) and Step (8) can be recovered by the purification process that will be described below.

First, the reaction mixture is centrifuged or filtered to remove the precipitates (for example, triethylammonium chloride, a triethyl ammonium salt of oxalic acid and the like) therefrom, and the filtrate is concentrated under a reduced pressure until a small amount of the solvent is remained. The resulting concentrate is dissolved in tetrahydrofuran, and is added with an excessive amount of ethylether, hexane or a mixed solvent thereof to precipitate the products and filter the same. This process is repeated for 2 to 3 times to remove unreacted substituents. The resulting compound therefrom is dissolved again in a small amount of methanol or ethanol and subjected to dialysis using methanol or ethanol at 25° C. for 3-10 days and to dialysis using distilled water at 4-25° C. for 3-10 days. Then, it is subjected to freeze-drying to give a pure compound of Chemical Formula 1.

In still other embodiment, the present invention provides a process for preparing a hydrogel which comprises the steps of:

preparing a solution of at least one poly(organophosphazene) of Chemical Formula 1 as described above; and forming chemical crosslinkings in the polymer as prepared.

The formation of chemical crosslinkings can be carried out by at least one of five methods as follows:
1) mixing a solution of poly(organophosphazene) having a thiol substituent and a solution of poly(organophosphazene) having a vinyl substituent;
2) UV irradiation;
3) addition of a crosslinker;
4) addition of an additive; and
5) addition of an enzyme.

When the chemical crosslinkings are formed by mixing a solution of the poly(organophosphazene) having a thiol substituent and a solution of the phosphazene polymer having a vinyl substitution, the solution of at least one poly(organophosphazene) of Chemical Formula 1 wherein $R^6$ and/or $R^{10}$ is a thiol substituent and the solution of at least one poly (organophosphazene) of Chemical Formula 1 wherein $R^6$ and/or $R^{10}$ is a vinyl substituent can be mixed to form chemical crosslinkings through Michael Addition between the thiol group and the vinyl group or between the vinyl groups. At this time, a further treatment with at least one photoinitiators and/or at least one crosslinker and/or at least one additive can aid or promote the formation of the crosslinkings.

Also, when the chemical crosslinkings are formed by UV irradiation, the hydrogel can comprise a solution of at least one poly(organophosphazene) of Chemical Formula 1 and a photoinitiator. The photoinitiator can be included in an amount of $1 \times 10^{-6}$ to 10% by weight, preferably $1 \times 10^{-3}$ to 1% by weight based on the total weight of the poly(organophosphazene). If the amount of photoinitiator is less than the foregoing range, desired effects from the photoinitiator may not be obtained. On the other hand, if the amount exceeds the foregoing range, it may disadvantageously have an effect on the efficacy of active ingredients and/or the properties of the polymers showing the sol-gel behavior according to the present invention.

Photoinitiators available for the present invention can be any compounds capable of forming a radical by light-irradiation, and for example, at least one selected from the group consisting of ketone compounds, phosphine oxide compounds, alkylester compounds, benzoyl compounds, titanium salt, iodonium salts, dibenzoyl compounds, thiocarbonate compounds, dion compounds, and potassium sulfates, the specific types of which are the same as described above.

In addition, when the chemical crosslinkings are formed by the crosslinker, the hydrogel of the present invention comprises at least one poly(organophosphazene) of Chemical Formula 1 and at least one crosslinker selected from the group consisting of a thiol-based crosslinker and a vinyl-based crosslinker. The thiol- or vinyl-based crosslinker is a compound having two or more thiol- and/or vinyl-groups capable of forming chemical crosslinkings by inducing Michael Addition with a thiol- or vinyl group in the poly(organophosphazene). The crosslinker can be used in an amount of $1 \times 10^{-6}$ to 30% by weight, preferably $1 \times 10^{-3}$ to 10% by weight based on the total weight of the poly(organophosphazene)s. If the amount of the crosslinker is below the foregoing range, one cannot obtain a desired effect thereof; on the other hand, if it is above the foregoing range, it may disadvantageously have an effect on the efficacy of active ingredients and/or the sol-gel behavior properties of the polymers according to the present invention.

Suitable crosslinkers for use in the present invention can be any one capable of triggering Michael Addition with a thiol group and/or a vinyl group of the Chemical Formula 1. Therefore, one can use any compound having a thiol group or any compound having two or more vinyl groups. For example, one can use at least one selected from the group consisting of a compound having a thiol group such as a thiol compound, a dithiol compound, and a mercapto compound; and a compound having a vinyl group such as a sulfur-containing amino acid, a sulfur-containing oligopeptide, an acrylate compound, a diacrylate compound, a triacrylate compound, a tetraacrylate compound, a pentaacrylate compound, a hexaacrylate compound, a methacrylate compound, a dimethacrylate compound, a (di)vinyl compound, a protoporphyrin compound, a (di)vinyl-polyethyleneglycol compound, a (di)vinylsulfone-polyethyleneglycol compound, a diol compound and the like. Specific types of the available crosslinkers are the same as described above.

Also, when the chemical crosslinkings are formed by the additives, the hydrogel of the present invention can comprise a mixture of at least one poly(organophosphazene) of Chemical Formula 1 having a thiol group and at least one poly (organophosphazene) having a vinyl group or at least one poly(organophosphazene) having a thiol group and an additive capable of regulating pH and/or at least one additive selected from the groups of the catalysts. The additive is any catalyst or any additive that can regulate pH into a weak base and it can induce Michael Addition with a thiol group or a vinyl group in the poly(organophosphazene)s or induce a formation of disulfide bond between the thiol groups so as to form the chemical crosslinkings. The content of the additives can range from $1 \times 10^{-6}$ to 30%, preferably $1 \times 10^{-3}$ to 10% by weight based on the total weight of the poly(organophosphazene)s. If the content of the additives is below the foregoing range, one cannot obtain a desired effect thereof; on the other hand, if it is above the foregoing range, it may disadvantageously have an effect on the efficacy of active ingredients and/or the sol-gel behavior properties of the polymers according to the present invention.

The additives that can be used in the present invention comprise any one promoting the formation of crosslinkings either between a thiol group and a vinyl group or between the thiol groups in Chemical Formula 1. For example, one can use a compound of changing the pH into a weak base such as sodium hydroxide, ammonia, potassium hydroxide, triethyl amine, sodium phosphate, trisbase, and HEPES and/or a catalyst such as hydrogen peroxide, and ammonium peroxide, and/or an organic solvent such as DMSO.

Also, when the crosslinkings are formed by the enzymes, the hydrogel of the present invention can include at least one poly(organophosphazene) of Chemical Formula 1 and hydrogen peroxide and an oxydoreductase enzyme. The oxydoreductase enzyme refers to all enzymes triggering a enzyme-substrate reaction with tyramine or tyrosine in the poly(organophosphazene) to form enzymatic crosslinkings. For example, it comprises transglutaminase, laccase, bilirubin oxidase (BOD), manganese (II), hematin, horseradish peroxidase, and the like. Preferably, horseradish peroxidase can be used. The content of the enzyme ranges from $1 \times 10^{-6}$ to 200% by weight, preferably $1 \times 10^{-3}$ to 100% by weight based on the total weight of the poly(organophosphazene)s. If the content of the enzyme is below the foregoing range, one cannot obtain a desired effect thereof; on the other hand, if it is above the foregoing range, the enzyme may disadvantageously have an effect on the efficacy of active ingredients and/or the sol-gel behavior properties of the polymers according to the present invention. Therefore, the aforementioned range is desirable.

The crosslinkable poly(organophosphazene) of the present invention not only exhibits the sol-gel behavior through the chemical crosslinking but also possesses thermosensitivity, showing the sol-gel behavior dependant on a temperature change. Therefore, after easily forming a gel with a change in a temperature, it is further subjected to a chemical crosslinking by UV irradiation and/or addition of a crosslinker, and/or addition of an additive, and/or addition of an enzyme, and/or mixing with other poly(organophosphazene)s to develop a gel with a higher level of gel solidity, which can be utilized for a variety of uses such as materials for plastic surgery and orthopedics including a filler, tissue engineering biomaterials including artificial cartilage, dental materials, materials for preventing stenosis including stent, adhesion barriers, vasoocclusion materials, and a delivery system for a physiologically active substance. Also, since one can directly introduce a physiologically active substance having a range of functional groups into the polymer, it is possible to further enhance functionality and biocompatibility depending on the purposes of the biomaterials. In addition, one can freely control the pore sizes of the hydrogel by the chemical crosslinkings so that the hydrogel can carry well a hydrophilic drug and the like, and it can persistently release the drugs. Also, in the present invention, the drugs can be directly linked to the polymers through covalent bonds so that the rate and the period for releasing the drugs are controllable and thus the present invention is very useful for a delivery system for a physiologically active substance such as drugs.

Besides the delivery system for a physiologically active substance such as drugs, the present invention is expected to be widely available for the biomaterials that are required to have a sufficiently high level of gel solidity such as materials for plastic surgery and orthopedics including a filler, tissue engineering biomaterials including artificial cartilage, dental materials, materials for preventing stenosis including stent, an adhesion barrier, vasoocclusion materials, and the like. Also, other than the high level of gel solidity, such crosslinkable hydrogels can have a physiologically active substance with various functional groups depending on a desired biomaterials directly attached to the polymer so that they can be applied as various biomaterials, presenting enhanced functionality and biocompatibility as biomaterials.

EXAMPLE

Figure 1:
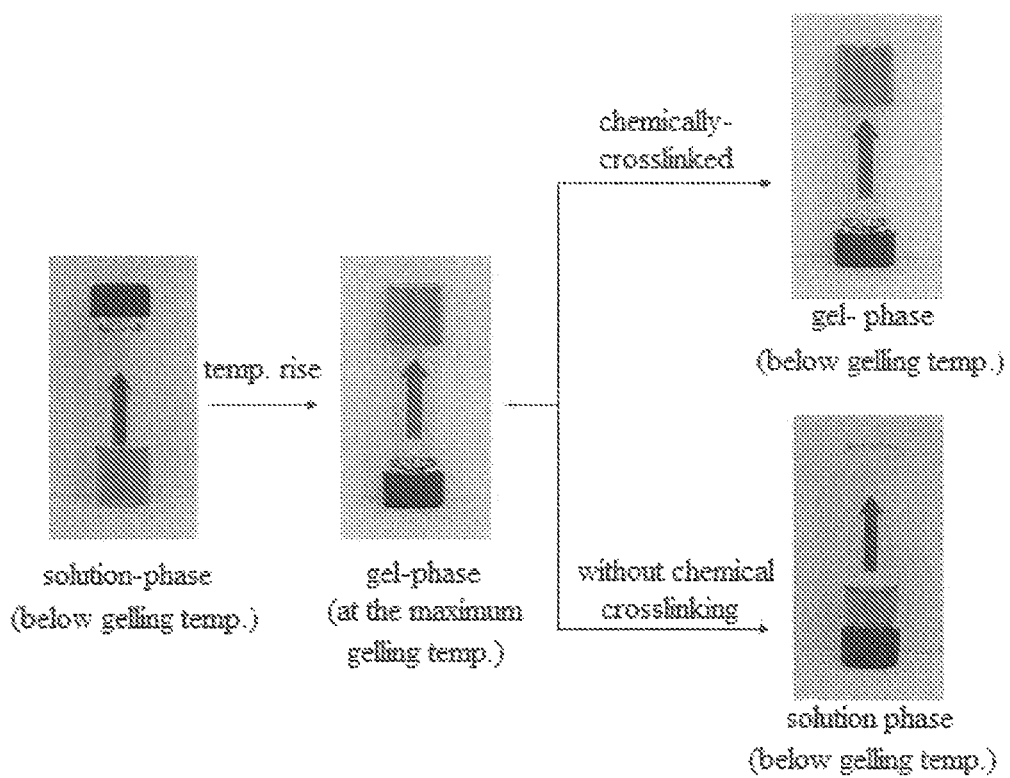
FIG. 1 is a photograph showing sol-gel behavior of the solution of the crosslinkable, thermosensitive poly(organophosphazene) in accordance with an embodiment of the present invention.

Hereinafter, the present invention will be explained in further detail with reference to the following examples. However, it should be understood that these examples are merely illustrative of the present invention and they are not intended to limit the scope of the present invention.

In the following examples, H-NMR and P-NMR spectrums for the product were measured using Varian Gemini-300, respectively and the weight average molecular weight (Mw) was measured by a gel permeation chromatography using a Waters 1515 pump and a 2410 differentiation refractometer. Also, the solidity of the hydrogel prepared by the product was measured by using Brookfield RVDV-III+ viscometer and TA Instruments AR-2000 rheometer.

Example 1

Preparation of Poly[(isoleucine ethylester)(aminomethoxy polyethyleneglycol 550)(aminoethylmethaerylate)phosphazene], $[NP(IleOEt)_{1.01}(AM\text{-}PEG550)_{0.64}(AEMA)_{0.35}]_n$ 3.00 g (15.54 mmol) of a dried isoleucine ethyl ester hydrogen chloride salt was dissolved in 100 ml of anhydrous tetrahydrofuran, and then 4.65 g (46.03 mmol) of triethylamine was added thereto. To this solution was added dropwise 2.00 g (17.26 mmol) of poly(dichlorophosphazene) dissolved in 50 ml of anhydrous tetrahydrofuran, in a dry ice-acetone bath at −60° C., and then the mixture was warmed to room temperature to react for 48 hours.

After checking the progress of the reaction by $^{31}$P-NMR, the solution prepared by dissolving 4.03 g (7.32 mmol) of a dried aminomethoxy polyethylene glycol having the weight-average molecular weight of 550 and 3.63 g (21.98 mmol) of triethylamine in 50 ml of anhydrous tetrahydrofuran was added dropwise to the reaction product, and then the mixture reacted at room temperature for 24 hours and at 40-50° C. for another 24 hours.

After checking the progress of the reaction again by $^{31}$P-NMR, 0.05 g (0.13 mmol) of 2,2-diphenyl-1-picryl-hydrazyl was added to the reaction product in order to inhibit a polymerization reaction at the reaction condition. After a dropwise addition, 3.92 g (23.92 mmol) of a dried 2-ethylamino methacrylate hydrogen chloride salt was dissolved in 10 ml of anhydrous dimethylformamide (DMF) and 6.68 g (47.58 mmol) of triethylamine was added thereto to remove hydrogen chloride salts therefrom, and then the resulting mixture was added to the reaction product to react at room temperature for 24 hours and at 40-50° C. for another 24 hours.

The reaction solution was filtered to remove the triethylamine hydrochloride salt as generated and the filtrate was concentrated under a reduced pressure until a small amount of solvent remained. The concentrate was dissolved in 10 ml of tetrahydrofuran and an excess amount of hexane was added thereto to induce a precipitation. After this procedure was repeated 2 to 3 times, the resulting precipitate was dissolved again in a small amount of methyl alcohol and it was put into an MWCO 12000 membrane (Spectrum Laboratories, Inc.), subjected to a dialysis with methyl alcohol at room temperature for 5 days and then to a dialysis with distilled water for 5 days, and dried at a low temperature to give 7.64 g of poly (dichlorophosphazene) polymer, $[NP(IleOEt)_{1.01}(AM\text{-}PEG550)_{0.64}(AEMA)_{0.35}]_n$ (yield: 68%).

Hydrogen Nuclear Magnetic Resonance Spectrum (CDCl$_3$, ppm):

δ 0.8-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$),
δ 1.9 (s, —NHCH$_2$CH$_2$O$_2$C(C$\underline{H_3}$)C=CH$_2$)
δ 3.4 (s, —NH(CH$_2$CH$_2$O)$_{11}$C$\underline{H_3}$),
δ 3.5-3.9 (b, —NH(C$\underline{H_2}$CH$_2$O)$_{11}$CH$_3$, —NHCH(CH(CH$_3$)(CH$_2$CH$_3$))COOC$\underline{H_2}$C$\underline{H_3}$),
δ 4.0-4.4 (b, —NHCH(CH(CH$_3$)(CH$_2$CH$_3$))COOCH$_2$CH$_3$, —NHCH$_2$CH$_2$O$_2$C(CH$_3$)C=CH$_2$),
δ 5.5 (s, —NHC$\underline{H_2}$C$\underline{H_2}$O$_2$C(CH$_3$)C=CH$_2$)
δ 6.1 (s, —NHCH$_2$CH$_2$O$_2$C(CH$_3$)C=C$\underline{H_2}$)

Phosphorus Nuclear Magnetic Resonance Spectrum (CDCl$_3$, ppm): δ 19.7

Average molecular weight (Mw): 530000

Example 2

Preparation of Poly[(isoleucineethylester)(aminomethoxy polyethyleneglycol550)(aminoethylmethacrylate)phosphazene], [NP(IleOEt)$_{1.16}$(AMPEG550)$_{0.60}$(AEMA)$_{0.23}$]$_n$ After 3.92 g (20.02 mmol) of a dried isoleucine ethylester hydrogen chloride salt was dissolved in 100 ml of anhydrous tetrahydrofuran, 6.08 g (60.06 mmol) of triethylamine was added thereto. To this solution was added dropwise 2.00 g (17.26 mmol) of poly(dichloro phosphazene) dissolved in 50 ml of anhydrous tetrahydrofuran, in a dry ice-acetone bath at −60° C., and then was warmed to room temperature to react for 48 hours.

After checking the progress of the reaction by $^{31}$P-NMR, 1.31 g (7.94 mmol) of a dried aminoethyl methacrylate hydrogen chloride salt was dissolved in 50 ml of anhydrous tetrahydrofuran and 2.41 g (23.82 mmol) of triethylamine was added thereto, and then the resulting mixture was added to the reaction product to react for 8 hours. After checking the progress of the reaction again by $^{31}$P-NMR, a solution prepared by dissolving 14.24 g (25.89 mmol) of a dried aminomethoxypolyethylene glycol having the weight-average molecular weight of 550 and 7.86 g (77.67 mmol) of triethylamine in 50 ml of anhydrous tetrahydrofuran was added dropwise to the resulting reaction product and then reacted at room temperature for 24 hours.

The reaction solution was filtered to remove the triethylamine hydrochloride salt as generated and the filtrate was concentrated under a reduced pressure until a small amount of solvent remained. The concentrate was dissolved in 10 ml of tetrahydrofuran and an excess amount of hexane was added thereto to induce a precipitation. After this procedure was repeated 2 to 3 times, the resulting precipitate was dissolved again in a small amount of methyl alcohol. The resulting solution was put into an MWCO 12000 membrane (Spectrum Laboratories, Inc.), subjected to a dialysis with methyl alcohol at room temperature for 5 days and then to a dialysis with distilled water for 5 days, and dried at a low temperature to give 9.32 g of poly(dichlorophosphazene) polymer, [NP(IleOEt)$_{1.16}$(AMPEG550)$_{0.60}$(AEMA)$_{0.23}$]$_n$ (yield: 76%).

Hydrogen Nuclear Magnetic Resonance Spectrum (CDCl$_3$, ppm):

δ 0.8-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$),
δ 1.9 (s, —NHCH$_2$CH$_2$O$_2$C(C$\underline{H_3}$)C=CH$_2$)
δ 3.4 (s, —NH(CH$_2$CH$_2$O)$_{11}$C$\underline{H_3}$),
δ 3.5-3.9 (b, —NH(C$\underline{H_2}$CH$_2$O)$_{11}$CH$_3$, —NHCH(CH(CH$_3$)(CH$_2$CH$_3$))COOC$\underline{H_2}$C$\underline{H_3}$),
δ 4.0-4.4 (b, —NHCH(CH(CH$_3$)(CH$_2$CH$_3$))COOCH$_2$CH$_3$, —NHCH$_2$CH$_2$O$_2$C(CH$_3$)C=CH$_2$),
δ 5.5 (s, —NHC$\underline{H_2}$C$\underline{H_2}$O$_2$C(CH$_3$)C=CH$_2$)
δ 6.1 (s, —NHCH$_2$CH$_2$O$_2$C(CH$_3$)C=C$\underline{H_2}$)

Phosphorus Nuclear Magnetic Resonance Spectrum (CDCl$_3$, ppm): δ 18.6

Average molecular weight (Mw): 45000

Example 3

Preparation of Poly[(isoleucineethylester)(aminomethoxy polyethyleneglycol550)(aminoethylmethacrylate)phosphazene], [NP(IleOEt)$_{1.21}$(AMPEG550)$_{0.57}$(AEMA)$_{0.21}$]$_n$ With the same method as in Example 2, 9.44 g of the end product, [NP(IleOEt)$_{1.21}$(AMPEG550)$_{0.57}$(AEMA)$_{0.21}$]$_n$ was obtained by using 2.00 g (17.26 mmol) of poly(dichlorophosphazene), 4.09 g (20.88 mmol) of isoleucineethylester, 13.53 g (24.60 mmol) of aminomethoxy polyethyleneglycol having the weight-average molecular weight of 550, 1.20 g (7.25 mmol) of aminoethylmethacrylate hydrogen chloride salt, 16.01 g (158.19 mmol) of triethylamine, and 200 ml of tetrahydrofurane. (Yield: 78%)

Hydrogen Nuclear Magnetic Resonance Spectrum (CDCl$_3$, ppm):

δ 0.8-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$),
δ 1.9 (s, —NHCH$_2$CH$_2$O$_2$C(C$\underline{H_3}$)C=CH$_2$)
δ 3.4 (s, —NH(CH$_2$CH$_2$O)$_{11}$C$\underline{H_3}$),
δ 3.5-3.9 (b, —NH(C$\underline{H_2}$CH$_2$O)$_{11}$CH$_3$, —NHCH(CH(CH$_3$)(CH$_2$CH$_3$))COOC$\underline{H_2}$C$\underline{H_3}$),
δ 4.0-4.4 (b, —NHCH(CH(CH$_3$)(CH$_2$CH$_3$))COOCH$_2$CH$_3$, —NHCH$_2$CH$_2$O$_2$C(CH$_3$)C=CH$_2$),
δ 5.5 (s, —NHC$\underline{H_2}$C$\underline{H_2}$O$_2$C(CH$_3$)C=CH$_2$)
δ 6.1 (s, —NHCH$_2$CH$_2$O$_2$C(CH$_3$)C=C$\underline{H_2}$)

Phosphorus Nuclear Magnetic Resonance Spectrum (CDCl$_3$, ppm): δ 17.9

Average molecular weight (Mw): 102000

Example 4

Preparation of Poly[(isoleucineethylester)(aminomethoxy polyethyleneglycol550)(aminoethylmethacrylate)phosphazene], [NP(IleOEt)$_{1.23}$(AMPEG550)$_{0.61}$(AEMA)$_{0.15}$]$_n$ With the same method as in Example 2, 9.77 g of end product, [NP(IleOEt)$_{1.23}$(AMPEG550)$_{0.61}$(AEMA)$_{0.15}$]$_n$ was obtained by using 2.00 g (17.26 mmol) of poly(dichlorophosphazene), 4.15 g (21.23 mmol) of isoleucineethylester, 14.48 g (26.32 mmol) of aminomethoxy polyethyleneglycol having the weight-average molecular weight of 550, 0.86 g (5.18 mmol) of aminoethylmethacrylate hydrogen chloride salt, 16.01 g (158.19 mmol) of triethylamine, and 200 ml of tetrahydrofurane. (Yield: 79%)

Hydrogen Nuclear Magnetic Resonance Spectrum (CDCl$_3$, ppm):

δ 0.8-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$), δ 1.9 (s, —NHCH$_2$CH$_2$O$_2$C(CH$_3$)C=CH$_2$)
δ 3.4 (s, —NH(CH$_2$CH$_2$O)$_{11}$$\underline{CH_3}$),
δ 3.5-3.9 (b, —NH($\underline{CH_2CH_2O}$)$_{11}$CH$_3$, —NHCH(CH(CH$_3$)(CH$_2$CH$_3$))COO$\underline{CH_2CH_3}$),
δ 4.0-4.4 (b, —NHCH(CH(CH$_3$)(CH$_2$CH$_3$))COO$\underline{CH_2}$CH$_3$, —NHCH$_2$CH$_2$O$_2$C(CH$_3$)C=CH$_2$),
δ 5.5 (s, —NH$\underline{CH_2}$CH$_2$O$_2$C(CH$_3$)C=CH$_2$)
δ 6.1 (s, —NHCH$_2$CH$_2$C)$_2$C(CH$_3$)C=$\underline{CH_2}$)

Phosphorus Nuclear Magnetic Resonance Spectrum (CDCl$_3$, ppm): δ 19.9

Average molecular weight (Mw): 132000

Example 5

Preparation of Poly[(isoleucineethylester)(aminomethoxy polyethyleneglycol550)(aminoethylmethacrylate)phosphazene], [NP(IleOEt)$_{1.17}$(AM-PEG550)$_{0.68}$(AEMA)$_{0.14}$]$_n$ With the same method as in Example 2, 10.11 g of the end product, [NP(IleOEt)$_{1.17}$(AMPEG550)$_{0.68}$(AEMA)$_{0.14}$]$_n$ was obtained by using 2.00 g (17.26 mmol) of poly(dichlorophosphazene), 3.94 g (20.19 mmol) of isoleucineethylester, 16.14 g (29.34 mmol) of aminomethoxy polyethyleneglycol having the weight-average molecular weight of 550, 0.80 g (4.83 mmol) of aminoethylmethacrylate hydrogen chloride salt, 16.50 g (163.08 mmol) of triethylamine, and 200 ml of tetrahydrofurane. (Yield: 79%)

Hydrogen Nuclear Magnetic Resonance Spectrum (CDCl$_3$, ppm):
δ 0.8-1.1 (b, —NHCH(CH($\underline{CH_3}$)(CH$_2$CH$_3$))COOCH$_2$CH$_3$),
δ 1.1-1.4 (b, —NHCH(CH(CH$_3$)($\underline{CH_2}$CH$_3$))COOCH$_2$CH$_3$),
δ 1.9 (s, —NHCH$_2$CH$_2$O$_2$C($\underline{CH_3}$)C=CH$_2$)
δ 3.4 (s, —NH(CH$_2$CH$_2$O)$_{11}$$\underline{CH_3}$),
δ 3.5-3.9 (b, —NH($\underline{CH_2CH_2O}$)$_{11}$CH$_3$, NHCH(CH(CH$_3$)(CH$_2$CH$_3$))COO$\underline{CH_2CH_3}$),
δ 4.0-4.4 (b, —NHCH(CH(CH$_3$)(CH$_2$CH$_3$))COO$\underline{CH_2}$CH$_3$, —NHCH$_2$CH$_2$O$_2$C(CH$_3$)C=CH$_2$),
δ 5.5 (s, —NH$\underline{CH_2}$CH$_2$O$_2$C(CH$_3$)C=CH$_2$)
δ 6.1 (s, —NHCH$_2$CH$_2$O$_2$C(CH$_3$)C=$\underline{CH_2}$)

Phosphorus Nuclear Magnetic Resonance Spectrum (CDCl$_3$, ppm): δ 19.8

Average molecular weight (Mw): 287000

Example 6

Preparation of Poly[(isoleucineethylester)(aminomethoxy polyethyleneglycol750)(aminoethylmethacrylate)phosphazene], [NP(IleOEt)$_{1.17}$(AM-PEG750)$_{0.55}$(AEMA)$_{0.28}$]$_n$ With the same method as in Example 2, 11.23 g of the end product, [NP(IleOEt)$_{1.17}$(AMPEG750)$_{0.55}$(AEMA)$_{0.28}$]$_n$ was obtained by using 2.00 g (17.26 mmol) of poly(dichlorophosphazene), 3.95 g (20.19 mmol) of isoleucineethylester, 17.80 g (23.73 mmol) of aminomethoxy polyethyleneglycol having the weight-average molecular weight of 750, 1.60 g (9.67 mmol) of aminoethylmethacrylate hydrogen chloride salt, 16.27 g (160.77 mmol) of triethylamine, and 200 ml of tetrahydrofurane. (Yield: 81%)

Hydrogen Nuclear Magnetic Resonance Spectrum (CDCl$_3$, ppm):
δ 0.8-1.1 (b, —NHCH(CH($\underline{CH_3}$)(CH$_2$CH$_3$)COOCH$_2$CH$_3$),
δ 1.1-1.4 (b, —NHCH(CH(CH$_3$)($\underline{CH_2}$CH$_3$))COOCH$_2$CH$_3$),
δ 1.9 (s, —NHCH$_2$CH$_2$O$_2$C($\underline{CH_3}$)C=CH$_2$)
δ 3.4 (s, —NH(CH$_2$CH$_2$O)$_{15}$$\underline{CH_3}$),
δ 3.5-3.9 (b, —NH($\underline{CH_2CH_2O}$)$_{15}$CH$_3$, —NHCH(CH(CH$_3$)(CH$_2$CH$_3$))COO$\underline{CH_2CH_3}$),
δ 4.0-4.4 (b, —NHCH(CH(CH$_3$)(CH$_2$CH$_3$))COO$\underline{CH_2}$CH$_3$, —NHCH$_2$CH$_2$O$_2$C(CH$_3$)C=CH$_2$),
δ 5.5 (s, —NH$\underline{CH_2}$CH$_2$O$_2$C(CH$_3$)C=CH$_2$)
δ 6.1 (s, —NHCH$_2$CH$_2$O$_2$C(CH$_3$)C=$\underline{CH_2}$)

Phosphorus Nuclear Magnetic Resonance Spectrum (CDCl$_3$, ppm): δ 18.9

Average molecular weight (Mw): 185000

Example 7

Preparation of Poly[(isoleucineethylester)(aminomethoxy polyethyleneglycol550)(hydroxyethylmethacrylate)phosphazene], [NP(IleOEt)$_{1.23}$(AM-PEG550)$_{0.61}$(HEMA)$_{0.15}$]$_n$ With the same method as in Example 2, 9.53 g of the end product, [NP(IleOEt)$_{1.10}$(AMPEG550)$_{0.61}$(HEMA)$_{0.15}$]$_n$ was obtained by using 2.00 g (17.26 mmol) of poly(dichlorophosphazene), 4.15 g (21.23 mmol) of isoleucineethylester hydrogen chloride salt, 0.86 g (5.18 mmol) of hydroxyethyl methacrylate, 14.48 g (26.32 mmol) of aminomethoxy polyethyleneglycol having the weight-average molecular weight of 550, 16.01 g (158.19 mmol) of triethylamine, and 400 ml of tetrahydrofurane. (Yield: 77%)

Hydrogen Nuclear Magnetic Resonance Spectrum (CDCl$_3$, ppm):
δ 0.8-1.1 (b, —NHCH(CH($\underline{CH_3}$)(CH$_2$CH$_3$))COOCH$_2$CH$_3$),
δ 1.1-1.4 (b, —NHCH(CH(CH$_3$)($\underline{CH_2}$CH$_3$))COOCH$_2$CH$_3$),
δ 1.9 (s, —OCH$_2$CH$_2$O$_2$C($\underline{CH_3}$)C=CH$_2$)
δ 3.4 (s, —NH(CH$_2$CH$_2$O)$_{11}$$\underline{CH_3}$),
δ 3.5-3.9 (b, —NH($\underline{CH_2CH_2O}$)$_{11}$CH$_3$, —NHCH(CH(CH$_3$)(CH$_2$CH$_3$))COO$\underline{CH_2CH_3}$),
δ 4.0-4.4 (b, —NHCH(CH(CH$_3$)(CH$_2$CH$_3$))COO$\underline{CH_2}$CH$_3$, OCH$_2$CH$_2$O$_2$C(CH$_3$)C=CH$_2$),
δ 5.4 (s, —O$\underline{CH_2}$CH$_2$O$_2$C(CH$_3$)C=CH$_2$)
δ 6.0 (s, —OCH$_2$CH$_2$O$_2$C(CH$_3$)C=$\underline{CH_2}$)

Phosphorus Nuclear Magnetic Resonance Spectrum (CDCl$_3$, ppm): δ 20.4

Average molecular weight (Mw): 91800

Example 8

Preparation of Poly[(isoleucineethylester)(aminomethoxy polyethyleneglycol750)(hydroxyethylmethacrylate)phosphazene], [NP(IleOEt)$_{1.04}$(AM-PEG750)$_{0.74}$(HEMA)$_{0.22}$]$_n$ With the same method as in Example 2, 12.18 g of the end product, [NP(IleOEt)$_{1.04}$(AMPEG750)$_{0.74}$(HEMA)$_{0.22}$]$_n$ was obtained by using 2.00 g (17.26 mmol) of poly(dichlorophosphazene), 4.09 g (20.88 mmol) of isoleucineethylester hydrogen chloride salt, 0.29 g (1.73 mmol) of hydroxyethylmethacrylate, 23.95 g (31.93 mmol) of aminomethoxy polyethyleneglycol having the weight-average molecular weight of 750, 16.56 g (163.62 mmol) of triethylamine, and 400 ml of tetrahydrofurane. (Yield: 77%)

Hydrogen Nuclear Magnetic Resonance Spectrum (CDCl$_3$, ppm):

δ 0.8-1.1 (b, —NHCH(CH(C$\underline{H_3}$)(CH$_2$C$\underline{H_3}$))COOCH$_2$CH$_3$), δ 1.1-1.4 (b, —NHCH(CH(CH$_3$)(C$\underline{H_2}$CH$_3$))COOCH$_2$CH$_3$), δ 1.9 (s, —OCH$_2$CH$_2$O$_2$C(CH$_3$)C=CH$_2$)

δ 3.4 (s, —NH(CH$_2$CH$_2$O)$\overline{_{15}}$CH$_3$),

δ 3.5-3.9 (b, —N$\overline{H(CH_2CH_2O)}_{15}$CH$_3$, NHCH(CH(CH$_3$)(CH$_2$CH$_3$))COOC$\underline{H_2}$CH$_3$), δ 4.0-4.4 (b, —NHCH(CH(CH$_3$)(CH$_2$CH$_3$))COOC$\underline{H_2}$CH$_3$, —OC$\underline{H_2}$CH$_2$O$_2$C(CH$_3$)C=CH$_2$), δ 5.4 (s, —OCH$_2$CH$_2$O$_2$C(CH$_3$)C=C$\underline{H_2}$)

δ 6.0 (s, —OCH$_2$CH$_2$O$_2$C(CH$_3$)C=C$\underline{H_2}$)

Phosphorus Nuclear Magnetic Resonance Spectrum (CDCl$_3$, ppm): δ 18.1

Average molecular weight (Mw): 101200

Example 9

Preparation of Poly[(isoleucineethylester)(aminomethoxy polyethyleneglycol550)(acrylate)phosphazene], [NP(IleOEt)$_{1.09}$(AMPEG550)$_{0.46}$(Acrylate)$_{0.45}$]$_n$ 6.41 g (32.75 mmol) of a dried isoleucine ethyl ester hydrogen chloride salt was dissolved in 100 ml of anhydrous tetrahydrofuran, and then 9.94 g (98.27 mmol) of triethylamine was added thereto. To this solution was added dropwise 4.00 g (34.48 mmol) of poly(dichloro phosphazene) dissolved in 100 ml of anhydrous tetrahydrofuran, in a dry ice-acetone bath at −60° C., to react for 8 hours and then to further react at room temperature for 48 hours.

After checking the progress of the reaction by $^{31}$P-NMR, a solution prepared by dissolving 7.58 g (13.79 mmol) of a dried aminomethoxy polyethylene glycol having the weight-average molecular weight of 550 and 4.18 g (41.37 mmol) of triethylamine in 50 ml of anhydrous tetrahydrofuran was added dropwise to the reaction product and then reacted at room temperature for 24 hours and at 40-50° C. for another 24 hours.

After checking the progress of the reaction again by $^{31}$P-NMR, a solution prepared by dissolving 4.18 g (67.24 mmol) of a dried amino ethanol in 50 ml of anhydrous tetrahydrofurane and adding 6.80 g (67.24 mmol) of triethylamine thereto was added to the reaction product at 0° C., and reacted at room temperature for 24 hours and at 40-50° C. for another 24 hours.

The reaction solution was filtered to remove triethylamine hydrochloride salt as generated and the reaction filterate was concentrated under a reduced pressure until a small amount of solvent remained. The concentrate was dissolved in 10 ml of tetrahydrofuran and an excess amount of hexane was added thereto to induce a precipitation. After this procedure was repeated 2 to 3 times, the resulting precipitate was dissolved again in a small amount of methyl alcohol, and then was put into an MWCO 12000 membrane (Spectrum Laboratories, Inc.), and subjected to a dialysis with methyl alcohol at room temperature for 5 days and then to a dialysis with distilled water for 5 days, and dried at a low temperature to give 13.84 g of poly(dichlorophosphazene) polymer, [NP(IleOEt)$_{1.01}$(AMPEG550)$_{0.64}$(AEMA)$_{0.35}$]$_n$. (yield: 76%).

13.34 g (26.82 mmol) of the obtained polymer, [NP(IleOEt)$_{1.01}$(AMPEG550)$_{0.64}$(AEMA)$_{0.35}$]$_n$ was dissolved in 300 ml of anhydrous THF and 4.88 g (24.13 mmol) of triethylamine was added thereto and stirred at 0° C. for 15 minutes. To this solution was added each of the solutions prepared by dissolving 7.46 g (36.21 mmol) of dicyclohexylcarbodiimide, 5.31 g (43.45 mmol) of dimethyl aminopyridine, or 2.59 g (36.21 mmol) of acrylic acid in 50 ml of anhydrous tetrahydrofurane, respectively, and then the resulting mixture reacted at room temperature for 48 hours.

The reaction solution was filtered and concentrated under a reduced pressure until a small amount of solvent remained. To the concentrate was added a mixture liquid of chloroform and diethylether (1:1) to induce a precipitation, and dicyclohexyl urea was eliminated by filteration. The filterate was concentrated under a reduced pressure and dissolved in a small amount of methyl alcohol, and then it was put into an MWCO 12000 membrane (Spectrum Laboratories, Inc.), and subjected to a dialysis with methyl alcohol at room temperature for 5 days and then to a dialysis with distilled water for 5 days, and dried at a low temperature to give 13.5 g of poly(dichlorophosphazene) polymer, [NP(IleOEt)$_{1.09}$(AMPEG550)$_{0.46}$(AEMA)$_{0.45}$]$_n$. (Yield: 71%)

Hydrogen Nuclear Magnetic Resonance Spectrum (CDCl$_3$, ppm):

δ 0.91-1.05 (s, —NHCH(CH(C$\underline{H_3}$)(CH$_2$C$\underline{H_3}$))COOCH$_2$CH$_3$), δ 1.05-1.40 (b, —NHCH(CH(CH$_3$)(CH$_2$CH$_3$))COOCH$_2$C$\underline{H_3}$), δ 1.40-1.62 (b, —NHCH(CH(CH$_3$)(C$\underline{H_2}$CH$_3$))COOCH$_2$CH$_3$), δ 1.62-1.85 (b, —NHCH(C$\underline{H}$(CH$_2$CH$_3$))COOCH$_2$CH$_3$), δ 3.38 (s, —NH(CH$_2$CH$_2$O)$\overline{_{11}}$CH$_3$), δ 3.50-3.91 (b, 44H), —NH(C$\underline{H_2}$CH$_2$O)$_{11}$CH$_3$, δ 3.91-4.00 (b, —NHCH(CH(CH$_3$)CH$_2$CH$_3$))COOCH$_2$CH$_3$ and —NHC$\underline{H_2}$CH$_2$COCHCH$_2$)

δ 4.11-4.40 (b, —NHCH(CH(CH$_3$)(CH$_2$CH$_3$))COOC$\underline{H_2}$CH$_3$)

δ 5.82 (t, 1H), —NHCH$_2$CH$_2$COCHC$\underline{H_2}$)

δ 6.2 (S, 1H), —NHCH$_2$CH$_2$COCHC$\underline{H_2}$)

δ 6.42 (d, 1H), —NHCH$_2$CH$_2$C$\underline{O}$CHCH$_2$)

Phosphorus Nuclear Magnetic Resonance Spectrum (CDCl$_3$, ppm): δ 19.9

Average molecular weight (Mw): 430000

Example 10

Preparation of Poly[(isoleucineethylester)(aminomethoxy polyethyleneglycol550)(acrylate)phosphazene], [NP(IleOEt)$_{0.91}$(AMPEG550)$_{0.66}$(Acrylate)$_{0.43}$]$_n$ With the same method as in Example 9, 13.80 g of the end product, [NP(IleOEt)$_{0.91}$(AMPEG550)$_{0.66}$(Acrylate)$_{0.43}$]$_n$ was obtained by using 4.00 g (34.48 mmol) of poly(dichlorophosphazene), 5.53 g (28.37 mmol) of isoleucineethylester hydrogen chloride salt, 3.85 g (63.00 mmol) of amino ethanol, 10.81 g (19.60 mmol) of aminomethoxy polyethyleneglycol having the weight-average molecular weight of 550, 6.47 g (31.38 mmol) of dicyclohexylcarbodiimide, 4.61 g (37.66 mmol) of dimethyl amino pyridine, 2.24 g (31.38 mmol) of acrylic acid, 29.43 g (290.84 mmol) of triethylamine, and 450 ml of tetrahydrofurane. (Yield: 63%)

Hydrogen Nuclear Magnetic Resonance Spectrum (CDCl$_3$, ppm):

δ 0.91-1.05 (s, —NHCH(CH(C$\underline{H_3}$)(CH$_2$C$\underline{H_3}$))COOCH$_2$CH$_3$), δ 1.05-1.40 (b, —NHCH(CH(CH$_3$)(CH$_2$CH$_3$))COOCH$_2$C$\underline{H_3}$)

δ 1.40-1.62 (b, —NHCH(CH(CH$_3$)(C$\underline{H_2}$CH$_3$))COOCH$_2$CH$_3$)

δ 1.62-1.85 (b, —NHCH(CH(CH$_3$)(CH$_2$CH$_3$))COOCH$_2$CH$_3$)

δ 2.80-3.18 (b, —NHCH$_2$CH$_2$O— and —NHCH$_2$CH$_2$COCHCH$_2$)

δ 3.38 (s, —NH(CH$_2$CH$_2$O)$_{11}$CH$_3$),

δ 3.50-3.91 (b, 44H), —NH(CH$_2$CH$_2$O)$_{11}$CH$_3$

δ 3.91-4.00 (b, —NHCH(CH(CH$_3$)(CH$_2$CH$_3$))COOCH$_2$CH$_3$ and —NHCH$_2$CH$_2$COCHCH$_2$)

δ 4.11-4.40 (b, —NHCH(CH(CH$_3$)(CH$_2$CH$_3$))COOCH$_2$CH$_3$)

δ 5.82 (t, 1H), —NHCH$_2$CH$_2$COCHCH$_2$)

δ 6.2 (S, 1H), —NHCH$_2$CH$_2$COCHCH$_2$)

δ 6.42 (d, 1H), —NHCH$_2$CH$_2$COCHCH$_2$)

Phosphorus Nuclear Magnetic Resonance Spectrum (CDCl$_3$, ppm): δ 19.9

Average molecular weight (M$_w$): 270000

Example 11

Preparation of Poly[(isoleucineethylester)(aminomethoxy polyethyleneglycol750)(acrylate)phosphazene], [NP(IleOEt)$_{1.23}$(AMPEG750)$_{0.42}$(Acrylate)$_{0.35}$]$_n$ With the same method as in Example 9, 14.36 g of the end product, [NP(IleOEt)$_{1.23}$(AMPEG750)$_{0.42}$(Acrylate)$_{0.35}$]$_n$ was obtained by using 4.00 g (34.48 mmol) of poly(dichlorophosphazene), 8.44 g (43.14 mmol) of isoleucineethylester hydrogen chloride salt, 2.53 g (41.42 mmol) of amino ethanol, 9.06 g (12.08 mmol) of aminomethoxy polyethyleneglycol having the weight-average molecular weight of 750, 5.45 g (26.45 mmol) of dicyclohexylcarbodiimide, 3.89 g (31.74 mmol) of dimethyl amino pyridine, 1.89 g (26.45 mmol) of acrylic acid, 31.12 g (307.55 mmol) of triethylamine, and 450 ml of tetrahydrofurane. (Yield: 70%)

Hydrogen Nuclear Magnetic Resonance Spectrum (CDCl$_3$, ppm):

δ 0.91-1.05 (s, —NHCH(CH(CH$_3$)(CH$_2$CH$_3$))COOCH$_2$CH$_3$),

δ 1.05-1.40 (b, —NHCH(CH(CH$_3$)(CH$_2$CH$_3$))COOCH$_2$CH$_3$)

δ 1.40-1.62 (b, —NHCH(CH(CH$_3$)(CH$_2$CH$_3$))COOCH$_2$CH$_3$)

δ 1.62-1.85 (b, —NHCH(CH(CH$_3$)(CH$_2$CH$_3$))COOCH$_2$CH$_3$)

δ 2.80-3.18 (b, —NHCH$_2$CH$_2$O— and —NHCH$_2$CH$_2$COCHCH$_2$)

δ 3.38 (s, —NH(CH$_2$CH$_2$O)$_{15}$CH$_3$),

δ 3.50-3.91 (b, 44H), —NH(CH$_2$CH$_2$O)$_{15}$CH$_3$

δ 3.91-4.00 (b, —NHCH(CH(CH$_3$)(CH$_2$CH$_3$))COOCH$_2$CH$_3$ and —NHCH$_2$CH$_2$COCHCH$_2$)

δ 4.11-4.40 (b, —NHCH(CH(CH$_3$)(CH$_2$CH$_3$))COOCH$_2$CH$_3$)

δ 5.82 (t, 1H), —NHCH$_2$CH$_2$COCHCH$_2$)

δ 6.2 (S, 1H), —NHCH$_2$CH$_2$COCHCH$_2$)

δ 6.42 (d, 1H), —NHCH$_2$CH$_2$COCHCH$_2$)

Phosphorus Nuclear Magnetic Resonance Spectrum (CDCl$_3$, ppm): ☐ 19.7

Average molecular weight (MO: 320000

Example 12

Preparation of Poly[(isoleucineethylester)(aminomethoxy polyethyleneglycol550)(glycylglycine)(glycylglycylaminoethylmethacrylate)phosphazene], [NP(IleOEt)$_{1.27}$(AMPEG550)$_{0.51}$(GlyGlyOH)$_{0.09}$(GlyGlyAEMA)$_{0.13}$]$_n$ 4.29 g (21.92 mmol) of a dried isoleucine ethyl ester hydrogen chloride salt was dissolved in 100 ml of anhydrous tetrahydrofuran, and then 6.65 g (65.76 mmol) of triethylamine was added thereto. To this solution was added dropwise 2.00 g (17.26 mmol) of poly(dichlorophosphazene) dissolved in 50 ml of anhydrous tetrahydrofuran, in a dry ice-acetone bath at −60° C., and then it was warmed to room temperature to react for 48 hours.

After checking the progress of the reaction by $^{31}$P-NMR, 2.17 g (7.59 mmol) of a dried glyclgylcine allylester trifluoro acetic acid salt was dissolved in 50 ml of anhydrous tetrahydrofuran, 2.30 g (22.77 mmol) of triethylamine was added thereto, and then the resulting solution was added to the reaction product to react for 8 hours. After checking the progress of the reaction again by $^{31}$P-NMR, the solution prepared by dissolving 12.10 g (22.01 mmol) of a dried amino methoxy polyethylene glycol having the weight-average molecular weight of 550 in 50 ml of anhydrous tetrahydrofurane was added dropwise to the reaction product to react at room temperature for 12 hours and at 40-50° C. for another 24 hours.

The reaction solution was filtered to remove the triethylamine hydrochloride salt as generated and the reaction filterate was concentrated under a reduced pressure until a small amount of solvent remained. The concentrate was dissolved in 10 ml of tetrahydrofuran and an excess amount of hexane was added thereto to induce a precipitation. After this procedure was repeated 2 to 3 times, the resulting precipitate was dissolved again in a small amount of methyl alcohol, and then it was put into an MWCO 12000 membrane (Spectrum Laboratories, Inc.), and subjected to a dialysis with methyl alcohol at room temperature for 5 days and then to a dialysis with distilled water for 5 days, and dried at a low temperature to give 14.21 g of the poly(dichlorophosphazene) polymer, [NP(IleOEt)$_{1.27}$(AMPEG550)$_{0.51}$(GlyGlyOAll)$_{0.22}$]$_n$.

14.21 g of [NP(IleOEt)$_{1.27}$(AMPEG550)$_{0.51}$(GlyGlyOAll)$_{0.22}$]$_n$ as obtained was dissolved in 200 ml of anhydrous THF, and reacted at room temperature for 8 hours by using 15 mol % (0.56 g) of tetrakis-triphenylphosphine palladium (0) and 4.23 g (20 equiv.) of morpholine. The reaction filterate was concentrated under a reduced pressure, dissolved in a small amount of methyl alcohol, and then it was put into an MWCO 6-8000 membrane (Spectrum Laboratories, Inc.), and subjected to a dialysis with methyl alcohol at room temperature for 5 days and then to a dialysis with distilled water at 4° C. for 5 days, and dried at a low temperature to give 13.78 g of an intermediate product, [NP(IleOEt)$_{1.27}$(AMPEG550)$_{0.51}$(GlyGlyOH)$_{0.22}$]$_n$.

13.78 g of [NP(IleOEt)$_{1.27}$(AMPEG550)$_{0.51}$(GlyGlyOH)$_{0.22}$]$_n$ as obtained was dissolved in 100 ml of anhydrous chloromethane, and 0.26 equiv. (0.39 g) of aminoethylmethacrylate, 0.52 equiv. (0.16 g) of dicyclohexylcarbodiimide, and 0.52 equiv. (0.10 g) of dimethyl amino pyridine were added thereto to react at 0° C. for 24 hours. The reaction filterate was concentrated under a reduced pressure and dissolved in a small amount of methyl alcohol, and then it was put into an MWCO 6-8000 membrane (Spectrum Laboratories, Inc.), and subjected to a dialysis with methyl alcohol at room temperature for 5 days and then to a dialysis with distilled water at 4° C. for 5 days, and was dried at a low temperature to give 13.02 g of the end product, [NP(IleOEt)$_{1.27}$(AMPEG550)$_{0.51}$(GlyGlyOH)$_{0.09}$(GlyGlyAEMA)$_{0.13}$]$_n$. (Yield: 89%)

Hydrogen Nuclear Magnetic Resonance Spectrum (CDCl$_3$, ppm):
δ 0.8-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$),
δ 1.9 (s, —NHCH$_2$CONHCH$_2$CONHCH$_2$CH$_2$O$_2$C(CH$_3$)C=CH$_2$)
δ 3.4 (s, —NH(CH$_2$CH$_2$O)$_{11}$CH$_3$),
δ 3.5-3.9 (b, —NH(C$\underline{H_2}$CH$_2$O)$_{11}$CH$_3$, —NHCH(CH(CH$_3$)(CH$_2$CH$_3$))COOC$\underline{H_2}$C$\underline{H_3}$),
δ 4.0-4.4 (b, —NHCH(CH(CH$_3$)(CH$_2$CH$_3$))COOCH$_2$CH$_3$, —OCH$_2$CH$_2$O$_2$C(CH$_3$)C=CH$_2$),
δ 5.5 (s, —N$\underline{H}$C$\underline{H_2}$CONHCH$_2$CONHCH$_2$CH$_2$O$_2$C(CH$_3$)C=CH$_2$)
δ 6.1 (s, —NHCH$_2$CONHCH$_2$CONHCH$_2$CH$_2$O$_2$C(CH$_3$)C=CH$_2$)

Phosphorus Nuclear Magnetic Resonance Spectrum (CDCl$_3$, ppm): δ 18.4

Average molecular weight (MO: 169200

Example 13

Preparation of Poly[(isoleucineethylester)(aminomethoxy polyethyleneglycol550)(glycylglycine)(glycylglycylhydroxyethylmethacrylate) phosphazene], [NP(IleOEt)$_{1.29}$(AMPEG550)$_{0.54}$(GlyGlyOH)$_{0.02}$(GlyGlyHEMA)$_{0.15}$]$_n$ With the same method as in Example 12, 9.49 g of the end product, [NP(IleOEt)$_{1.29}$(AMPEG550)$_{0.54}$(GlyGlyOH)$_{0.02}$(GlyGlyHEMA)$_{0.51}$]$_n$ was obtained by using 2.00 g of (17.26 mmol) poly(dichlorophosphazene), 4.36 g (22.27 mmol) of isoleucineethylester, 1.68 g (5.87 mmol) of glycylglycine allylester trifluoro acetic acid salt, 12.82 g (23.30 mmol) of aminomethoxy polyethyleneglycol having the weight-average molecular weight of 550, 0.77 g (0.59 mmol) of tetrakistriphenylphosphine palladium(0), 5.11 g (58.68 mmol) of morpholine, 1.12 g (6.70 mmol) of hydroxyethylmethacrylate, 1.38 g (6.70 mmol) of dicyclohexylcarbodiimide, 0.82 g (6.70 mmol) of dimethylaminopyridine, 15.62 g (154.32 mmol) of triethylamine, 550 ml of tetrahydrofurane, and 100 ml of dichloromethane. (Yield: 77%)

Hydrogen Nuclear Magnetic Resonance Spectrum (CDCl$_3$, ppm):
δ 0.8-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$),
δ 1.9 (s, —NHCH$_2$CONHCH$_2$CO$_2$CH$_2$CH$_2$O$_2$C(CH$_3$)C=CH$_2$)
δ 3.4 (s, —NH(CH$_2$CH$_2$O)$_{11}$CH$_3$),
δ 3.5-3.9 (b, —NH(C$\underline{H_2}$CH$_2$O)$_{11}$CH$_3$, —NHCH(CH(CH$_3$)(CH$_2$CH$_3$))COOC$\underline{H_2}$C$\underline{H_3}$),
δ 4.0-4.4 (b, —NHCH(CH(CH$_3$)(CH$_2$CH$_3$))COOCH$_2$CH$_3$, —OCH$_2$CH$_2$O$_2$C(CH$_3$)C=CH$_2$),
δ 5.4 (s, —N$\underline{H}$C$\underline{H_2}$CONHCH$_2$CO$_2$CH$_2$CH$_2$O$_2$C(CH$_3$)C=CH$_2$)
δ 6.0 (s, —NHCH$_2$CONHCH$_2$CO$_2$CH$_2$CH$_2$O$_2$C(CH$_3$)C=CH$_2$)

Phosphorus Nuclear Magnetic Resonance Spectrum (CDCl$_3$, ppm): δ 19.4

Average molecular weight (M$_w$): 366900

Example 14

Preparation of Poly[(isoleucineethylester)(aminomethoxy polyethyleneglycol550)(cystineethylester)phosphazene], [NP(IleOEt)$_{1.21}$(AMPEG550)$_{0.64}$(CysOEt)$_{0.15}$]$_n$ With the same method as in Example 2, 14.19 g of the product, [NP(IleOEt)$_{1.21}$(AMPEG550)$_{0.64}$(CbzCysOEt)$_{0.15}$]$_n$ was obtained by using 2.00 g (17.26 mmol) of poly(dichlorophosphazene), 4.09 g (20.88 mmol) of isoleucineethylester, 1.66 g (5.18 mmol) of benzyloxycarbonyl cystine ethylester, 15.19 g (27.62 mmol) of aminomethoxy polyethyleneglycol having the weight-average molecular weight of 550, 16.30 g (161.04 mmol) of triethylamine, and 550 ml of tetrahydrofurane.

14.19 g of [NP(IleOEt)$_{1.21}$(AMPEG550)$_{0.64}$(CbzCysOEt)$_{0.15}$]$_n$ as obtained was dissolved in 200 ml of ethyl alcohol, and 50 wt % (8.4 g) of palladium/charcoal was added thereto to react in the presence of 60 to 70 psi of hydrogen gas at room temperature for 12 hours. After that, the reaction solution was filterated, and the reaction filtrate was concentrated under a reduced pressure. After the concentrate was dissolved in a small amount of methyl alcohol, it was subjected to a dialysis with methyl alcohol at room temperature for 5 days and then to a dialysis with distilled water at 4° C. for 5 days, and was dried at a low temperature to give 9.23 g of the end product, [NP(IleOEt)$_{1.21}$(AMPEG550)$_{0.64}$(CysOEt)$_{0.15}$]$_n$. (Yield: 73%)

Hydrogen Nuclear Magnetic Resonance Spectrum (CDCl$_3$, ppm):
δ 1.1-1.4 (b, —NHCH(CH(CH$_3$)(CH$_2$CH$_3$))COOCH$_2$CH$_3$, —NHCH(CH$_2$SH)(COOCH$_2$CH$_3$)),
δ 3.0-3.3 (b, —NHCH(CH$_2$SH)(C$\overline{OOCH_2}$CH$_3$)),
δ 3.4 (s, —NH(CH$_2$CH$_2\overline{O}$)$_{11}$CH$_3$),
δ 3.5-3.9 (b, —NH(C$\overline{H_2}$CH$_2$O)$_{11}$CH$_3$, —NHCH(CH$_2$SH)(COOCH$_2$CH$_3$)),
δ 4.0-4.4 (b, —NHCH(CH(CH$_3$)(CH$_2$CH$_3$))COOCH$_2$CH$_3$, —NHCH(CH$_2$SH)(C$\overline{OOCH_2}$CH$_3$))

Phosphorus Nuclear Magnetic Resonance Spectrum (CDCl$_3$, ppm): δ 20.1

Average molecular weight (M$_w$): 264000

Example 15

Preparation of Poly[(isoleucineethylester)(aminomethoxy polyethyleneglycol550)(cystineethylester)phosphazene], [NP(IleOEt)$_{0.96}$(AMPEG550)$_{0.78}$(CysOEt)$_{0.24}$]$_n$ With the same method as in Example 2, 8.88 g of the end product, [NP(IleOEt)$_{0.96}$(AMPEG550)$_{0.78}$(CysOEt)$_{0.24}$]$_n$ was obtained by using 2.00 g (17.26 mmol) of poly(dichlorophosphazene), 3.25 g (16.57 mmol) of isoleucineethylester, 2.66 g (8.29 mmol) of benzyloxycarbonyl cystine ethyl ester, 18.51 g (33.66 mmol) of aminomethoxy polyethyleneglycol having the weight-average molecular weight of 550, 50 wt % (13.44 g) of palladium/charcoal, 17.77 g (175.56 mmol) of triethylamine and 550 ml of tetrahydrofurane. (Yield: 74%)

Hydrogen Nuclear Magnetic Resonance Spectrum (CDCl$_3$, ppm):
δ 0.8-1.1 (b, —NHCH(CH(C$\underline{H_3}$)(CH$_2$C$\underline{H_3}$))COOCH$_2$CH$_3$), δ 1.1-1.4 (b, —NHCH(CH(CH$_3$)(CH$_2$CH$_3$))COOCH$_2$CH$_3$, —NHCH(CH$_2$SH)(COOCH$_2$CH$_3$)),
δ 3.0-3.3 (b, —NHCH(CH$_2$SH)(COOCH$_2$CH$_3$)),
δ 3.4 (s, —NH(CH$_2$CH$_2$O)$_{11}$CH$_3$),
δ 3.5-3.9 (b, —NH(CH$_2$CH$_2$O)$_{11}$CH$_3$, —NHCH(CH$_2$SH)(COOCH$_2$CH$_3$)),
δ 4.0-4.4 (b, —NHCH(CH(CH$_3$)(CH$_2$CH$_3$))COOCH$_2$CH$_3$, —NHCH(CH$_2$SH)(COOCH$_2$CH$_3$))
Phosphorus Nuclear Magnetic Resonance Spectrum (CDCl$_3$, ppm): δ 19.3
Average molecular weight (M$_w$): 423700

Example 16

Preparation of Poly[(isoleucineethylester)(aminomethoxy polyethyleneglycol750)(cystineethylester)phosphazene], [NP(IleOEt)$_{1.02}$(AMPEG750)$_{0.43}$(CysOEt)$_{0.54}$]$_n$ With the same method as in Example 2, 11.86 g of the product, [NP(IleOEt)$_{1.21}$(AMPEG750)$_{0.64}$(CysDiOEt)$_{0.15}$]$_n$ was obtained by using 2.00 g (17.26 mmol) of poly(dichlorophosphazene), 3.45 g (17.61 mmol) of isoleucineethylester, 6.88 g (18.64 mmol) of cystindiethylester hydrogen chloride salt, 13.92 g (18.55 mmol) of aminomethoxy polyethyleneglycol having the weight-average molecular weight of 750, 16.63 g (164.4 mmol) of triethylamine, and 550 ml of tetrahydrofurane.

11.86 g of [NP(IleOEt)$_{1.21}$(AMPEG750)$_{0.64}$(CysDiOEt)$_{0.15}$]$_n$ as obtained was dissolved in 200 ml of distilled water, and as an disulfide inhibitor, 1.44 g of dithioerytritol was added thereto. To the resulting solution was added a sodium hydroxide solution (concentration: 1 mole) to adjust the pH to 8.5 and reacted for 24 hours. Then, the reaction solution was filtered and the reaction filtrate was concentrated under a reduced pressure. After the concentrate was dissolved in a small amount of methyl alcohol, it was subjected to a dialysis with methyl alcohol at room temperature for 5 days and then to a dialysis with distilled water at 4° C. for 5 days, and dried at a low temperature to give 14.00 g of [NP(IleOEt)$_{1.02}$(AMPEG750)$_{0.43}$(CysOEt)$_{0.54}$]$_n$. (Yield: 83%)
Hydrogen Nuclear Magnetic Resonance Spectrum (CDCl$_3$, ppm):
δ 0.8-1.1 (b, —NHCH(CH(CH$_3$)(CH$_2$CH$_3$))COOCH$_2$CH$_3$),
δ 1.1-1.4 (b, —NHCH(CH(CH$_3$)(CH$_2$CH$_3$))COOCH$_2$CH$_3$),
δ 3.4 (s, —NH(CH$_2$CH$_2$O)$_{15}$CH$_3$),
δ 3.5-3.9 (b, —NH(CH$_2$CH$_2$O)$_{15}$CH$_3$, —NHCH(CH(CH$_3$)(CH$_2$CH$_3$))COOCH$_2$CH$_3$),
δ 4.0-4.4 (b, —NHCH(CH(CH$_3$)(CH$_2$CH$_3$))COOCH$_2$CH$_3$)
Phosphorus Nuclear Magnetic Resonance Spectrum (CDCl$_3$, ppm): □ 19.2
Average molecular weight (KO: 131000

Example 17

Preparation of Poly[(isoleucineethylester)(aminomethoxy polyethyleneglycol550)(ethyl-2-(O-glycyl)lactate)(cystine ethyl ester)phosphazene], [NP(IleOEt)$_{1.12}$(AMPEG550)$_{0.73}$(GlyLacOEt)$_{0.06}$(CysOEt)$_{0.09}$]$_n$ With the same method as in Example 2, 12.49 g of the product, [NP(IleOEt)$_{1.21}$(AMPEG550)$_{0.73}$(GlyLacOEt)$_{0.06}$(triCysOEt)$_{0.09}$]$_n$ was obtained by using 2.00 g (17.26 mmol) of poly(dichlorophosphazene), 3.78 g (19.33 mmol) of isoleucineethylester, 1.13 g (3.11 mmol) of trityl cystine, 2.85 g (2.07 mmol) of ethyl-2-(O-glycyplactate ammonium oxalic acid salt, 17.32 g (31.50 mmol) of aminomethoxy polyethyleneglycol having the weight-average molecular weight of 550, 17.00 g (168.03 mmol) of triethylamine, and 550 ml of tetrahydrofurane.

12.49 g of [NP(IleOEt)$_{1.21}$(AMPEG550)$_{0.73}$(GlyLacOEt)$_{0.06}$(triCysOEt)$_{0.09}$]$_n$ as obtained was dissolved in 200 ml of tetrahydrofurane, and 0.35 g of trifluoroacetic acid was added thereto to react for 12 hours. Then, the reaction solution was filtered and the reaction filtrate was concentrated under a reduced pressure. After the concentrate was dissolved in a small amount of methyl alcohol, it was subjected to a dialysis with methyl alcohol at room temperature for 5 days and then to a dialysis with distilled water at 4° C. for 5 days, and was dried at a low temperature to give 11.28 g of the end product, [NP(IleOEt)$_{1.21}$(AMPEG550)$_{0.73}$(GlyLacOEt)$_{0.06}$(CysOEt)$_{0.09}$]$_n$. (Yield: 85%)
Hydrogen Nuclear Magnetic Resonance Spectrum (CDCl$_3$, ppm):
δ 0.8-1.1 (b, —NHCH(CH(CH$_3$)(CH$_2$CH$_3$))COOCH$_2$CH$_3$),
δ 1.1-1.4 (b, —NHCH(CH(CH$_3$)(CH$_2$CH$_3$))COOCH$_2$CH$_3$, —NHCH$_2$COOCH(CH$_3$)(COOCH$_2$CH$_3$), —NHCH(CH$_2$SH)(COOCH$_2$CH$_3$)),
δ 3.0-3.3 (b, —NHCH(CH$_2$SH)(COOCH$_2$CH$_3$)),
δ 3.4 (s, —NH(CH$_2$CH$_2$O)$_{11}$CH$_3$),
δ 3.5-3.9 (b, —NH(CH$_2$CH$_2$O)$_{11}$CH$_3$, —NHCH(CH$_2$SH)(COOCH$_2$CH$_3$)),
δ 4.0-4.4 (b, —NHCH(CH(CH$_3$)(CH$_2$CH$_3$))COOCH$_2$CH$_3$, —NHCH2COOCH(CH$_3$)(COOCH$_2$CH$_3$)—NHCH(CH$_2$SH)(COOCH$_2$CH$_3$))
δ 5.1 (s, —NHCH2COOCH(CH$_3$)(COOCH$_2$CF$_{13}$)
Phosphorus Nuclear Magnetic Resonance Spectrum (CDCl$_3$, ppm): δ 19.8
Average molecular weight (M$_w$): 238000

Example 18

Preparation of Poly[(isoleucineethylester)(aminomethoxy polyethyleneglycol550)(ethyl-2-(O-glycyl)lactate)(glycylcystineethylester) phosphazene], [NP(IleOEt)$_{1.15}$(AMPEG550)$_{0.60}$(GlyLacOEt)$_{0.09}$(GlyCysOEt)$_{0.16}$]$_n$ With the same method as in Example 12, 9.14 g of the end product, [NP(IleOEt)$_{1.15}$(AMPEG550)$_{0.60}$(GlyLacOEt)$_{0.09}$(GlyCysOEt)$_{0.16}$]$_n$ was obtained by using 2.00 g (17.26 mmol) of poly(dichlorophosphazene), 3.88 g (19.85 mmol) of isoleucineethylester, 1.68 g (5.87 mmol) of glycine allylester trifluoro acetic acid, 14.24 g (25.89 mmol) of aminomethoxy polyethyleneglycol having the weight-average molecular weight of 550, 0.68 g (0.59 mmol) of tetrakistriphenylphosphine palladium(0), 5.11 g (58.7 mmol) of morpholine, 1.03 g (5.52 mmol) of cystine ethyl ester, 2.12 g (11.04 mmol) of 1-ethyl-3-(3-dimethyl amino propyl)carbodiimide hydrogen chloride salt, 17.34 g (171.39 mmol) of triethylamine, 550 ml of tetrahydrofurane, and 100 ml of dichloromethane. (Yield: 79%)
Hydrogen Nuclear Magnetic Resonance Spectrum (CDCl$_3$, ppm):
δ 0.8-1.1 (b, —NHCH(CH(CH$_3$)(CH$_2$CH$_3$))COOCH$_2$CH$_3$),
δ 1.1-1.4 (b, —NHCH(CH(CH$_3$)(CH$_2$CH$_3$))COOCH$_2$CH$_3$, —NHCH2COOCH(CH$_3$)(COOCH$_2$CH$_3$), —NHCH$_2$CONHCH(CH$_2$SH)(COOCH$_2$CH$_3$)), δ 2.3 (s, —NHCH$_2$CONHCH(CH$_2$SH)(COOCH$_2$CH$_3$))
δ 3.0 (s, —NHCH$_2$CONHCH(CH$_2$SH)(COOCH$_2$CH$_3$))
δ 3.4 (s, —NH(CH$_2$CH$_2$O)$_{11}$CH$_3$),
δ 3.5-3.9 (b, —NH(CH$_2$CH$_2$O)$_{11}$CH$_3$, —NHCH$_2$CONHCH(CH$_2$SH)(COOCH$_2$CH$_3$)
δ 4.0-4.4 (b, —NHCH(CH(CH$_3$)(CH$_2$CH$_3$))COOCH$_2$CH$_3$)—NHCH2COOCH(CH$_3$)(COOCH$_2$CH$_3$)—NHCH$_2$CONHCH(CH$_2$SH)(COOCH$_2$CH$_3$))
δ 5.1 (s, —NHCH2COOCH(CH$_3$)(COOCH$_2$CH$_3$)
Phosphorus Nuclear Magnetic Resonance Spectrum (CDCl$_3$, ppm): δ 19.7
Average molecular weight (M$_w$): 238000

Example 19

Preparation of Poly[(isoleucineethylester)(aminomethoxy polyethyleneglycol550)(glycylglycine)(glycylglycyleystineethylester)phosphazene], [NP(IleOEt)$_{1.19}$(AMPEG550)$_{0.64}$(GlyGlyOH)$_{0.05}$(GlyGlyCysOEt)$_{0.12}$]$_n$ With the same method as in Example 12, 10.75 g of the end product, [NP(IleOEt)$_{1.19}$(AMPEG550)$_{0.64}$(GlyGlyOH)$_{0.05}$(GlyGlyCysOEt)$_{0.12}$]$_n$ was obtained by using 2.00 g (17.26 mmol) of poly(dichlorophosphazene), 4.36 g (22.27 mmol) of isoleucineethylester, 1.68 g (5.87 mmol) of glycylglycine allylester trifluoro acetic acid salt, 15.19 g (27.62 mmol) of aminomethoxy polyethyleneglycol having the weight-average molecular weight of 550, 0.77 g (0.59 mmol) of tetrakistriphenylphosphine palladium(0), 5.11 g (58.68 mmol) of morpholine, 0.40 g (4.14 mmol) of cystine ethyl ester, 0.85 g (4.14 mmol) of dicyclohexylcarbodiimide, 0.51 g (4.14 mmol) of dimethylaminopyridine, 15.62 g (154.32 mmol) of triethylamine, 550 ml of tetrahydrofurane, and 100 ml of dichloromethane. (Yield: 81%)
Hydrogen Nuclear Magnetic Resonance Spectrum (CDCl$_3$, ppm):
δ 0.8-1.1 (b, —NHCH(CH(CH$_3$)(CH$_2$CH$_3$))COOCH$_2$CH$_3$),
δ 1.1-1.4 (b, —NHCH(CH(CH$_3$)(CH$_2$CH$_3$))COOCH$_2$CH$_3$, —NHCH$_2$CONHCH$_2$CONHCH(CH$_2$SH)(COOCH$_2$CH$_3$)),
δ 2.3 (s, —NHCH$_2$CONHCH$_2$CONHCH(CH$_2$SH)(COOCH$_2$CH$_3$))
δ 3.0 (s, —NHCH$_2$CONHCH$_2$CONHCH(CH$_2$SH)(COOCH$_2$CH$_3$))
δ 3.4 (s, —NH(CH$_2$CH$_2$O)$_{11}$CH$_3$),
δ 3.5-3.9 (b, —NH(CH$_2$CH$_2$O)$_{11}$CH$_3$, —NHCH$_2$CONHCH$_2$CONHCH(CH$_2$SH)(COOCH$_2$CH$_3$)),
δ 4.0-4.4 (b, —NHCH(CH(CH$_3$)(CH$_2$CH$_3$))COOCH$_2$CH$_3$, —NHCH$_2$CONHCH$_2$CONHCH(CH$_2$SH)(COOCH$_2$CH$_3$))
Phosphorus Nuclear Magnetic Resonance Spectrum (CDCl$_3$, ppm): δ 19.8
Average molecular weight (M$_w$): 129000

Example 20

Preparation of Poly[(isoleueineethylester)(aminomethoxy polyethyleneglycol550)(cysteamine)phosphazene], [NP(IleOEt)$_{1.18}$(AMPEG550)$_{0.62}$(cysteamine)$_{0.20}$]$_n$ With the same method as in Example 2, 9.81 g of the end product, [NP(IleOEt)$_{1.18}$(AMPEG550)$_{0.62}$(cysteamine)$_{0.20}$]$_n$ was obtained by using 2.00 g (17.26 mmol) of poly(dichlorophosphazene), 3.99 g (20.37 mmol) of isoleucineethylester, 14.71 g (26.75 mmol) of aminomethoxy polyethyleneglycol having the weight-average molecular weight of 550, 1.55 g (6.90 mmol) of cysteamine dihydrochloride salt, 1.06 g (6.90 mmol) of ditioerytritol, 16.40 g (162.06 mmol) of triethylamine, and 550 ml of tetrahydrofurane. (Yield: 78%)
Hydrogen Nuclear Magnetic Resonance Spectrum (CDCl$_3$, ppm):
δ 0.8-1.1 (b, —NHCH(CH(CH$_3$)(CH$_2$CH$_3$))COOCH$_2$CH$_3$),
δ 1.1-1.4 (b, —NHCH(CH(CH$_3$)(CH$_2$CH$_3$))COOCH$_2$CH$_3$),
δ 3.4 (s, —NH(CH$_2$CH$_2$O)$_{11}$CH$_3$),
δ 3.5-3.9 (b, —NH(CH$_2$CH$_2$O)$_{11}$CH$_3$, —NHCH(CH(CH$_3$)(CH$_2$CH$_3$))COOCH$_2$CH$_3$),
δ 4.0-4.4 (b, —NHCH(CH(CH$_3$)(CH$_2$CH$_3$))COOCH$_2$CH$_3$)
Phosphorus Nuclear Magnetic Resonance Spectrum (CDCl$_3$, ppm): δ 20.1
Average molecular weight (M$_w$): 217000

Example 21

Preparation of Poly[(isoleucineethylester)(aminomethoxy polyethyleneglycol550)(cysteamine)phosphazene], [NP(IleOEt)$_{0.88}$(AMPEG550)$_{0.54}$(cysteamine)$_{0.54}$]$_n$ Since the cysteamine dihydrochloride salt as used in Example 20 has a poor solubility, the synthesis in large scale requires a large amount of THF. Therefore, in the present example, the dihydrochloride salt was removed from the cysteamine dihydrochloride salt before the preparation of the polymer. Cysteamine was prepared as follows. First, 30 g (0.14 mol) of cysteamine dihydrochloride salt was dissolved in 50 ml of distilled water, and 150 ml of chloroform was added thereto, stirred, and stored at –5° C. To this was added slowly 40 g (1 mmol) of a refrigerated 40% sodium hydroxide solution, and stirred at –5° C. for 15 minutes. This solution was extracted using chloroform and dried with magnesium sulfate, and then it was distilled under a reduced pressure to give cysteamine.
The polymer of Example 21 was synthesized as follows. First, 6.00 g (30.6 mmol) of a dried isoleucineethylester hydrogen chloride salt was dissolved in 100 ml of anhydrous tetrahydrofurane, and 12.93 g (92 mmol) of triethylamine was added thereto. To this solution was added dropwise 4.00 g (34.48 mmol) of poly(dichlorophosphazene) dissolved in 100 ml of anhydrous tetrahydrofurane in a dry ice-acetone bath at –60° C. Then, the resulting mixture was warmed slowly to room temperature to react for 48 hours.
After checking the progress of the reaction by $^{31}$P-NMR, a solution prepared by dissolving 7.96 g (14.48 mmol) of a dried aminomethoxy polyethyleneglycol having the weight-average molecular weight of 550 and 6.10 g (44 mmol) of triethylamine in 50 ml of tetrahydrofurane was added dropwise to the reaction product and reacted at room temperature for 24 hours and at 40-50° C. for another 24 hours.
After checking the progress of the reaction again by $^{31}$P-NMR, 10.85 g (71.37 mmol) of a dried cysteamine was dissolved in 10 ml of anhydrous chloroform, and 10.85 g (20.06 mmol) of triethylamine was added thereto. The resulting mixture was added to the reaction product at 0° C. to react at room temperature for 24 hours and at 40-50° C. for another 24 hours.
The reaction solution was filtered to remove the triethylamine hydrochloride salt as generated and the reaction filterate was concentrated under a reduced pressure until only a small amount of the solvent remained. The concentrate was dissolved in 10 ml of tetrahydrofuran and an excess amount of hexane was added thereto to induce a precipitation. After this procedure was repeated 2 to 3 times, the resulting precipitate was dissolved again in a small amount of methyl alcohol, put into an MWCO 12000 membrane (Spectrum Laboratories, Inc.), subjected to a dialysis with methyl alcohol at room temperature for 5 days and then to a dialysis with distilled water for 5 days, and it was freeze-dried to give 15.54 g of the polymer, [NP(IleOEt)$_{0.88}$(AMPEG550)$_{0.54}$(cysteamine)$_{0.58}$]$_n$. (Yield: 81%)

Hydrogen Nuclear Magnetic Resonance Spectrum (CDCl$_3$, ppm):

δ 0.8-1.1 (b, —NHCH(CH($\underline{CH_3}$)(CH$_2$$\underline{CH_3}$))COOCH$_2$CH$_3$), δ 1.1-1.4 (b, —NHCH(CH(CH$_3$)(CH$_2$CH$_3$))COOCH$_2$$\underline{CH_3}$), δ 1.4-1.6 (b, —NHCH(CH(CH$_3$)($\underline{CH_2}$CH$_3$))COOCH$_2$CH$_3$), δ 1.6-1.9 (b, —NH$\underline{CH}$(CH(CH$_3$)(CH$_2$CH$_3$))COOCH$_2$CH$_3$), δ 2.8-2.9 (b, —NH$\underline{CH_2CH_2}$SS$\underline{CH_2CH_2}$NH$_2$), δ 2.9-3.3 (b, —NH$\underline{CH_2CH_2}$SS$\underline{CH_2CH_2}$NH$_2$), (s, —NH$\underline{CH_2CH_2}$—O—(CH$_2$$\underline{CH_2O}$)$_{10}$$\underline{CH_3}$), δ 3.4 (s, —NH(CH$_2$CH$_2$O)$_{11}$$\underline{CH_3}$), δ 3.5-3.9 (b, —NH($\underline{CH_2CH_2}$O)$_{11}$CH$_3$, —NHCH(CH(CH$_3$)(CH$_2$CH$_3$))COO$\underline{CH_2CH_3}$), δ 4.0-4.4 (b, —NHCH(CH(CH$_3$)(CH$_2$CH$_3$))COO$\underline{CH_2}$CH$_3$)

Phosphorus Nuclear Magnetic Resonance Spectrum (CDCl$_3$, ppm): δ 19.8

The following procedure was further carried out for changing the cycleamine into a thiol group suitable for crosslinking. 15.0 g (26.36 mmol) of the previously prepared polymer and 24.37 g (158.16 mmol) of DTT were dissolved in 300 ml of distilled water, and then stirred at room temperature for 24 hours. After the pH of the reaction product lowered to 3.5 using 1.0N HCl, this solution was put into an MWCO 3500 membrane (Spectrum Laboratories, Inc.), subjected to a dialysis with distilled water adjusted to have the pH of 3.5 in the same method, and then freeze-dried to give 13.05 g of the resulting polymer, [NP(IleOEt)$_{0.88}$(AMPEG550)$_{0.54}$(cysteamine)$_{0.54}$]$_n$. (Yield: 93%)

Hydrogen Nuclear Magnetic Resonance Spectrum (CDCl$_3$, ppm):

δ 0.8-1.1 (b, —NHCH(CH($\underline{CH_3}$)(CH$_2$$\underline{CH_3}$))COOCH$_2$CH$_3$), δ 1.1-1.4 (b, —NHCH(CH(CH$_3$)(CH$_2$CH$_3$))COOCH$_2$$\underline{CH_3}$), δ 1.4-1.6 (b, —NHCH(CH(CH$_3$)($\underline{CH_2}$CH$_3$))COOCH$_2$CH$_3$, —NH$\underline{CH_2}$CH$_2$SH), δ 1.6-1.9 (b, —NH$\underline{CH}$(CH(CH$_3$)(CH$_2$CH$_3$))COOCH$_2$CH$_3$), δ 2.6-2.8 (b, —NHCH$_2$$\underline{CH_2}$SH), δ 2.9-3.3 (b, —$\underline{NHCH_2}$CH$_2$SH), (s, —NH$\underline{CH_2CH_2}$—O—(CH$_2$CH$_2$O)$_{10}$$\underline{CH_3}$), δ 3.4 (s, —NH(CH$_2$CH$_2$O)$_{11}$$\underline{CH_3}$), δ 3.5-3.9 (b, —NH($\underline{CH_2CH_2}$O)$_{11}$CH$_3$, NHCH(CH(CH$_3$)(CH$_2$CH$_3$))COO$\underline{CH_2CH_3}$), δ 4.0-4.4 (b, —NHCH(CH(CH$_3$)(CH$_2$CH$_3$))COO$\underline{CH_2}$CH$_3$)

Phosphorus Nuclear Magnetic Resonance Spectrum (CDCl$_3$, ppm): δ 19.8

Average molecular weight (M$_w$): 340000

Example 22

Preparation of Poly[(isoleucineethylester)(aminomethoxy polyethyleneglycol550)(cysteamine) phosphazene], [NP(IleOEt)$_{0.74}$(AMPEG550)$_{0.49}$(cysteamine)$_{0.77}$]$_n$ With the same method as in Example 21, 15.21 g of the polymer [NP(IleOEt)$_{0.74}$(AMPEG550)$_{0.49}$(cysteamine)$_{0.77}$]$_n$ was obtained by using 4.00 g (34.48 mmol) of poly(dichlorophosphazene), 5.39 g (20.37 mmol) of isoleucineethylester, 7.68 g (13.96 mmol) of aminomethoxy polyethyleneglycol having the weight-average molecular weight of 550, 12.5 g (82.2 mmol) of cysteamine, 12.73 g (162.06 mmol) of triethylamine, and 550 ml of tetrahydrofurane. (Yield: 81%)

Further, 14.5 g (26.46 mmol) of the previously prepared polymer and 24.46 g (158.76 mmol) of DTT was used to yield 12.52 g of the end product, [NP(IleOEt)$_{0.74}$(AMPEG550)$_{0.49}$(cysteamine)$_{0.77}$]$_n$. (Yield: 97%)

Hydrogen Nuclear Magnetic Resonance Spectrum (CDCl$_3$, ppm):

δ 0.8-1.1 (b, —NHCH(CH($\underline{CH_3}$)(CH$_2$$\underline{CH_3}$))COOCH$_2$CH$_3$), δ 1.1-1.4 (b, —NHCH(CH(CH$_3$)(CH$_2$CH$_3$))COOCH$_2$$\underline{CH_3}$), δ 1.4-1.6 (b, —NHCH(CH(CH$_3$)($\underline{CH_2}$CH$_3$))COOCH$_2$CH$_3$, —NH$\underline{CH_2}$CH$_2$SH), δ 1.6-1.9 (b, —NH$\underline{CH}$(CH(CH$_3$)(CH$_2$CH$_3$))COOCH$_2$CH$_3$), δ 2.6-2.8 (b, —NHCH$_2$$\underline{CH_2}$SH), δ 2.9-3.3 (b, —$\underline{NHCH_2}$CH$_2$SH), (s, —NH$\underline{CH_2CH_2}$—O—(CH$_2$CH$_2$O)$_{10}$$\underline{CH_3}$), δ 3.4 (s, —NH(CH$_2$CH$_2$O)$_{11}$$\underline{CH_3}$), δ 3.5-3.9 (b, —NH($\underline{CH_2CH_2}$O)$_{11}$CH$_3$, —NHCH(CH(CH$_3$)(CH$_2$CH$_3$))COO$\underline{CH_2CH_3}$), δ 4.0-4.4 (b, —NHCH(CH(CH$_3$)(CH$_2$CH$_3$))COO$\underline{CH_2}$CH$_3$)

Phosphorus Nuclear Magnetic Resonance Spectrum (CDCl$_3$, ppm): δ 19.9

Average molecular weight (Mw): 240000

Example 23

Preparation of Poly[(isoleueineethylester)(aminomethoxy polyethyleneglycol550)(glycylglyeine)(glyeylglycylcysteamine)phosphazene], [NP(IleOEt)$_{1.15}$(AMPEG550)$_{0.67}$(GlyGlyOH)$_{0.05}$(GlyGlycysteamine)$_{0.13}$]$_n$ With the same method as in Example 12, 9.99 g of the end product, [NP(IleOEt)$_{1.15}$(AMPEG550)$_{0.67}$(GlyGlyOH)$_{0.05}$(GlyGlycysteamine)$_{0.13}$]$_n$ was obtained by using 2.00 g (17.26 mmol) of poly(dichlorophosphazene), 3.88 g (19.85 mmol) of isoleucineethylester, 1.78 g (6.21 mmol) of glycylglycine allylester trifluoro acetic acid salt, 15.90 g (28.91 mmol) of aminomethoxy polyethyleneglycol having the weight-average molecular weight of 550, 0.72 g (0.62 mmol) of tetrakis-triphenylphosphine palladium(0), 5.41 g (62.14 mmol) of morpholine, 0.51 g (4.49 mmol) of cysteamine hydrogen chloride salt, 0.93 g (4.49 mmol) of dicyclohexylcarbodiimide, 0.55 g (4.49 mmol) of dimethylaminopyridine, 16.65 g (164.58 mmol) of triethylamine, 550 ml of tetrahydrofurane, and 100 ml of dichloromethane. (Yield: 76%)

Hydrogen Nuclear Magnetic Resonance Spectrum (CDCl$_3$, ppm):
δ 0.7-1.1 (b, —NHCH(CH(C$\underline{H_3}$)CH$_2$CH$_3$)COOCH$_2$CH$_3$),
δ 1.1-1.3 (b, —NHCH(CH(CH$_3$)C$\underline{H_2}$C$\underline{H_3}$)COOCH$_2$CH$_3$),
δ 1.4-1.8 (b, —NHCH(CH(CH$_3$)C$\underline{H_2}$CH$_3$)COOC$\underline{H_2}$C$\underline{H_3}$),
δ 2.8 (b, —NHC$\underline{H_2}$CONHCH$_2$CONHCH$_2$C$\underline{H_2}$SH),
δ 3.4 (s, —NH(CH$_2$CH$_2$O)$_{11}$C$\underline{H_3}$),
δ 3.5 (b, —NHCH$_2$CONHC$\underline{H_2}$CONHCH$_2$CH$_2$SH),
δ 3.4-3.8 (b, —N$\underline{H}$(CH$_2$CH$_2$O)$_{11}$CH$_3$),
δ 3.9-4.3 (b, —NHC$\underline{H}$(CH(CH$_3$)CH$_2$CH$_3$)COOCH$_2$CH$_3$, —NHCH$_2$CONHCH$_2$CONHCH$_2$CH$_2$SH)

Phosphorus Nuclear Magnetic Resonance Spectrum (CDCl$_3$, ppm): δ 19.8

Average molecular weight (Mw): 312000

Example 24

Preparation of Poly[(isoleucineethylester)(aminomethoxy polyethyleneglycol550)(tyramine)phosphazene], [NP(IleOEt)$_{1.14}$(AMPEG550)$_{0.69}$(Tyramine)$_{0.16}$]$_n$ With the same method as in Example 2, 9.81 g of the end product, [NP(IleOEt)$_{1.18}$(AMPEG550)$_{0.62}$(Tyramine)$_{0.20}$]$_n$ was obtained by using 2.00 g (17.26 mmol) of poly(dichlorophosphazene), 3.04 g (15.52 mmol) of isoleucineethylester, 3.79 g (6.90 mmol) of aminomethoxy polyethyleneglycol having the weight-average molecular weight of 550, 3.31 g (24.14 mmol) of tyramine, 17.32 g (99.14 mmol) of triethylamine, 200 ml of tetrahydrofurane, and 50 ml of dimethylformamide. (Yield: 78%)

Hydrogen Nuclear Magnetic Resonance Spectrum (CDCl$_3$, ppm):
δ 0.7-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$),
δ 1.4-1.8 (b, —NHCH(CH(CH$_3$)CH$_2$CH$_3$)OCH$_2$CH$_3$)
δ 2.4-2.8 (b, —NHC$\underline{H_2}$C$\underline{H_2}$C$_6$H$_4$OH)
δ 2.8-3.1 (b, —NH(C$\underline{H_2}$C$\underline{H_2}$O)$_{11}$CH$_3$)
δ 3.4 (s, —NH(CH$_2$C$\underline{H_2}$O)$_{11}$C$\underline{H_3}$),
δ 3.5-3.9 (b, —NH(CH$_2$CH$_2$O$\underline{)}_{11}$CH$_3$),
δ 3.9-4.3 (s, —N$\underline{H}$C$\underline{H}$(CH(CH$_3$)(CH$_2$CH$_3$))COOCH$_2$CH$_3$),
δ 6.7-6.9 (b, —NHCH2CH2C6H4OH),
δ 6.9-7.1 (b, —NHCH2CH2C6H$\overline{4}$OH)

Phosphorus Nuclear Magnetic Resonance Spectrum (CDCl$_3$, ppm): δ 19.8

Average molecular weight (Mw): 58000

Example 25

Preparation of Poly[(isoleucineethylester)(aminomethoxy polyethyleneglycol550)(glycylglyeine)(glycylglycyltyramine)phosphazene], [NP(IleOEt)$_{1.15}$(AMPEG550)$_{0.67}$(GlyGlyOH)$_{0.05}$(GlyGlytyramine)$_{0.13}$]$_n$ With the same method as in Example 12, 8.78 g of the end product, [NP(IleOEt)$_{1.15}$(AMPEG550)$_{0.67}$(GlyGlyOH)$_{0.05}$(GlyGlytyramine)$_{0.13}$]$_n$ was obtained by using 2.00 g (17.26 mmol) of poly(dichlorophosphazene), 3.88 g (19.85 mmol) of isoleucineethylester, 1.78 g (6.21 mmol) of glycylglycine allylester trifluoro acetic acid salt, 15.90 g (28.91 mmol) of aminomethoxy polyethyleneglycol having the weight-average molecular weight of 550, 0.72 g (0.62 mmol) of tetrakistriphenylphosphine palladium(0), 5.41 g (62.14 mmol) of morpholine, 0.51 g (4.49 mmol) of tyramine, 0.93 g (4.49 mmol) of dicyclohexylcarbodiimide, 0.55 g (4.49 mmol) of dimethylaminopyridine, 16.65 g (164.58 mmol) of triethylamine, 550 ml of tetrahydrofurane, and 50 ml of dimethylformamide. (Yield: 76%)

Hydrogen Nuclear Magnetic Resonance Spectrum (CDCl$_3$, ppm):
δ 0.7-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$),
δ 1.4-1.8 (b, —NHCH(CH(CH$_3$)CH$_2$CH$_3$OCH$_2$CH$_3$)
δ 2.4-2.8 (b, —NHCH$_2$CONHCH$_2$CONHCH$_2$C$\underline{H_2}$C$_6$H$_4$OH)
δ 2.8-3.1 (b, —NH(C$\underline{H_2}$CH$_2$O)$_{11}$CH$_3$)
δ 3.4 (s, —NH(CH$_2$C$\underline{H_2}$O)$_{11}$C$\underline{H_3}$),
δ 3.5-3.9 (b, —NH(C$\underline{H_2}$CH$_2$O)$_{11}$CH$_3$, —NHCH$_2$CONHCH$_2$CONHCH$_2$C$\underline{H_2}$C$_6$H$_4$OH)
δ 3.9-4.3 (s, —NHCH(CH(CH$_3$)(CH$_2$CH$_3$))COOC$\underline{H_2}$CH$_3$, —NHCH$_2$CONC$\underline{H_2}$CONHCH$_2$CH$_2$C$_6$H$_4$OH)
δ 6.7-6.9 (b, —NHCH$_2$CONHCH$_2$CONHCH$_2$CH$_2$C$_6$H$_4$OH),
δ 6.9-7.1 (—NHCH$_2$CONHCH$_2$CONHCH$_2$CH$_2$C$_6$H$_4$OH)

Phosphorus Nuclear Magnetic Resonance Spectrum (CDCl$_3$, ppm): δ 19.8

Average molecular weight (Mw): 113000

Example 26

Preparation of Poly[(isoleucineethylester)(aminomethoxy polyethyleneglycol550)(tyrosine)phosphazene], [NP(IleOEt)$_{1.14}$(AMPEG550)$_{0.69}$(Tyrosine)$_{0.16}$]$_n$ With the same method as in Example 2, 9.26 g of the end product, [NP(IleOEt)$_{1.18}$(AMPEG550)$_{0.62}$(Tyrosine)$_{0.20}$]$_n$ was obtained by using 2.00 g (17.26 mmol) of poly(dichlorophosphazene), 3.04 g (15.52 mmol) of isoleucineethylester, 3.98 g (7.24 mmol) of aminomethoxy polyethyleneglycol having the weight-average molecular weight of 550, 5.43 g (23.45 mmol) of tyrosinemethyl ester, 17.78 g (126.64 mmol) triethylamine, 200 ml of tetrahydrofurane, and 50 ml of acetonitrile. (Yield: 82%)

Hydrogen Nuclear Magnetic Resonance Spectrum (CDCl$_3$, ppm):
δ 0.7-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$),
δ 1.4-1.8 (b, —NHCH(CH(CH$_3$)CH$_2$CH$_3$)OCH$_2$CH$_3$)
δ 2.8-3.1 (b, —NH(C$\underline{H_2}$C$\underline{H_2}$O)$_{11}$CH$_3$)
δ 3.4 (s, —NH(CH$_2$C$\underline{H_2}$O)$_{11}$C$\underline{H_3}$),
δ 3.5-3.9 (b, —NH(C$\underline{H_2}$CH$_2$O)$_{11}$CH$_3$),
δ 3.9-4.3 (s, —N$\underline{H}$CH(CH(CH$_3$)(CH$_2$CH$_3$))COOC$\underline{H_2}$CH$_3$),
δ 4.7 (s, —NHCH(COOH)(C$_6$H$_4$OH)),
δ 6.7-6.9 (b, —N$\underline{H}$CH$_2$CONHCH$_2$CONHCH(COOH)(C$_6$H$_4$OH)),
δ 6.9-7.1 (b, —NHCH$_2$CONHCH$_2$CONHCH(COOH)(C$_6$H$_4$OH))

Phosphorus Nuclear Magnetic Resonance Spectrum (CDCl$_3$, ppm): δ 19.8
Average molecular weight (Mw): 89000

Example 27

Preparation of Poly[(isoleucineethylester)(aminomethoxy polyethyleneglycol550)(glycylglycine)(glycylglycyltyrosinemethylester) phosphazene], [NP(IleOEt)$_{1.15}$(AMPEG550)$_{0.67}$(GlyGlyOH)$_{0.05}$(GlyGlyTyrosine-OMe)$_{0.13}$]$_n$ With the same method as in Example 12, 9.99 g of the end product, [NP(IleOEt)$_{1.15}$(AMPEG550)$_{0.67}$(GlyGlyOH)$_{0.05}$(GlyGlytyramine)$_{0.13}$]$_n$ was obtained by using 2.00 g (17.26 mmol) of poly(dichlorophosphazene), 3.88 g (19.85 mmol) of isoleucineethylester, 1.78 g (6.21 mmol) of glycylglycine allylester trifluoro acetic acid salt, 15.90 g (28.91 mmol) of aminomethoxy polyethyleneglycol having the weight-average molecular weight of 550, 0.72 g (0.62 mmol) of tetrakistriphenylphosphine palladium(0), 5.41 g (62.14 mmol) of morpholine, 0.51 g (4.49 mmol) of cysteamine hydrogen chloride salt, 0.93 g (4.49 mmol) of dicyclohexylcarbodiimide, 0.55 g (4.49 mmol) of dimethylaminopyridine, 16.65 g (164.58 mmol) of triethylamine, 550 ml of tetrahydrofurane, and 100 ml of dichloromethane. (Yield: 76%)

Hydrogen Nuclear Magnetic Resonance Spectrum (CDCl$_3$, ppm):
δ 0.7-1.1 (b, —NHCH(CH(C$\underline{H_3}$)(CH$_2$CH$_3$))COOCH$_2$CH$_3$),
δ 1.1-1.4 (b, —NHCH(CH(CH$_3$)(C$\underline{H_2}$CH$_3$))COOCH$_2$CH$_3$),
δ 1.4-1.8 (b, —NHCH(CH(CH$_3$)CH$_2$CH$_3$)OCH$_2$CH$_3$)
δ 2.8-3.1 (b, —NH($\overline{\text{CH}_2\text{CH}_2\text{O}}$)$_{11}$CH$_3$)
δ 3.4 (s, —NH(CH$_2\overline{\text{CH}_2\text{O}}$)$_{11}$CH$_3$),
δ 3.5-3.9 (b, —NH($\overline{\text{CH}_2}$CH$_2$O)$_{11}$CH$_3$, —NHCH$_2$CONHCH$_2$CONHCH(COO$\overline{\text{H}}$)($\overline{\text{C}_6\text{H}_4\text{OH}}$))
δ 3.9-4.3 (s, —NHCH(CH(CH$_3$)(CH$_2$CH$_3$))COOCH$_2$CH$_3$, —NHCH$_2$CONH$\overline{\text{CH}_2}$CONHCH(COOH)(C$_6$H$_4$OH))
δ 5.7 (s, —NHCH$_2$CONHCH$_2$CONHCH(COOH)(C$_6$H$_4$OH)),
δ 6.7-6.9 (b, —NHCH$_2$CONHCH$_2$CONHCH(COOH)(C$_6\underline{\text{H}_4}$OH)),
δ 6.9-7.1 (b, —NHCH$_2$CONHCH$_2$CONHCH(COOH)(C$_6\underline{\text{H}_4}$OH))
Average molecular weight (Mw): 125000

Example 28

Preparation of Poly[(isoleucineethylester)(aminomethoxy polyethyleneglycol550)(aminoethylsuceinate)(aminoethylmethaerylate) phosphazene],[NP(IleOEt)$_{1.19}$(AMPEG550)$_{0.56}$(aminoethylsuccinate)$_{0.05}$(aminoethyl succinateAEMA)$_{0.20}$]$_n$ 4.05 g (20.71 mmol) of a dried isoleucineethylester hydrogen chloride salt was dissolved in 100 ml of anhydrous tetrahydrofurane, and then 10.10 g (72.48 mmol) of triethylamine was added thereto. To this solution was added dropwise 2.00 g (17.26 mmol) of poly(dichlorophosphazene) dissolved in 50 ml of anhydrous tetrahydrofurane in a dry ice-acetone bath at −60° C., and the resulting mixture was warmed slowly to room temperature to react for 48 hours. After checking the progress of the reaction by $^{31}$P-NMR, 0.31 g (5.18 mmol) of a dried amino ethanol was dissolved in 50 ml of anhydrous tetrahydrofurane, 2.52 g (18.12 mmol) of triethylamine was added thereto, and then the solution was added to the reaction product. Directly after that, a solution prepared by dissolving 4.70 g (8.54 mmol) of a dried aminomethoxy polyethyleneglycol having the weight-average molecular weight of 550 and adding 4.17 g (29.90 mmol) of triethylamine was added dropwise to the reaction product, and then reacted at room temperature for 24 hours and at 40-50° C. for another 24 hours. To the reaction product was then added dropwise a solution prepared by dissolving 2.57 g (4.75 mmol) of a dried amino methoxy polyethylene glycol having the weight-average molecular weight of 550 in 50 ml of anhydrous tetrahydrofurane and adding 2.32 g (16.61 mmol) of triethylamine, and then the resulting mixture reacted at room temperature for 24 hours and at 40-50° C. for another 24 hours.

The reaction solution was filtered to remove the triethylamine hydrochloride salt as generated and the filterate was concentrated under a reduced pressure until a small amount of solvent remained. The concentrate was dissolved in a small amount of methyl alcohol, put into an MWCO 12000 membrane (Spectrum Laboratories, Inc.), subjected to a dialysis with methyl alcohol at room temperature for 5 days and then to a dialysis with distilled water for 5 days, and freeze-dried to give 7.21 g of the poly(dichlorophosphazene) polymer, [NP(IleOEt)$_{1.19}$(AMPEG550)$_{0.55}$(Aminoethanol)$_{0.25}$]$_n$.

7.21 g (5.89 mmol) of the obtained [NP(IleOEt)$_{1.19}$(AMPEG550)$_{0.56}$(Aminoethanol)$_{0.25}$]$_n$ was dissolved in 200 ml of tetrahydrofurane, and reacted at room temperature for 8 hours by using 2 equiv. (1.18 g (11.78 mmol)) of succinic anhydride and 2 equiv. (1.44 g (11.78 mmol)) of dimethylaminopyridine. The reaction filterate was concentrated under a reduced pressure and dissolved in a small amount of methyl alcohol, and then it was subjected to a dialysis with methyl alcohol at room temperature for 5 days and then to a dialysis with distilled water at 4° C. for 5 days, and freeze-dried to give 6.95 g of the end product, [NP(IleOEt)$_{1.23}$(AMPEG550)$_{0.47}$(aminoethylsuccinate)$_{0.30}$]$_n$.

6.95 g of the obtained [NP(IleOEt)$_{1.19}$(AMPEG550)$_{0.56}$(aminoethyl succinate)$_{0.25}$]$_n$ was dissolved in 50 ml of anhydrous dichloromethane and, 0.50 equiv. (1.01 g) of aminoethylmethacrylate, 0.50 equiv. (1.20 g) of dicyclohexylcarbodiimide, 0.60 equiv. (0.84 g) of hydroxysuccinimide, and 2.27 g of tri-n-butyl amine were added thereto to react at 0° C. for 24 hours. The reaction filterate was concentrated under a reduced pressure and dissolved in a small amount of methyl alcohol, and then it was put into an MWCO 6-8000 membrane (Spectrum Laboratories, Inc.), subjected to a dialysis with methyl alcohol at room temperature for 5 days and then to a dialysis with distilled water at 4° C. for 5 days, and freeze-dried to give 6.72 g of the end product, [NP(IleOEt)$_{1.19}$(AMPEG550)$_{0.56}$(Aminoethylsuccinate)$_{0.05}$(Aminoethylsuccinate AEMA)$_{0.20}$]$_n$. (Yield: 89%)

Hydrogen Nuclear Magnetic Resonance Spectrum (CDCl$_3$, ppm):
δ 0.7 to 1.1 (b, —NHCH(CH(CH$_3$)CH$_2$CH$_3$)OCH$_2$CH$_3$),
δ 1.1 to 1.3 (b, —NHCH(CH($\overline{\text{CH}_3}$)CH$_2\overline{\text{CH}_3}$)OCH$_2$CH$_3$),
δ 1.4 to 1.8 (b, —NHCH(CH(CH$_3$)$\overline{\text{CH}_2}$CH$_3$)OCH$_2\overline{\text{CH}_3}$),
δ 1.9 (s, —NHCH$_2$CH$_2$OCOCH$_2$CH$_2$CONHCH$_2$CH$_2$O$_2$C(CH$_3$)C═CH$_2$),
δ 2.5-2.7 (b, —NHCH$_2$CH$_2$OCOCH$_2$CH$_2$CONHCH$_2$CH$_2$O$_2$C(CH$_3$)C═CH$_2$),
δ 2.9-3.2 (b, —NHCH$_2$CH$_2$OCOCH$_2$CH$_2$CONHCH$_2$CH$_2$O$_2$C(CH$_3$)C═CH$_2$),
δ 3.4 (s, —NH(CH$_2$CH$_2$O)$_{11}$CH$_3$),
δ 3.4-3.8 (b, —NH($\overline{\text{CH}_2\text{CH}_2\text{O}}$)$_{11}$CH$_3$), δ 3.9-4.3 (b, —NHCH(CH(CH$_3$)CH$_2$CH$_3$)OCH$_2$CH$_3$, —NHCH$_2$CH$_2$OCOCH$_2$CH$_2$CONHCH$_2$CH$_2$O$_2$C(CH$_3$)C=CH$_2$),
δ 5.5 (s, —NHCH$_2$CH$_2$OCOCH$_2$CH$_2$CONHCH$_2$CH$_2$O$_2$C(CH$_3$)=CH$_2$)
δ 6.1 (s, —NHCH$_2$CH$_2$OCOCH$_2$CH$_2$CONHCH$_2$CH$_2$O$_2$C(CH$_3$)C=CH$_2$)
Phosphorus Nuclear Magnetic Resonance Spectrum (CDCl$_3$, ppm): δ 18.4
Average molecular weight (Mw): 122000

Example 29

Preparation of Poly[(isoleucineethylester)(aminomethoxy polyethyleneglycol550)(aminoethylsuccinate)(aminoethylsuccinatehydroxyethyl methacrylate)phosphazene], [NP(IleOEt)$_{1.19}$(AMPEG550)$_{0.56}$(Aminoethylsuccinate)$_{0.03}$(Aminoethylsuccinate HEMA)$_{0.22}$]$_n$ With the same method of Example 28, 6.86 g of the end product, [NP(IleOEt)$_{1.19}$(AMPEG550)$_{0.56}$(GlyGlyOH)$_{0.03}$(GlyGlyHEMA)$_{0.22}$]$_n$ was obtained by using 2.00 g (17.26 mmol) of poly(dichlorophosphazene), 4.05 g (20.71 mmol) of isoleucineethylester, 7.27 g (13.29 mmol) of aminomethoxy polyethyleneglycol having the weight-average molecular weight of 550, 0.31 g (5.18 mmol) of amino ethanol, 1.16 g (11.63 mmol) of succinic anhydride, 2.24 g (17.74 mmol) of dimethyl aminopyridine, 1.01 g (6.11 mmol) of hydroxyethyl methacrylate, 1.20 g (6.70 mmol) of dicyclohexylcarbodiimide, 0.82 g (6.11 mmol) of dimethylaminopyridine, 16.86 g (166.54 mmol) of triethylamine, 550 ml of tetrahydrofurane, and 100 ml of dichloromethane. (Yield: 77%)
Hydrogen Nuclear Magnetic Resonance Spectrum (CDCl$_3$, ppm):
δ 0.8-1.1 (b, —NHCH(CH(CH$_3$)(CH$_2$CH$_3$))COOCH$_2$CH$_3$),
δ 1.1-1.4 (b, —NHCH(CH(CH$_3$)(CH$_2$CH$_3$))COOCH$_2$CH$_3$),
δ 1.9 (b, —NHCH$_2$CH$_2$O$_2$CCH$_2$CH$_2$CO$_2$CH$_2$CH$_2$O$_2$C(CH$_3$)C=CH$_2$),
δ 2.5 (b, —NHCH$_2$CH$_2$O$_2$CCH$_2$CH$_2$CO$_2$CH$_2$CH$_2$O$_2$C(CH$_3$)C=CH$_2$),
δ 2.8-3.0 (b, —NHCH$_2$CH$_2$O$_2$CCH$_2$CH$_2$CO$_2$CH$_2$CH$_2$O$_2$C(CH$_3$)C=CH$_2$),
δ 3.4 (s, —NH(CH$_2$CH$_2$O)$_{11}$CH$_3$),
δ 3.5-3.9 (b, —NH(CH$_2$CH$_2$O)$_{11}$CH$_3$),
δ 4.0-4.4 (b, —NHCH(CH(CH$_3$)(CH$_2$CH$_3$))COOCH$_2$CH$_3$, —NHCH$_2$CH$_2$O$_2$CCH$_2$CH$_2$CO$_2$CH$_2$CH$_2$O$_2$C(CH$_3$)C=CH$_2$),
δ 5.4 (s, —NHCH$_2$CH$_2$O$_2$CCH$_2$CH$_2$CO$_2$CH$_2$CH$_2$O$_2$C(CH$_3$)C=CH$_2$)
δ 6.0 (s, —NHCH$_2$CH$_2$O$_2$CCH$_2$CH$_2$CO$_2$CH$_2$CH$_2$O$_2$C(CH$_3$)C=CH$_2$)
Phosphorus Nuclear Magnetic Resonance Spectrum (CDCl$_3$, ppm): δ 19.4
Average molecular weight (Mw): 121600

Example 30

Preparation of Poly[(isoleucineethylester)(aminomethoxy polyethyleneglycol550)(aminoethylsuccinate)(aminoethyl succinate cystine ethyl ester)phosphazene], [NP(IleOEt)$_{1.19}$(AMPEG550)$_{0.56}$(Aminoethylsuccinate)$_{0.06}$(AminoethylsuccinateCysOEt)$_{0.19}$]$_n$ With the same method of Example 28, 7.04 g of the end product, [NP(IleOEt)$_{1.19}$(AMPEG550)$_{0.56}$(Aminoethylsuccinate)$_{0.06}$(AminoethylsuccinateCysOEt)$_{0.19}$]$_n$ was obtained by using 2.00 g (17.26 mmol) of poly(dichlorophosphazene), 4.05 g (20.71 mmol) of isoleucineethylester, 7.27 g (13.29 mmol) of aminomethoxy polyethyleneglycol having the weight-average molecular weight of 550, 0.31 g (5.18 mmol) of amino ethanol, 1.19 g (11.90 mmol) of succinic anhydride, 1.45 g (11.90 mmol) of dimethylaminopyridine, 0.40 g (4.14 mmol) of cystineethylester, 1.23 g (6.28 mmol) of dicyclohexylcarbodiimide, 0.60 equiv. (0.87 g, 7.53 mmol) of hydroxysuccinimide, 16.89 g (166.88 mmol) of triethylamine, 550 ml of tetrahydrofurane, 100 ml of dichloromethane. (Yield: 80%)
Hydrogen Nuclear Magnetic Resonance Spectrum (CDCl$_3$, ppm):
δ 0.8-1.1 (b, —NHCH(CH(CH$_3$)(CH$_2$CH$_3$))COOCH$_2$CH$_3$),
δ 1.1-1.4 (b, —NHCH(CH(CH$_3$)(CH$_2$CH$_3$))COOCH$_2$CH$_3$), —NHCH$_2$CH$_2$OCOCH$_2$CH$_2$CONHCH(CH$_2$SH)(COOCH$_2$CH$_3$)),
δ 2.3-2.5 (b, —NHCH$_2$CH$_2$OCOCH$_2$CH$_2$CONHCH(CH$_2$SH)(COOCH$_2$CH$_3$)),
δ 2.9-3.0 (b, —NHCH$_2$CH$_2$OCOCH$_2$CH$_2$CONHCH(CH$_2$SH)(COOCH$_2$CH$_3$)),
δ 3.4 (s, —NH(CH$_2$CH$_2$O)$_{11}$CH$_3$),
δ 3.5-3.9 (b, —NH(CH$_2$CH$_2$O)$_{11}$CH$_3$),
δ 4.0-4.4 (b, —NHCH(CH(CH$_3$)(CH$_2$CH$_3$))COOCH$_2$CH$_3$, —NHCH$_2$CH$_2$OCOCH$_2$CH$_2$CONHCH(CH$_2$SH)(COOCH$_2$CH$_3$))
Phosphorus Nuclear Magnetic Resonance Spectrum (CDCl$_3$, ppm): δ 19.8
Average molecular weight (Mw): 105000

Example 31

Preparation of Poly[(isoleucineethylester)(aminomethoxy polyethyleneglycol550)(aminoethylsuccinate)(aminoethylsuccinatecysteamine) phosphazene],[NP(IleOEt)$_{1.19}$(AMPEG550)$_{0.56}$(Aminoethylsuccinate)$_{0.02}$ (AminoethylsuccinateCysteamine)$_{0.23}$]$_n$ With the same method as in Example 28, 7.04 g of the end product, [NP(IleOEt)$_{1.19}$(AMPEG550)$_{0.56}$(Aminoethylsuccinate)$_{0.02}$(Aminoethylsuccinate Cysteamine)$_{0.23}$]$_n$ was obtained by using 2.00 g (17.26 mmol) of poly(dichlorophosphazene), 4.05 g (20.71 mmol) of isoleucineethylester, 7.27 g (13.29 mmol) of aminomethoxy polyethyleneglycol having the weight-average molecular weight of 550, 0.31 g (5.18 mmol) of amino ethanol, 1.15 g (11.50 mmol) of succinic anhydride, 1.41 g (11.50 mmol) of dimethylaminopyridine, 0.71 g (9.17 mmol) of cysteamine, 1.20 g (6.11 mmol) of dicyclohexylcarbodiimide, 0.84 g (7.34 mmol) of hydroxysuccinimide, 16.89 g (111.38 mmol) of triethylamine, 550 ml of tetrahydrofurane, and 100 ml of dichloromethane. (Yield: 75%)
Hydrogen Nuclear Magnetic Resonance Spectrum (CDCl$_3$, ppm):
δ 0.7-1.1 (b, —NHCH(CH(CH$_3$)CH$_2$CH$_3$)COOCH$_2$CH$_3$),
δ 1.1-1.3 (b, —NHCH(CH(CH$_3$)CH$_2$CH$_3$)COOCH$_2$CH$_3$),
δ 1.4-1.8 (b, —NHCH(CH(CH$_3$)CH$_2$CH$_3$)COOCH$_2$CH$_3$),
δ 2.5-2.7 (b, —NHCH$_2$CH$_2$OCOCH$_2$CH$_2$CONHCH$_2$CH$_2$SH)
δ 2.8-3.2 (b, —NHCH$_2$CH$_2$OCOCH$_2$CH$_2$CONHCH$_2$CH$_2$SH,
δ 3.4 (s, —NH(CH$_2$CH$_2$O)$_{11}$CH$_3$),
δ 3.5 (b, —NHCH$_2$CH$_2$OCOCH$_2$CH$_2$CONHCH$_2$CH$_2$SH,
δ 3.4-3.8 (b, —NH(CH$_2$CH$_2$O)$_{11}$CH$_3$), δ 3.9-4.3 (b, —NHCH(CH(CH$_3$)CH$_2$CH$_3$)COOCH$_2$CH$_3$, —NHCH$_2$CH$_2$OCOCH$_2$CH$_2$CONHCH$_2$CH$_2$SH)

Phosphorus Nuclear Magnetic Resonance Spectrum (CDCl$_3$, ppm): δ 18.2

Average molecular weight (Mw): 85000

Example 32

Preparation of Poly[(isoleucineethylester)(aminomethoxy polyethyleneglycol550)(aminoethylsuceinate)(aminoethylsuccinatetyramine) phosphazene], [NP(IleOEt)$_{1.19}$(AMPEG550)$_{0.56}$(Aminoethylsuccinate)$_{0.04}$(AminoethylsuccinateTyr amine)$_{0.21}$]$_n$ With the same method of Example 28, 7.30 g of the end product, [NP(IleOEt)$_{1.19}$(AMPEG550)$_{0.56}$(Aminoethylsuccinate)$_{0.04}$(AminoethylsuccinateTyramine)$_{0.21}$]$_n$ was obtained by using 2.00 g (17.26 mmol) of poly(dichlorophosphazene), 4.05 g (20.71 mmol) of isoleucineethylester, 7.27 g (13.29 mmol) of aminomethoxy polyethyleneglycol having the weight-average molecular weight of 550, 0.31 g (5.18 mmol) of amino ethanol, 1.15 g (11.50 mmol) of succinic anhydride, 1.41 g (11.50 mmol) of dimethylaminopyridine, 0.84 g (6.11 mmol) of tyramine, 1.20 g (6.11 mmol) of dicyclohexylcarbodiimide, 0.84 g (7.34 mmol) of hydroxysuccinimide, 20.35 g (123.61 mmol) of triethylamine, 550 ml of tetrahydrofurane, and 100 ml of dichloromethane. (Yield: 79%)

Hydrogen Nuclear Magnetic Resonance Spectrum (CDCl$_3$, ppm):

δ 0.7-1.1 (b, —NHCH(CH(CH$_3$)(CH$_2$CH$_3$))COOCH$_2$CH$_3$),

δ 1.1-1.4 (b, —NHCH(CH(CH$_3$)(CH$_2$CH$_3$))COOCH$_2$CH$_3$),

δ 1.4-1.8 (b, —NHCH(CH(CH$_3$)(CH$_2$CH$_3$)COOCH$_2$CH$_3$)

δ 2.4-2.8 (b, —NHCH$_2$CH$_2$OCOCH$_2$CH$_2$CONHCH$_2$CH$_2$C$_6$H$_4$OH)

δ 2.8-3.1 (b, —NH(CH$_2$CH$_2$O)$_{11}$CH$_3$), —NHCH$_2$CH$_2$OCOCH$_2$CH$_2$CONHCH$_2$CH$_2$C$_6$H$_4$OH)

δ 3.4 (s, —NH(CH$_2$CH$_2$O)$_{11}$CH$_3$),

δ 3.5-3.9 (b, —NH(CH$_2$CH$_2$O)$_{11}$CH$_3$,

δ 3.9-4.3 (s, —NHCH(CH(CH$_3$)(CH$_2$CH$_3$))COOCH$_2$CH$_3$, —NHCH$_2$CH$_2$OCOCH$_2$CH$_2$CONHCH$_2$CH$_2$C$_6$H$_4$OH)

δ 6.7-6.9 (b, —NHCH$_2$CONHCH$_2$CH$_2$C$_6$H$_4$OH),

δ 6.9-7.1(—NHCH$_2$CONHCH$_2$CONHCH$_2$CH$_2$C$_6$H$_4$OH)

Phosphorus Nuclear Magnetic Resonance Spectrum (CDCl$_3$, ppm): δ 19.8

Average molecular weight (Mw): 98000

Example 33

Preparation of Poly[(isoleucineethylester)(aminomethoxy polyethyleneglycol550)(aminoethyl succinate)(iminoethylsuccinate tyrosinemethyl ester) phosphazene],[NP(IleOEt)$_{1.19}$(AMPEG550)$_{0.56}$(Aminoethylsuccinate)$_{0.07}$(AminoethylsuccinateTyrosine-OMe)$_{0.18}$]$_n$ With the same method of Example 28, 7.01 g of the end product, [NP(IleOEt)$_{1.19}$(AMPEG550)$_{0.56}$(Aminoethylsuccinate)$_{0.07}$(AminoethylsuccinateTyrosin eOMe)$_{1.18}$]$_n$ was obtained by using 2.00 g (17.26 mmol) of poly(dichlorophosphazene), 4.05 g (20.71 mmol) of isoleucineethylester, 7.27 g (13.29 mmol) of aminomethoxy polyethyleneglycol having the weight-average molecular weight of 550, 0.31 g (5.18 mmol) of amino ethanol, 1.15 g (11.50 mmol) of succinic anhydride, 1.41 g (11.50 mmol) of dimethylaminopyridine, 1.21 g (6.18 mmol) of tyrosinemethyl ester, 1.21 g (6.18 mmol) of dicyclohexylcarbodiimide, 0.85 g (7.42 mmol) of hydroxysuccinimide, 20.36 g (123.75 mmol) of triethylamine, 550 ml of tetrahydrofurane, and 100 ml of dichloromethane. (Yield: 75%)

Hydrogen Nuclear Magnetic Resonance Spectrum (CDCl$_3$, ppm):

δ 0.7-1.1 (b, —NHCH(CH(CH$_3$)(CH$_2$CH$_3$))OCH$_2$CH$_3$),

δ 1.1-1.4 (b, —NHCH(CH(CH$_3$)(CH$_2$CH$_3$))OCH$_2$CH$_3$),

δ 1.4-1.8 (b, —NHCH(CH(CH$_3$)CH$_2$CH$_3$)OCH$_2$CH$_3$)

δ 2.4-2.8 (b, —NHCH$_2$CH$_2$OCOCH$_2$CH$_2$CONHCH(COOH)(C$_6$H$_4$OH))

δ 2.8-3.1 (b, —NH(CH$_2$CH$_2$O)$_{11}$CH$_3$), NHCH$_2$CH$_2$OCOCH$_2$CH$_2$CONNHCH(COOH)(C$_6$H$_4$OH))

δ 3.4 (s, —NH(CH$_2$CH$_2$O)$_{11}$CH$_3$),

δ 3.5-3.9 (b, —NH(CH$_2$CH$_2$O)$_{11}$CH$_3$,

δ 3.9-4.3 (s, —NHCH(CH(CH$_3$)(CH$_2$CH$_3$))COOCH$_2$CH$_3$, —NHCH$_2$CH$_2$OCOCH$_2$CH$_2$CONHCH(COOH)(C$_6$H$_4$OH))

δ 5.7 (s, —NHCH$_2$CH$_2$OCOCH$_2$CH$_2$CONHCH(COOH)(C$_6$H$_4$OH)),

δ 6.7-6.9 (b, —NHCH$_2$CH$_2$OCOCH$_2$CH$_2$CONHCH(COOH)(C$_6$H$_4$OH)),

δ 6.9-7.1 (b, —NHCH$_2$CH$_2$OCOCH$_2$CH$_2$CONHCH(COOH)(C$_6$H$_4$OH))

Phosphorus Nuclear Magnetic Resonance Spectrum (CDCl$_3$, ppm): δ 19.8

Average molecular weight (Mw): 113000

Example 34

Poly[(isoleucineethylester)(aminomethoxy polyethyleneglycol550)(aminoethylmethacrylate)(CRGD) phosphazene], [NP(IleOEt)$_{1.01}$(AMPEG550)$_{0.64}$(AEMA)$_{0.30}$(CRGD)$_{0.05}$]$_n$ 2.00 g (3.32 mmol) of a dried polymer of Example 1, [NP(IleOEt)$_{1.01}$(AMPEG550)$_{0.64}$(AEMA)$_{0.35}$]$_n$ was dissolved in 100 ml of distilled water, and then 0.09 mg (0.2 mmol) of (cysteine-RGD; CRGD) was added thereto and dissolved. To the resulting solution was then added 0.1N NaOH solution to adjust the pH to 8.4, and then reacted at room temperature for 16 hours.

The reaction solution was concentrated under a reduced pressure until a small amount of solvent remained, and then it was precipitated with an addition of 2M NaCl solution. This procedure was repeated two to three times, and then the precipitate was dissolved again in a small amount of distilled water, put into an MWCO 12000 membrane (Spectrum Laboratories, Inc.), and subjected to a dialysis with distilled water for 5 days, and then it was freeze-dried to give 1.85 g of the poly(dichlorophosphazene) polymer, [NP(IleOEt)$_{1.01}$(AMPEG550)$_{0.64}$(AEMA)$_{0.30}$(RGD)$_{0.05}$]$_n$. (Yield: 89%)

Hydrogen Nuclear Magnetic Resonance Spectrum (DMSO-d$_6$, ppm):

δ 0.8-1.1 (b, —NHCH(CH(CH$_3$)(CH$_2$CH$_3$))COOCH$_2$CH$_3$),

δ 1.1-1.4 (b, —NHCH(CH(CH$_3$)(CH$_2$CH$_3$))COOCH$_2$CH$_3$),

δ 1.9 (s, —NHCH$_2$CH$_2$O$_2$C(CH$_3$)C═CH$_2$)

δ 3.4 (s, —NH(CH$_2$CH$_2$O)$_{11}$CH$_3$),

δ 3.5-3.9 (b, —NH(CH$_2$CH$_2$O)$_{11}$CH$_3$, —NHCH(CH(CH$_3$)(CH$_2$CH$_3$))COOCH$_2$CH$_3$),

δ 4.0-4.4 (b, —NHCH(CH($CH_3$)($CH_2CH_3$))COO$CH_2CH_3$, —NH$CH_2CH_2O_2$C($CH_3$)C=$CH_2$),
δ 5.5 (s, —NH$CH_2CH_2O_2$C($CH_3$)C=$CH_2$)
δ 6.1 (s, —NH$CH_2CH_2O_2$C($CH_3$)C=$CH_2$)
δ 8.1-8.7 (b, Guanidine group of CRGD)
Phosphorus Nuclear Magnetic Resonance Spectrum ($CDCl_3$, ppm): δ 19.7
Average molecular weight (Mw): 547000

Example 35

Preparation of Poly[(isoleucineethylester)(aminomethoxy polyethyleneglycol550)(acrylate)(CRGD)phosphazene], [NP(IleOEt)$_{1.09}$(AMPEG550)$_{0.46}$(Acrylate)$_{0.38}$(CRGD)$_{0.07}$]$_n$ 2.00 g (3.84 mmol) of a dried polymer of Example 9, [NP(IleOEt)$_{1.09}$(AMPEG550)$_{0.46}$(Acrylate)$_{0.45}$]$_n$ was dissolved in 100 ml of distilled water, and 0.14 mg (0.31 mmol) of (cysteine-RGD; CRGD) was added thereto to react at room temperature for four hours.

The reaction solution was concentrated under a reduced pressure until a small amount of solvent remained, and was precipitated with an addition of 2M NaCl solution. This procedure was repeated two to three times, and then the precipitate was dissolved again in a small amount of distilled water, put into an MWCO 12000 membrane (Spectrum Laboratories, Inc.), and subjected to a dialysis with distilled water for 5 days, and then it was freeze-dried to give 1.85 g of the poly(dichlorophosphazene) polymer, [NP(IleOEt)$_{1.09}$(AMPEG550)$_{0.46}$(Acrylate)$_{0.38}$(CRGD)$_{0.07}$]$_n$. (Yield: 90%)

Hydrogen Nuclear Magnetic Resonance Spectrum (DMSO-$d_6$, ppm):
δ 0.91-1.05 (s, —NHCH(CH($\underline{CH_3}$)($CH_2CH_3$))COO$CH_2CH_3$),
δ 1.05-1.40 (b, —NHCH(CH($CH_3$)($CH_2CH_3$))COO$CH_2CH_3$)
δ 1.40-1.62 (b, —NHCH(CH($CH_3$)($\underline{CH_2CH_3}$))COO$CH_2CH_3$)
δ 1.62-1.85 (b, —NHCH(CH($CH_3$)($CH_2CH_3$))COO$CH_2CH_3$)
δ 2.80-3.18 (b, —NH$\underline{CH_2}CH_2$O— and —NH$CH_2CH_2$COCH$CH_2$)
δ 3.38 (s, —NH($CH_2CH_2$O)$_{11}CH_3$),
δ 3.50-3.91 (b, 44H), —NH($\overline{CH_2CH_2}$O)$_{11}CH_3$
δ 3.91-4.00 (b, —NHCH(CH($CH_3$)($CH_2CH_3$))COO$CH_2CH_3$ and —NH$CH_2$COCHCH$_2$)
δ 4.11-4.40 (b, —NHCH(CH($CH_3$)($CH_2CH_3$))COO$CH_2CH_3$)
δ 5.82 (t, 1H), —NH$CH_2CH_2$COCH$CH_2$)
δ 6.2 (S, 1H), —NH$CH_2CH_2$COCH$\overline{CH_2}$)
δ 6.42 (d, 1H), —NH$CH_2CH_2$$\overline{CO}$CH$CH_2$)
δ 8.1-8.7 (b, Guanidine group of $\overline{CRGD}$)
Phosphorus Nuclear Magnetic Resonance Spectrum ($CDCl_3$, ppm): δ 19.9
Average molecular weight (Mw): 446000

Example 36

Preparation of Poly[(isoleueineethylester)(aminomethoxy polyethyleneglycol550)(cysteamine)(CRGD)phosphazene], [NP(IleOEt)$_{0.88}$(AMPEG550)$_{0.54}$(cysteamine)$_{0.53}$(CRGD)$_{0.05}$]$_n$ 2.00 g (3.81 mmol) of a dried polymer of Example 21, [NP(IleOEt)$_{0.88}$(AMPEG550)$_{0.54}$(cysteamine)$_{0.58}$], was dissolved in 100 ml of distilled water and then 0.13 mg (0.3 mmol) of (cysteine-RGD; CRGD) was added thereto and dissolved. To the resulting solution was then added 0.1N NaOH solution to adjust the pH to 8.4, and the resulting mixture reacted at room temperature for 24 hours.

The reaction solution was concentrated under a reduced pressure until a small amount of solvent remained, and was precipitated with an addition of 2M NaCl solution. This procedure was repeated two to three times, and then the precipitate was dissolved again in a small amount of distilled water, put into an MWCO 12000 membrane (Spectrum Laboratories, Inc.), and subjected to a dialysis with distilled water for 5 days, and then it was freeze-dried to give 1.83 g of the poly(dichlorophosphazene) polymer, [NP(IleOEt)$_{0.88}$(AMPEG550)$_{0.54}$(cysteamine)$_{0.53}$(CRGD)$_{0.05}$]$_n$. (Yield: 87%)

Hydrogen Nuclear Magnetic Resonance Spectrum (DMSO-$d_6$, ppm):
δ 0.8-1.1 (b, —NHCH(CH($\underline{CH_3}$)($CH_2CH_3$))COO$CH_2CH_3$),
δ 1.1-1.4 (b, —NHCH(CH($CH_3$)($CH_2CH_3$))COO$CH_2CH_3$),
δ 1.4-1.6 (b, —NHCH(CH($CH_3$)($CH_2CH_3$))COO$CH_2CH_3$, —NH$CH_2CH_2$SH),
δ 1.6-1.9 (b, —NHCH(CH($CH_3$)($CH_2CH_3$))COO$CH_2CH_3$),
δ 2.6-2.8 (b, —NH$CH_2CH_2$SH),
δ 2.9-3.3 (b, —N$\overline{H}CH_2CH_2$SH), (s, —NH$CH_2CH_2$O($CH_2CH_2$O)$_{10}CH_3$),
δ 3.4 (s, —NH($CH_2$$\overline{CH_2O}$)$_{11}CH_3$),
δ 3.5-3.9 (b, —NH($\overline{CH_2}CH_2$O)$_{11}CH_3$, —NHCH(CH($CH_3$)($CH_2CH_3$))COO$\overline{CH_2CH_3}$),
δ 4.0-4.4 (b, —NHCH(CH($CH_3$)($CH_2CH_3$))COO$CH_2CH_3$)
δ 8.1-8.7 (b, Guanidine group of CRGD)
Phosphorus Nuclear Magnetic Resonance Spectrum ($CDCl_3$, ppm): δ 19.8
Average molecular weight (Mw): 352000

Example 37

Preparation of Poly[(isoleucineethylester)(aminomethoxy polyethyleneglycol550)(vinylsulfone)phosphazene], [NP(IleOEt)$_{1.09}$(AMPEG550)$_{0.45}$(vinylsulfone)$_{0.46}$]$_n$ 6.41 g (32.75 mmol) of a dried isoleucineethylester hydrogen chloride salt was dissolved in 100 ml of anhydrous tetrahydrofurane, and 9.94 g (98.27 mmol) of triethylamine was added thereto. To the resulting solution was then added dropwise 4.00 g (34.48 mmol) of poly(dichlorophosphazene) dissolved in 100 ml of anhydrous tetrahydrofurane in a dry ice-acetone bath at −60° C., and then the resulting mixture was slowly warmed to room temperature to react for 48 hours.

After checking the progress of the reaction by $^{31}$P-NMR, a solution prepared by dissolving 7.58 g (13.79 mmol) of a dried aminomethoxy polyethyleneglycol having the weight-average molecular weight of 550 in 50 ml of anhydrous tetrahydrofurane and adding 4.18 g (41.37 mmol) of triethylamine was added dropwise to the reaction product, and then the resulting mixture reacted at room temperature for 24 hours and 40 to 50° C. for another 24 hours.

After that, the reaction solution was added dropwise to an amino ethanol solution prepared by adding 4.10 g (67.24 mmol) of a dried amino ethanol and 6.8 g (67.24 mmol) of triethylamine to 100 ml of anhydrous tetrahydrofurane and dissolving them, and then reacted at room temperature for 24 hours and 40 to 50° C. for another 24 hours.

The reaction solution was filtered to remove the triethylamine hydrochloride salt as generated and the filtrate was concentrated under a reduced pressure until a small amount of solvent remained. The concentrate was dissolved in a small amount of methyl alcohol, and then it was put into an MWCO 12000 membrane (Spectrum Laboratories, Inc.), subjected to a dialysis with methyl alcohol at room temperature for five days and then to a dialysis with distilled water for five days, and then freeze-dried to give 11.32 g of the poly(dichlorophosphazene) polymer, [NP(IleOEt)$_{1.19}$(AMPEG550)$_{0.55}$(Aminoethanol)$_{0.25}$]$_n$. (yield: 76%).

2.3 g (2.1 mmol) of the obtained [NP(IleOEt)$_{1.19}$(AMPEG550)$_{0.56}$(Aminoethanol)$_{0.25}$]$_n$ was dissolved in 50 ml of tetrahydrofurane, and a solution of 0.43 g (4.3 mmol) of triethylamine was added dropwise thereto, and then stirred at 0° C. for 15 minutes. To this solution was added dropwise a solution prepared by stirring vinyl sulfone and thioglycolic acid at a mole ratio of 20:1 at a temperature of 37° C. for 8 hours. To this reaction solution was added dropwise a solution prepared by dissolving 1.34 g (6.4 mmol) of N,N'-dicyclohexyl carbodiimide and 0.95 g (7.7 mmol) of 4-(dimethylamino)pyridine in 50 ml of tetrahydrofurane, and then the mixture was stirred for 48 hours. After that, the reaction solution was filtered and concentrated under a reduced pressure, and then a mixed solution of chloroform and diethylether (50:50) was added thereto to precipitate N,N'-dicyclohexyl urea, which was tilted and removed. The filtered solution was concentrated under a reduced pressure and this concentrate was dissolved in a small amount of methyl alcohol, put into an MWCO 12000 membrane (Spectrum Laboratories, Inc.), and subjected to a dialysis with methyl alcohol at room temperature for 4 days and then to a dialysis with distilled water for 4 days, and then it was freeze-dried to give 2.01 g of the poly(dichlorophosphazene) polymer, [NP(IleOEt)$_{1.19}$(AMPEG550)$_{0.55}$ (Aminoethanol)$_{0.25}$]$_n$. (Yield: 67%)

Hydrogen Nuclear Magnetic Resonance Spectrum (CDCl$_3$, ppm):

δ 0.8-1.1 (b, —NHCH(CH(C$\underline{H_3}$)(CH$_2$CH$_3$))COOCH$_2$CH$_3$),

δ 1.1-1.4 (b, —NHCH(CH(CH$_3$)(CH$_2$CH$_3$))COOCH$_2$C$\underline{H_3}$),

δ 1.4-1.6 (b, —NHCH(CH(CH$_3$)(C$\underline{H_2}$CH$_3$))COOCH$_2$CH$_3$),

δ 1.6-1.9 (b, —NHCH(C$\underline{H}$(CH$_3$)(CH$_2$CH$_3$))COOCH$_2$CH$_3$),

δ 2.2-2.6 (b, —CH$_2$—S—C$\underline{H_2}$—CH$_2$— of vinylsulfone ethylthioacetate), δ 2.80-3.18 (b, —NHC$\underline{H_2}$CH$_2$O, —NH—C$\underline{H_2}$—CH$_2$— of Amino ethyl vinyl sulfone ethylthioacetate), δ 3.4 (s, —NH(CH$_2$CH$_2$O)$_{11}$C$\underline{H_3}$), δ 3.50-3.91 (b, —NH(C$\underline{H_2}$C$\underline{H_2}$O)$_{11}$CH$_3$, s, of —CH$_2$—S—C$\underline{H_2}$—CH$_2$— of vinyl sulfone ethylthioacetate), δ 3.91-4.00 (b, 1H, —NHC$\underline{H}$(CH(CH$_3$)(CH$_2$CH$_3$))COOCH$_2$CH$_3$), δ 4.11-4.40 (b, NHCH(CH(CH$_3$)(CH$_2$CF$_{13}$))COOC$\underline{H_2}$CH$_3$, —NH—CH$_2$—C$\underline{H_2}$— of Amino ethyl vinyl sulfone ethylthioacetate), δ 6.20 (S, C$\underline{H_2}$═CH-Amino ethyl vinyl sulfone ethylthioacetate) of AEMA), δ 6.40 (S, C$\underline{H_2}$═CH-Amino ethyl vinyl sulfone ethylthioacetate), δ 6.40 (S, CH$_2$═C$\underline{H}$-Amino ethyl vinyl sulfone ethylthioacetate).

Phosphorus Nuclear Magnetic Resonance Spectrum (CDCl$_3$, ppm): δ 19.8

Average molecular weight (Mw): 421000

Example 38

Preparation of Poly[(isoleucineethylester)(aminomethoxy polyethyleneglycol550)(vinylsulfone)(CRGD)phosphazene], [NP(IleOEt)$_{1.09}$(AMPEG550)$_{0.45}$(vinylsulfone)$_{0.36}$(CRGD)$_{0.10}$]$_n$ 0.5 g of a dried polymer of Example 37, [NP(IleOEt)$_{1.09}$(AMPEG550)$_{0.45}$(vinylsulfone)$_{0.46}$]$_n$ was dissolved in 10 ml of a phosphate buffered solution (PBS), and 47 mg of cysteine-RGD (CRGD) was added thereto and then the resulting mixture reacted at 50° C. for 24 hours.

After that, the reaction solution was put into an MWCO 12000 membrane (Spectrum Laboratories, Inc.) and subjected to a dialysis with distilled water for 5 days, and then it was freeze-dried to give 0.42 g of the poly(dichlorophosphazene) polymer, [NP(IleOEt)$_{1.09}$(AMPEG550)$_{0.45}$(vinylsulfone)$_{0.36}$(CRGD)$_{0.10}$]$_n$. (Yield: 77%)

Hydrogen Nuclear Magnetic Resonance Spectrum (DMSO-d$_6$, ppm):

δ 0.8-1.1 (b, —NHCH(CH(C$\underline{H_3}$)(CH$_2$CH$_3$))COOCH$_2$CH$_3$),

δ 1.1-1.4 (b, —NHCH(CH(CH$_3$)(CH$_2$CH$_3$))COOCH$_2$C$\underline{H_3}$),

δ 1.4-1.6 (b, —NHCH(CH(CH$_3$)(C$\underline{H_2}$CH$_3$))COOCH$_2$CH$_3$),

δ 1.6-1.9 (b, —NHCH(C$\underline{H}$(CH$_3$)(CH$_2$CH$_3$))COOCH$_2$CH$_3$),

δ 2.2-2.6 (b, —CH$_2$—S—C$\underline{H_2}$—CH$_2$— of vinylsulfone ethylthioacetate), δ 2.80-3.18 (b, —NHC$\underline{H_2}$CH$_2$O, —NH—C$\underline{H_2}$—CH$_2$— of Amino ethyl vinyl sulfone ethylthioacetate), δ 3.4 (s, —NH(CH$_2$CH$_2$O)$_{11}$C$\underline{H_3}$), δ 3.50-3.91 (b, —NH(C$\underline{H_2}$C$\underline{H_2}$O)$_{11}$CH$_3$, s, of —CH$_2$—S—C$\underline{H_2}$—CH$_2$— of vinyl sulfone ethylthioacetate), δ 3.91-4.00 (b, 1H, —NHC$\underline{H}$(CH(CH$_3$)(CH$_2$CH$_3$))COOCH$_2$CH$_3$), δ 4.11-4.40 (b, NHCH(CH(CH$_3$)(CH$_2$CH$_3$))COOC$\underline{H_2}$CH$_3$, —NH—CH$_2$—C$\underline{H_2}$— of Amino ethyl vinyl sulfone ethylthioacetate), δ 6.20 (S, C$\underline{H_2}$═CH-Amino ethyl vinyl sulfone ethylthioacetate) of AEMA), δ 6.40 (S, C$\underline{H_2}$═CH-Amino ethyl vinyl sulfone ethylthioacetate), δ 6.40 (S, CH$_2$═C$\underline{H}$-Amino ethyl vinyl sulfone ethylthioacetate).

Phosphorus Nuclear Magnetic Resonance Spectrum (CDCl$_3$, ppm): ☐ 19.8

Average molecular weight (Mw): 432000

Example 39

Observation of the Sol-Gel Transition of the Poly(Organophosphazene)s Depending on a Temperature Change Each of the poly(organophosphazene)s of the present invention obtained in Examples 1 to 27 was dissolved in a phosphate buffered saline solution (pH 7.4) at 4° C. with a concentration of 10 wt %, respectively. Each of the solutions was placed in a chamber of a viscometer (Brookfield DV-III+ Rheometer) equipped with a thermostatic bath (TC-501), and then heated at a rate of 0.04° C. per a minute with a shear rate of 0.1-1.7 per a second to observe its sol-gel behavior dependant on a temperature.

FIG. 1 is a photograph showing the sol-gel behavior of the poly(organophosphazene)s of the present invention depending on a temperature change. It shows that at a temperature below the initial gelling temperature, it was in a flowing solution phase, but at the maximum gelling temperature, it was in a gel phase.

The following Table 2 showed the experimental results of the gel properties of the thermosensitive poly(organophosphazene)s of the present invention depending on a temperature change.

Example 40

Preparation of the Hydrogel Crosslinked by Using UV Radiation and the Poly(Organophosphazene) Having a Vinyl Substituent A hydrogel was prepared at 37° C. by putting into a millicell a solution prepared by dissolving the poly(organophos-

TABLE 2

Results of experiment for the gel properties of the poly(organophosphazene)s depending on a change in a temperature

| Polymer | Structure | Max. Gelling Temp. (° C.) | Max. Gel solidity (Pa·s) |
|---|---|---|---|
| Example 1 | $[NP(IleOEt)_{1.01}(AMPEG550)_{0.64}(AEMA)_{0.35}]_n$ | 39 | 270 |
| Example 2 | $[NP(IleOEt)_{1.16}(AMPEG550)_{0.60}(AEMA)_{0.23}]_n$ | 33 | 977 |
| Example 3 | $[NP(IleOEt)_{1.21}(AMPEG550)_{0.57}(AEMA)_{0.21}]_n$ | 28 | 1547 |
| Example 4 | $[NP(IleOEt)_{1.23}(AMPEG550)_{0.61}(AEMA)_{0.15}]_n$ | 28 | 587 |
| Example 5 | $[NP(IleOEt)_{1.17}(AMPEG550)_{0.68}(AEMA)_{0.14}]_n$ | 39 | 198 |
| Example 6 | $[NP(IleOEt)_{1.17}(AMPEG750)_{0.55}(AEMA)_{0.28}]_n$ | 54 | 40 |
| Example 7 | $[NP(IleOEt)_{1.23}(AMPEG550)_{0.61}(HEMA)_{0.15}]_n$ | 37 | 115 |
| Example 8 | $[NP(IleOEt)_{1.04}(AMPEG750)_{0.74}(HEMA)_{0.22}]_n$ | — | — |
| Example 9 | $[NP(IleOEt)_{1.09}(AMPEG550)_{0.46}(Acrylate)_{0.45}]_n$ | 38 | 115 |
| Example 10 | $[NP(IleOEt)_{0.91}(AMPEG550)_{0.66}(Acrylate)_{0.43}]_n$ | — | — |
| Example 11 | $[NP(IleOEt)_{1.23}(AMPEG750)_{0.42}(Acrylate)_{0.35}]_n$ | 48 | 150 |
| Example 12 | $[NP(IleOEt)_{1.27}(AMPEG550)_{0.51}(GlyGlyOH)_{0.09}(GlyGlyAEMA)_{0.13}]_n$ | 18 | 1417 |
| Example 13 | $[NP(IleOEt)_{1.29}(AMPEG550)_{0.54}(GlyGlyOH)_{0.02}(GlyGlyHEMA)_{0.15}]_n$ | 25 | 807 |
| Example 14 | $[NP(IleOEt)_{1.21}(AMPEG550)_{0.64}(CysOEt)_{0.15}]_n$ | 32 | 218 |
| Example 15 | $[NP(IleOEt)_{0.96}(AMPEG550)_{0.78}(CysOEt)_{0.24}]_n$ | — | — |
| Example 16 | $[NP(IleOEt)_{1.02}(AMPEG750)_{0.43}(CysOEt)_{0.54}]_n$ | 42 | 392 |
| Example 17 | $[NP(IleOEt)_{1.12}(AMPEG550)_{0.73}(GlyLacOEt)_{0.06}(CysOEt)_{0.09}]_n$ | 38 | 82 |
| Example 18 | $[NP(IleOEt)_{1.15}(AMPEG550)_{0.60}(GlyLacOEt)_{0.09}(GlyCysOEt)_{0.16}]_n$ | 35 | 526 |
| Example 19 | $[NP(IleOEt)_{1.19}(AMPEG550)_{0.64}(GlyGlyOH)_{0.05}(GlyGlyCysOEt)_{0.12}]_n$ | 30 | 97 |
| Example 20 | $[NP(IleOEt)_{1.18}(AMPEG550)_{0.62}(Cysteamine)_{0.20}]_n$ | 40 | 248 |
| Example 21 | $[NP(IleOEt)_{0.88}(AMPEG550)_{0.54}(Cysteamine)_{0.58}]_n$ | 38 | 312 |
| Example 22 | $[NP(IleOEt)_{0.74}(AMPEG550)_{0.49}(Cysteamine)_{0.77}]_n$ | 42 | 345 |
| Example 23 | $[NP(IleOEt)_{1.16}(AMPEG550)_{0.62}(GlyGlyOH)_{0.05}(GlyGlycysteamine)_{0.17}]_n$ | 29 | 411 |
| Example 24 | $NP(IleOEt)_{1.14}(AMPEG550)_{0.68}(Tyramine)_{0.17}]_n$ | 34 | 215 |
| Example 25 | $NP(IleOEt)_{1.16}(AMPEG550)_{0.62}(GlyGlyOH)_{0.05}(GlyGlyTyramine)_{0.17}]_n$ | 33 | 520 |
| Example 26 | $NP(IleOEt)_{1.10}(AMPEG550)_{0.76}(TyrosineOMe)_{0.14}]_n$ | 30.8 | 215 |
| Example 27 | $NP(IleOEt)_{1.16}(AMPEG550)_{0.62}(GlyGlyOH)_{0.05}(GlyGlyTyrosineOMe)_{0.17}]_n$ | 28 | 405 |

In Table 2, the 'maximum gelling temperature' refers to a temperature at which the viscosity of the polymer solution reaches its highest point, while the maximum gel solidity refers to the maximum value of the viscosity of the polymer solution.

Figure 2:
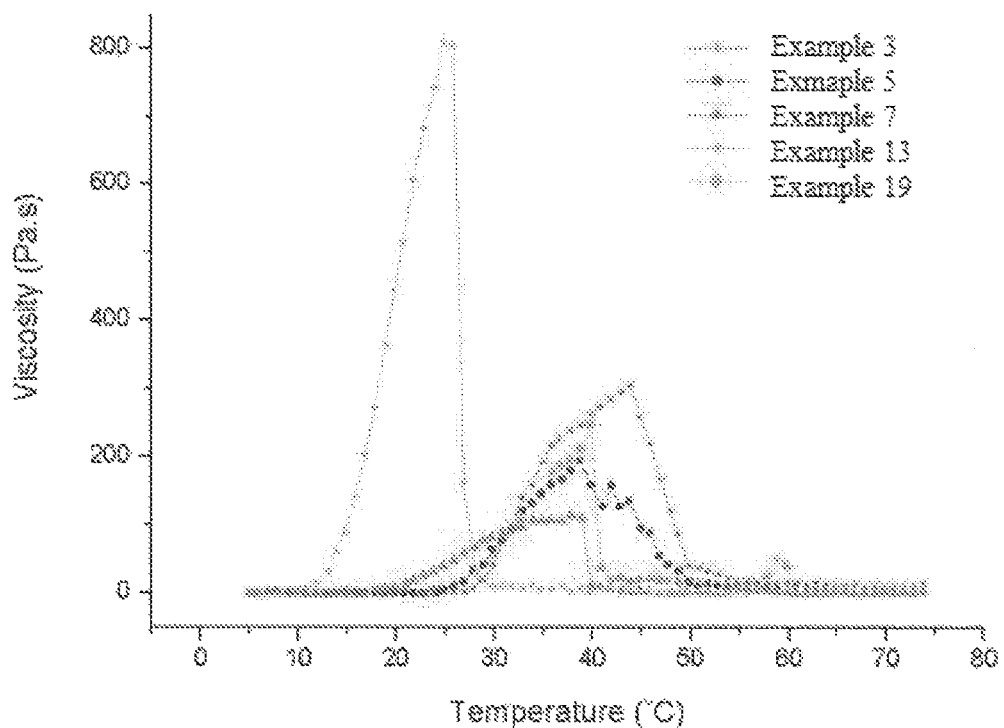
FIG. 2 is a graph plotting the viscosity change dependant on a temperature change for the solution of the crosslinkable, thermosensitive poly(organophosphazene) in accordance with an embodiment of the present invention.

FIG. 2 shows that the viscosity of the poly(organophosphazene) of the present invention varied with a temperature.

As known from Table 2 and FIG. 2, it was found that the poly(organophosphazene) can have a wide range of the maximum gelling temperature and the maximum gel solidity by controlling the types of the hydrophobic amino acid ester substituted at the poly(organophosphazene), the types of the amino acid, the peptide, the desipeptide that can control a degradation rate, the types of the crosslinkable substituents, the length of the methoxy polyethyleneglycol chains, and the composition of all the substituents.

In addition, although the poly(organophosphazene)s of Example 8, Example 10, and Example 15 had a thiol group or a vinyl group capable of UV exposure and forming the crosslinkings, their viscosity did not vary with a temperature because they comprised a large amount of methoxy polyethylene glycol.

phazene) of Example 5 in a phosphate buffered saline solution at a concentration of 10 wt %. Also, a hydrogel was prepared at 37° C. by putting a phosphate buffered saline solution of 10 wt % of the poly(organophosphazene) of Example 5 (10 wt %) comprising 1 wt % of a photoinitiator, 2,2-diphenyl-1-pycrylhydrazyl into a millicell and was irradiated with 365 nm of UV radiation at 37° C. for one minute to prepare a crosslinked hydrogel of the poly(organophosphazene).

As shown in FIG. 1, the phosphazene polymer hydrogel crosslinked by UV exposure maintained its gel phase even at a decreased temperature since it kept its network structure by the crosslinkings. However, with decreasing a temperature, the poly(organophosphazene) hydrogel with no crosslinking lost its network structure that had been maintained at 37° C. and turned into a solution.

Figure 3:
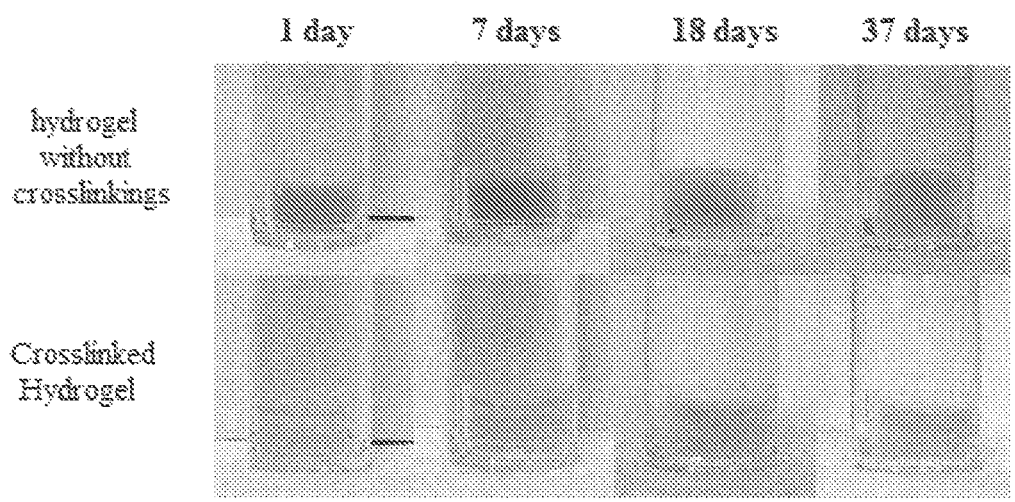
FIG. 3 is a photograph showing a change in swelling of the crosslinked, poly(organophosphazene) hydrogel over time according to an embodiment of the present invention.

FIG. 3 shows the swelling ratio of the hydrogel over time as each of the millicells containing the poly(organophosphazene) hydrogel with no crosslinking and the crosslinked hydrogel of the poly(organophosphazene) was immersed in 10 ml of a phosphate buffered saline solution at 37° C.

As shown in FIG. 3, the hydrogel without crosslinking swelled up to be bulky as time passed, while the crosslinked hydrogel maintained substantially its original volume even after 37 days.

Example 41

Preparation of the Hydrogel Crosslinked at a Body Temperature by UV Irradiation onto a Solution of Poly(Organophosphazene)s Having a Methacrylate Substituent at a Low Temperature In a conventional polymer having a vinyl group for biomaterials, the polymer solution was injected into a body prior to forming the crosslinkings by UV irradiation, which may be harmful to the body and actually causes difficulties in clinical application. In order to address such a problem, the present inventors checked whether the crosslinkings could occur when the polymer solution was UV-irradiated before being injected into a body. (See, FIG. 4)

Figure 4:
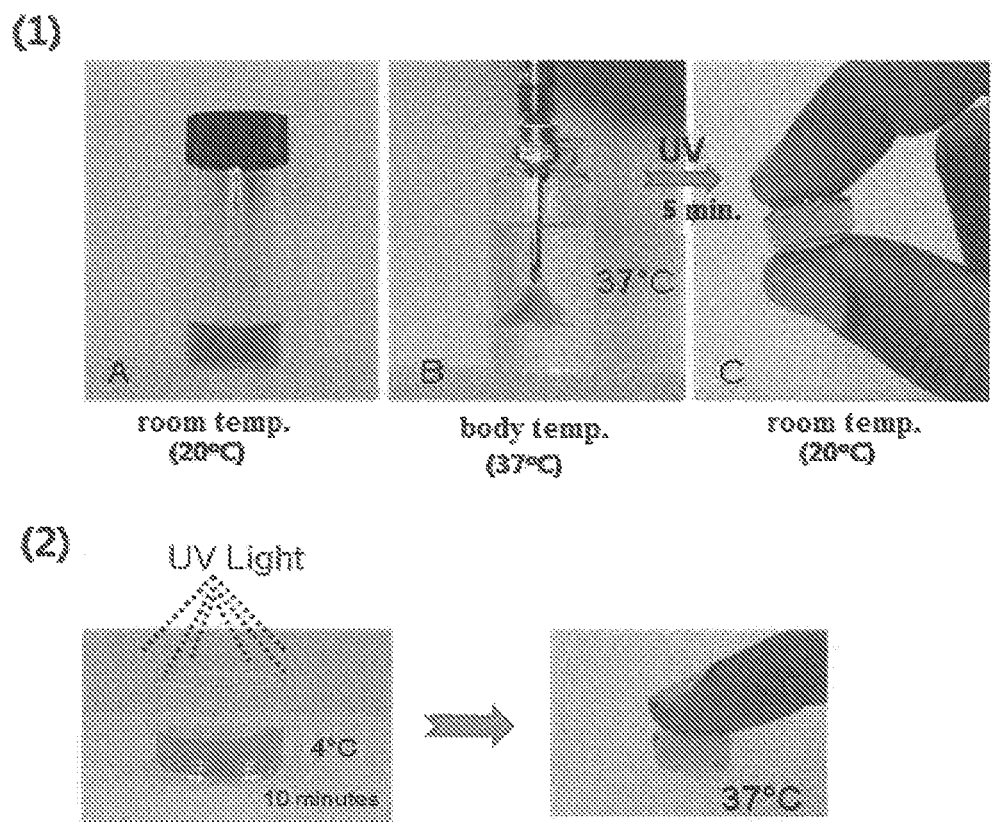
FIG. 4 is a photograph showing that according to an embodiment of the present invention, the hydrogels were formed by the crosslinkings both when a solution comprising a poly(organophosphazene) having a methacrylate substituent and a photoinitiator was gelled at a body temperature and then UV-irradiated, and when a solution comprising a poly(organophosphazene) having a methacrylate substituent and a photoinitiator was UV-irradiated at a low temperature and then gelled at a body temperature.

First, in accordance with a conventional method, the present inventor checked whether chemical crosslinkings occurred when the polymer solution was subjected to a physical gelation at 37° C. and then to UV-irradiation (See, FIG. 4(1)). As shown in FIG. 4(1), a solution prepared by mixing 0.01 wt % of a photoinitiator, Irgacure 2919 (Ciba Specialty Chemicals Inc.) with a phosphate buffered saline solution of 10 wt % of the poly(organophosphazene) of Example 1 having methacrylate substituents maintained its liquid phase at 4° C. but turned into a hydrogel at 37° C. Also, when it was irradiated with UV radiation of 365 nm for 5 minutes at 37° C., the gel did not flow and maintained its phase even at a low temperature, verifying the formation of crosslinkings.

Then, the present inventor checked whether the crosslinkings could occur when the polymer was irradiated by UV and then kept at 37° C. (See: FIG. 4(2)). As shown in FIG. 4(2), when a solution prepared by mixing 0.02 wt % of a photoinitiator, Irgacure 2919 (Ciba Specialty Chemicals Inc.) with a phosphate buffered saline solution of 10 wt % of the poly (organophosphazene) of Example 1 was irradiated by UV (356 nm) for 10 minutes, it maintained its liquid phase at 4° C. but developed a hydrogel by chemical crosslinkings as being heated to 37° C.

As such, the present method overcomes the underlying problems of the conventional method for crosslinking the polymers having a vinyl group, and so far there is no precedent for this crosslinking method and it is expected to present high applicability in actual clinical tests.

Example 42

Preparation of the Crosslinked Hydrogel of the Poly(Organophosphazene) Using a Thiol-Based Crosslinker and the Poly(Organophosphazene) Having a Vinyl Substituent To a Phosphate Buffered Saline Solution of 10 Wt % of the poly(organophosphazene) of Example 8 was added PEG dithiol having the weight-average molecular weight of 3500 at concentration of 0.11 mol % based on the poly(organophosphazene) of Example 8 and stirred at 37° C. with 50 rpm, and then its gelation behavior was observed over time. The phosphate buffered saline solution of the poly(organophosphazene) of Example 8, which had not shown gelation behavior at 37° C., formed a gel at 37° C. after 12 hours.

Also, PEG dithiol having the weight-average molecular weight of 3500 was added at concentration of 0.07 mol % based on the poly(organophosphazene) of Example 5 to a phosphate buffered saline solution of 10 wt % of the poly (organophosphazene) of Example 5 showing gelation behavior at 37° C., and stirred at 37° C. with 50 rpm, and then its gel solidity was observed as the crosslinking time passed. As the crosslinking time became longer, the gel solidity gradually increased so that the viscosity was maintained at a low temperature. In addition, when the crosslinkings were formed much, the gel continued to be maintained even at a low temperature.

The foregoing shows that the solution of the crosslinkable poly(organophosphazene) not only exhibits sol-gel behavior by the chemical crosslinkings, but also the solution of the thermosensitive, crosslinkable poly(organophosphazene) forms a gel with increasing a temperature, after which the crosslinkings are generated in the gel to make it even more solid.

Example 43

Preparation of the Crosslinked Hydrogel of the Poly(Organophosphazene) Using a Vinyl-Based Crosslinker and the Poly(Organophosphazene) Having a Thiol Substituent Vinyl sulfonate-4-arm PEG was added at concentration of 0.12 mol % based on the poly(organophosphazene) of Example 15 to a phosphate buffered saline solution of 10 wt % of the poly(organophosphazene) of Example 15, and stirred at 37° C. with 50 rpm, and then their gelation behavior was observed as time passed. The phosphate buffered saline solution of the poly(organophosphazene) of Example 15, which had not shown gelation behavior at 37° C., formed a gel at 37° C. after 1 hours.

Also, vinyl sulfonate-4-arm PEG was added at concentration of 0.03 mol % based on the poly(organophosphazene) of Example 17 to a phosphate buffered saline solution of 10 wt % of the poly(organophosphazene) of Example 17 showing gelation behavior at 37° C., and stirred at 37° C. with 50 rpm, and then their gel solidity was observed as the crosslinking time passed. As the crosslinking time became longer, the gel solidity increased gradually so that the viscosity was maintained at a low temperature. In addition, when the crosslinkings were formed much, the gel continued to be maintained even at a low temperature.

Example 44

Preparation of the Crosslinked Hydrogel of the Poly(Organophosphazene) Using an Enzyme and the Poly(Organophosphazene) Having a Tyramine Substituent Horseradish peroxidase was added at concentration of 0.58 wt % based on the poly(organophosphazene) of Example 24 to a phosphate buffered saline solution of 10 wt % of the poly(organophosphazene) of Example 24 showing gelation behavior at 37° C., and stirred at 37° C. with 50 rpm, and then their gel solidity was observed as the crosslinking time passed. As the crosslinking time became longer, the gel solidity increased gradually so that the viscosity was maintained at a low temperature. In addition, when the crosslinkings were formed much, the gel continued to be maintained even at a low temperature.

Example 45

Preparation of the Crosslinked Hydrogel of the Poly(Organophosphazene) Using an Enzyme and the Poly(Organophosphazene) Having a Tyrosine Substituent Horseradish peroxidase was added at concentration of 0.58 wt % based on the poly(organophosphazene) of Example 26 to a phosphate buffered saline solution of 10 wt % of the poly(organophosphazene) of Example 26 showing gelation behavior at 37° C., and stirred at 37° C. with 50 rpm, and then their gel solidity was observed as the crosslinking time passed. As the crosslinking time became longer, the gel solidity gradually increased so that the viscosity was maintained at a low temperature. Also, when the crosslinkings were formed much, the gel continued to be maintained even at a low temperature.

Example 46

Preparation of the Crosslinked Hydrogel of the Poly(Organophosphazene) Using the poly(organophosphazene) Having a Thiol Substituent and the Poly(Organophosphazene) Having an Acrylate Substituent Chemical crosslinkings between the poly(organophosphazene) having a thiol substituent and the poly(organophosphazene) having an acrylate substituent are advantageous in that they require neither UV irradiation nor a crosslinker, both of which can be potentially harmful to a human body.

In order to check the foregoing, the present inventors selected the polymer of Example 9 capable of being gelled at 37° C. and the polymer of Example 10 not being able to be gelled at 37° C. among the polymers with an acylate substituent and observed whether the chemical crosslinkings occurred when they were crosslinked with the polymer of Example 21 having a thiol substituent. The results are shown in FIG. 5.

Figure 5:
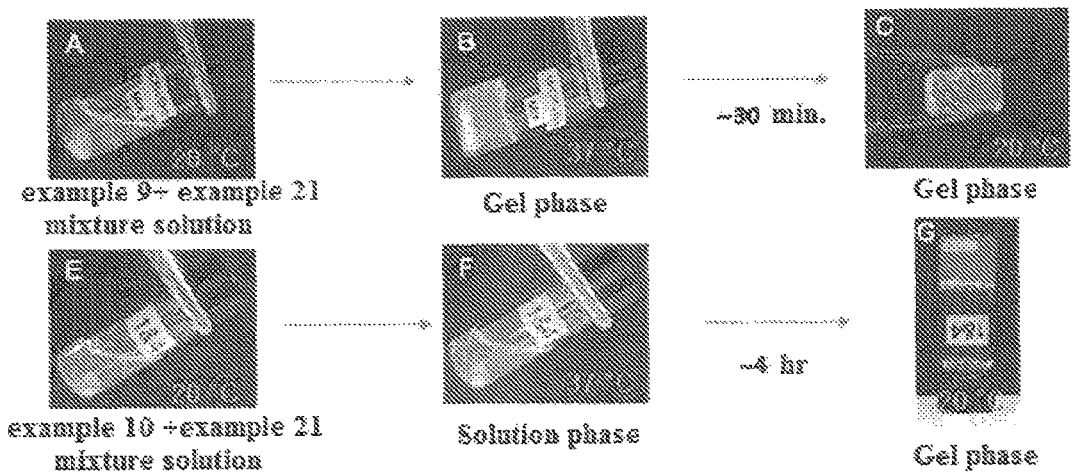
FIG. 5 is a photograph showing that according to an embodiment of the present invention, the hydrogel was formed by the crosslinkings when a solution of a poly(organophosphazene) having an acrylate substituent is mixed with a solution of a poly(organophosphazene) having a thiol substituent.

As shown in FIG. 5, when a phosphate buffered saline solution of 10 wt % of the poly(organophosphazene) of Example 9 showing gelation behavior at 37° C. was mixed with an equal amount of a phosphate buffered saline solution of 10 wt % of the poly(organophosphazene) of Example 21 showing gelation behavior at 37° C., the gel was formed at 37° C. Also, when the gel was kept at 37° C. for 30 minutes and then cooled to 20° C., it did not turn into a solution phase and maintained its gel phase, which indicates the formation of the chemical crosslinkings.

When a phosphate buffered saline solution of 10 wt % of the poly(organophosphazene) of Example 10 showing no gelation behavior at 37° C. was mixed with an equal amount of the phosphate buffered saline solution of 10 wt % of the poly(organophosphazene) of Example 21 showing gelation behavior, the gel was not formed at 37° C. However, after being kept for four hours at 37° C., they formed a gel, and when they cooled to 20° C., the gel did not turn into a solution phase, which indicates the formation of chemical crosslinkings.

Example 47

Figure 6:
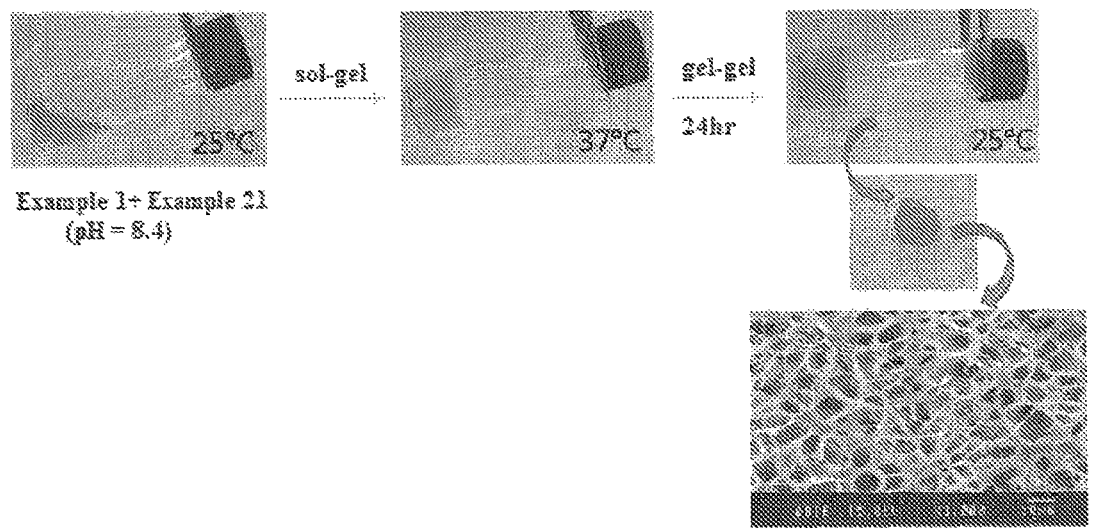
FIG. 6 is a photograph showing that according to an embodiment of the present invention, the hydrogel was formed by the crosslinkings when a solution of a poly(organophosphazene) having an acrylate substituent was mixed with a solution of a poly(organophosphazene) having a thiol substituent and then the pH of the resulting solution was adjusted to 8.4.

Preparation of the Crosslinked Hydrogel of the Phosphazene Polymer by Adding an Additive to the Phosphazene Polymer Having a Thiol Substituent and the Poly(Organophosphazene) Having a Methacrylate Substituent When a phosphate buffered saline solution of 10 wt % of the poly(organophosphazene) of Example 21 showing gelation behavior at 37° C. and having a thiol substituent was mixed at 4° C. with a phosphate buffered saline solution of 10 wt % of the poly(organophosphazene) of Example 1 showing gelation behavior at 37° C. and having a methacylate substituent, and the pH of the resulting mixture was adjusted to 8.4 by using 0.1N NaOH, the gel was formed at 37° C. and after 24 hours, it was found that the chemically crosslinked hydrogel was formed. The results are shown in FIG. 6.

When a phosphate buffered saline solution of 10 wt % of the poly(organophosphazene) of Example 21 showing gelation behavior at 37° C. and having a thiol substituent was mixed at 4° C. with a phosphate buffered saline solution of 10 wt % of the poly(organophosphazene) of Example 1 showing gelation behavior at 37° C. and having a methacrylate substituent, the pH of the resulting mixture was adjusted to 8.74 by using 0.1N NaOH, and as a catalyst hydrogen peroxide was mixed therewith at a concentration of 0.001 wt % at 4° C., the hydrogel was formed at 37° C. and after 10 hours, it was determined that the chemically crosslinked hydrogel was formed.

Example 48

Figure 7:
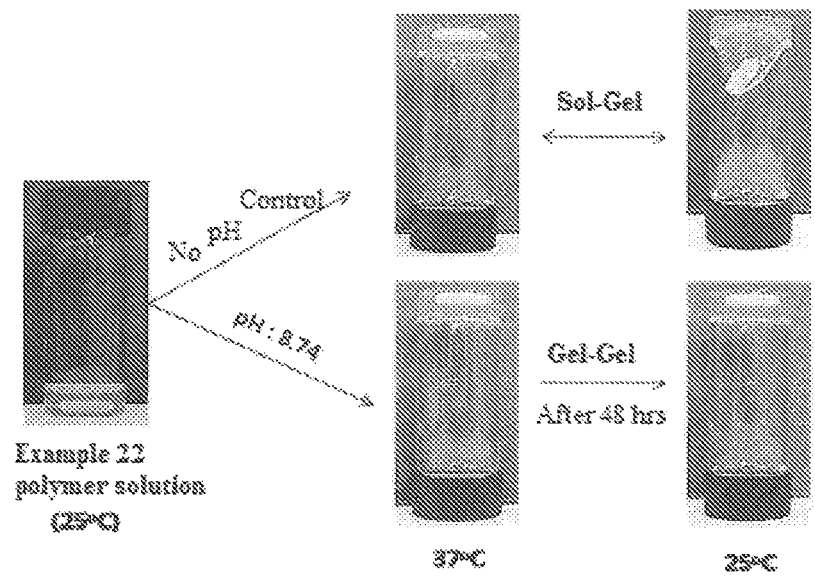
FIG. 7 is a photograph showing that according to an embodiment of the present invention, the hydrogel was formed by the crosslinking when the pH of a solution of the poly(organophosphazene) having a thiol substituent was adjusted to 8.74.

Preparation of the Crosslinked Hydrogel of the Poly(Organophosphazene) by Adding an Additive to the Poly(Organophosphazene) Having a Thiol Substituent When the pH of a phosphate buffered saline solution of 10 wt % of the poly(organophosphazene) of Example 22 showing gelation behavior at 37° C. and having a thiol substituent was adjusted to 8.74 by using 0.1N NaOH, the gel was formed at 37° C. and after 48 hours, the formation of the chemically crosslinked hydrogel was verified. The results are shown in FIG. 7.

Example 49

Determination of the Swelling Ratio for the Crosslinked Hydrogel Depending on the UV Exposure Time After placing 100 mg of a phosphate buffered saline solution of 10 wt % of the poly(organophosphazene) of Example 4 comprising 1 wt % of a photoinitiator, 2,2-diphenyl-1-pycrylhydrazyl onto a slide glass and then forming a hydrogel at 37° C., it was exposed to UV radiation of 365 nm for 1-5 minutes to prepare a crosslinked hydrogel of the poly(organophosphazene). The slide glass with the hydrogel formed thereon was immersed in 40 ml of distilled water at 37° C. for 24 hours. Then, the water surrounding the hydrogel was carefully removed, and the higrogel was weighed in its swelled state. Then, the hydrogel was freeze-dried and it was weighed in its dried state. The swelling ratio for the hydrogel depending on the UV exposure time was calculated by the following equation:

$$\text{Swelling ratio} = \frac{\left(\begin{array}{c}\text{Weight of the swelled hydrogel} - \\ \text{Weight of the dried hydrogel}\end{array}\right)}{\text{Weight of the dried hydrogel}} \times 100$$

The following Table 3 showed the swelling ratio measured as above for the crosslinked hydrogels, each of which is different in the exposure time to UV radiation.

TABLE 3

Results for measuring the swelling ratio of the hydrogel depending on the UV exposure time

| | UV Exposure Time | | | | |
|---|---|---|---|---|---|
| | 1 min. | 2 min. | 3 min. | 4 min. | 5 min. |
| Swelling Ratio | 59.29% | 58.40% | 58.03% | 54.32% | 51.71% |

Table 3 shows that as the UV exposure time increases, the swelling ratio decreases. Such a decrease in the swelling ratio indicates that the longer the UV exposure time is, the more the crosslinkings by acrylate groups occur in the hydrogel, producing a denser network structure.

Example 50

Determination of the Pore Sizes of the Crosslinked Hydrogel of the Poly(Organophosphazene)

The poly(organophosphazene)s of Examples 2 to 5 are different in their content of crosslinkable aminoethyl methacrylate, being 0.23, 0.21, 0.15, 0.14 mol %, respectively. With the method as described in Example 49, a phosphate buffered saline solution of 10 wt % of the poly(organophosphazene) prepared in each of Example 2 to 5 was exposed to UV radiation of 365 nm for 5 minutes to prepare a crosslinked hydrogel of the poly(organophosphazene), and after the hydrogel was freeze-dried, its pore size was determined using a scanning electron microscope.

Figure 8:
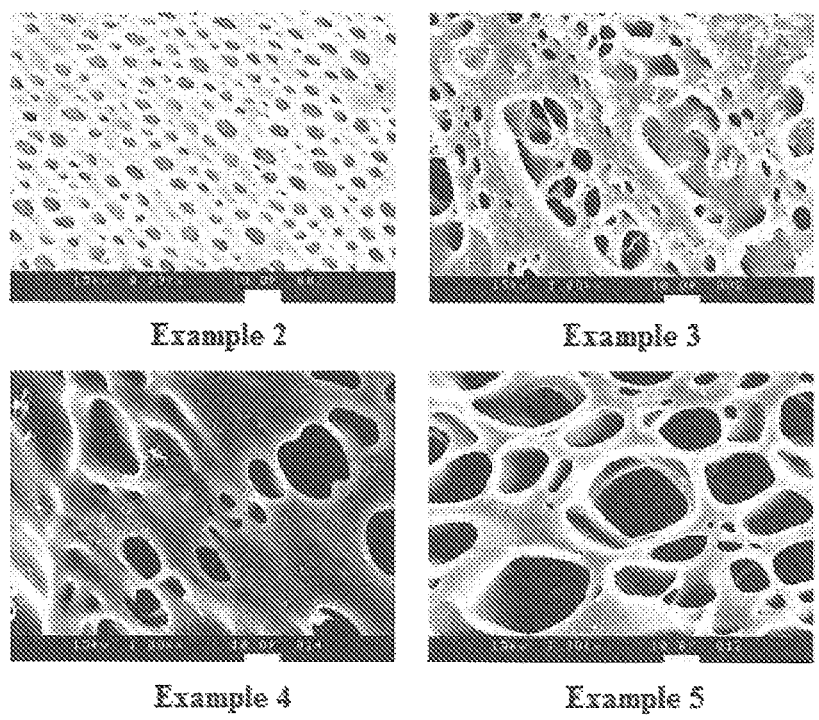
FIG. 8 is a photograph showing that according to an embodiment of the present invention, the pore sizes in the hydrogel varied with the crosslinking degree of the poly(organophosphazene) hydrogel comprising the crosslinkings.

The pore sizes of the crosslinked hydrogel of the poly(organophosphazene) as determined by the above method were shown in FIG. 8. As shown in FIG. 8, it can be found that as the content of crosslinkable aminoethyll methacrylate increases, the pore sizes in the hydrogel become smaller. In other words, an increase in the content of the crosslinkable aminoethyl methacrylate causes more crosslinkings to occur in the hydrogels so that the network structure in the hydrogel becomes denser and the pore sizes become smaller. As such, the pore size can be controlled according to a desired purpose so that if the hydrogel is to be utilized as a drug delivery system, it can present not only an enhanced ability to carry a small-sized drug but also a controlled release of the drug.

Example 51

Figure 9:
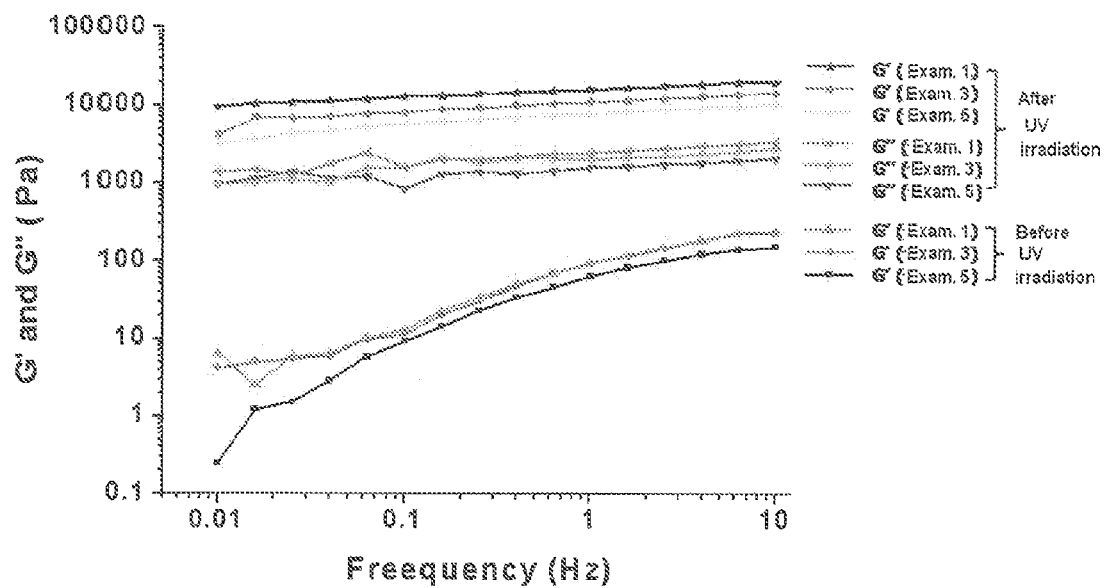
FIG. 9 is a graph illustrating the properties (G' and G") of the hydrogel according to an embodiment of the present invention prepared by crosslinking the solution comprising a photoinitiator and a poly(organophosphazene) having a methacrylate substituent and the properties of the hydrogel gelled only by a temperature without crosslinking, which illustrates that the properties of the crosslinked hydrogel has superior to the hydrogel prepared only by a temperature without crosslinking.

Rheological Characteristics of the Crosslinked Hydrogel by Using UV Radiation and the Poly(Organophosphazene)s Having a Methacrylate Substituent In this example, it was checked whether the chemically crosslinked hydrogels have more enhanced properties than the hydrogel gelled only by a temperature. Each of the polymers prepared in Examples 1, 3, and 5 was dissolved in a phosphate buffered saline solution at a concentration of 10 wt % and a photoinitiator, Irgacure 2919 was added thereto at a concentration 0.02 wt %. Then, after each of the solutions was subjected to a gelation at 37° C., the obtained hydrogel was irradiated by UV for five minutes, and then the properties thereof were measured using a rheometer (AR-2000 rheometer, TA Instruments). The results are shown in FIG. 9. As shown in FIG. 9, it was determined that after chemical crosslinkings, the polymers of all the Examples have G' values being 100 times higher than that of the hydrogel gelled only by a temperature, and thus they can be used as materials for plastic surgery including a filler, or tissue engineering materials including artificial joints or dental materials. (Biomaterials 2007; 28:2791800, G': the storage modulus, G": the loss modulus).

Example 52

Figure 10:
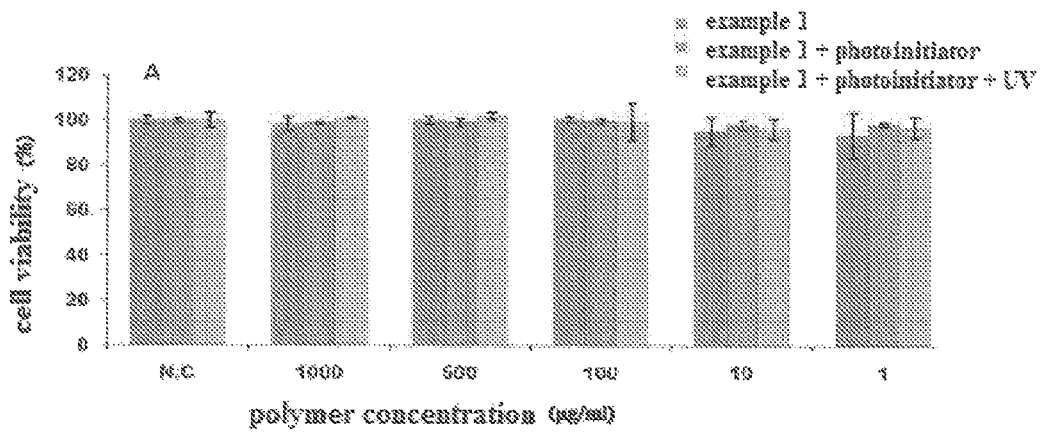
FIG. 10 is a graph showing cell viability when the cells were exposed in vitro to a solution of the poly(organophosphazene) with a methacrylate substituent according to an embodiment of the present invention at different concentrations, which illustrates that the polymer solution has no cytotoxicity regardless of the polymer concentration, the photoinitiator, and UV irradiation.

Test for Cytotoxicity of the Poly(Organophosphazene)s Having a Methacrylate Substituent In order to check whether the poly(organophosphazene) with a methacrylate substituent has cytotoxicity, the polymer of Example 1 was dissolved in a medium at a different concentration and carried out MTT test in vitro for NIH3T3 cells from Korean Cell Line Bank and the results were shown in FIG. 10. As shown in FIG. 10, the polymer having a methacrylate substituent shows such a high viability as the cell alone, regardless of the photoinitiator or UV irradiation, verifying its availability for biomaterials.

Example 53

Determination of the Gelation and Degradation Experiment in a Body for a Solution of the Poly(Organophosphazene) Having a Methacrylate Substituent The in vivo gelation and the rate of the in vivo degradation for the synthesized poly(organophosphazene)s with a methacrylate substituent were checked using a fluorescent image microscope and a scanning electron microscope (SEM).

First, each of the polymers of Examples 1 and 5 was bonded with fluoresceinamine (Sigma-Aldrich) and then dissolved in a phosphate buffered saline solution at a concentration of 10 wt % and mixed with a photoinitiator, Irgacure 2919 at a concentration of 0.02 wt %. The resulting solution was subcutaneously injected to a Balb/c nude mouse (Orient Bio) at 200 µl and then the injected site was irradiated by UV for five minutes to form crosslinkings. After that, in order to determine a degree of degradation, fluorescent images were obtained after a one-day lapse and a 60-day lapse from the injection, and then the gels were taken out from the laboratory animals and observed with a SEM. The results are shown in FIG. 11.

Figure 11:
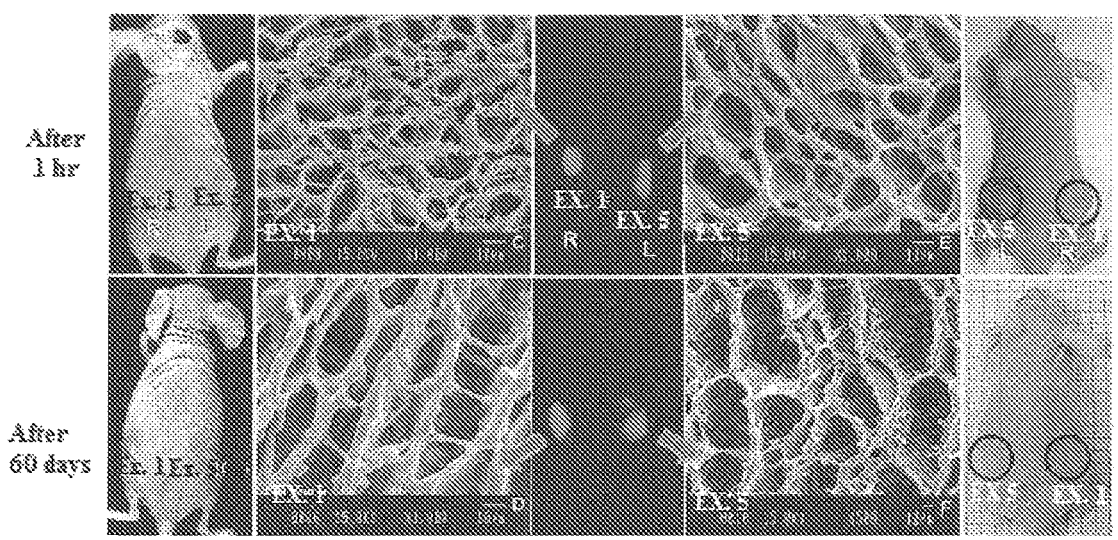
FIG. 11 is a photograph showing a condition of a mouse when it was subjected to a hypodermic injection with a solution of the poly(organophosphazene) with a methacrylate substituent according to an embodiment of the present invention, which illustrates that the hydrogel was formed in the body by the crosslinkings and maintained its phase in two months.

As shown in FIG. 11, it was determined that both of the polymer solutions formed a gel in a body, and the resulting hydrogels were maintained even after two months. Also, the observation by the SEM showed that the hydrogel after two months had a pore size larger than the hydrogel after one day and with increasing the content of the methacrylate, the hydrogel degraded more slowly.

Example 54

Rheological Characteristics of the Hydrogel Prepared by UV-Irradiating the Poly(Organophosphazene)s Having a Methacrylate Substituent at a Low Temperature and Crosslinking the Same at a Body Temperature In Example 49, it was determined that when the solution of the poly(organophosphazene) having a methacrylate substituent was gelled at a body temperature and then crosslinked by UV irradiation, the resulting hydrogel had far more enhanced properties than the hydrogel with no crosslinking. However, in the method of Example 49, the polymer solution was injected into a body and then irradiated by UV. Therefore, in this example, the solution of the poly(organophosphazene) having a methacrylate substituent was irradiated by UV at a low temperature (5° C.) and then crosslinked at a body temperature to check whether the resulting hydrogel has more enhanced properties than the hydrogel before the crosslinking. The results are shown in FIG. 12.

Figure 12:
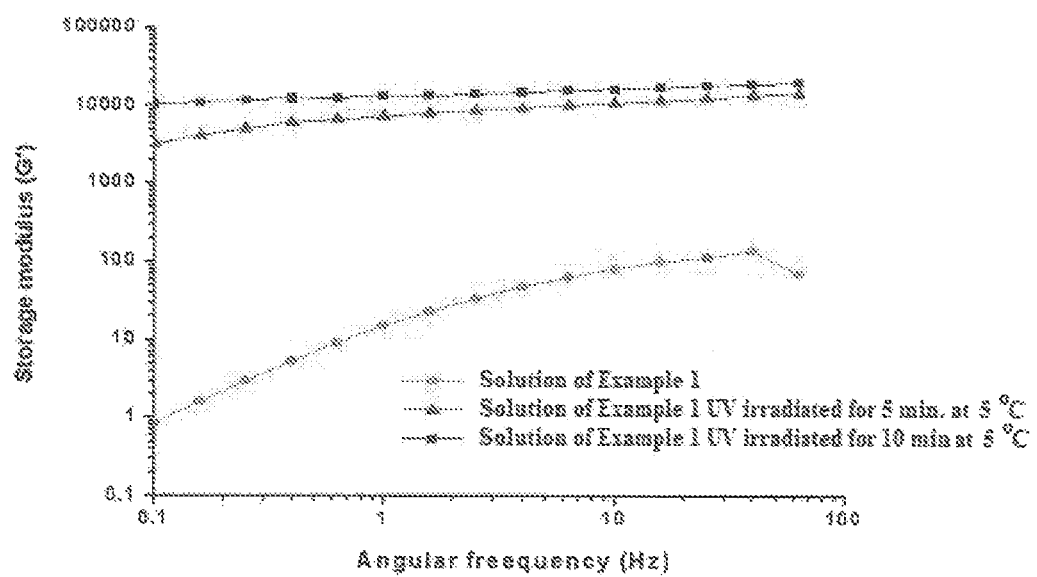
FIG. 12 is a graph showing the properties (G') of the hydrogel according an embodiment of the present invention prepared by UV-irradiating a solution comprising a photoinitiator and a poly(organophosphazene) with a methacrylate substituent and then crosslinking the same and the hydrogel gelled only by a temperature without crosslinking, which illustrates that the properties of the crosslinked hydrogel are superior to those of the hydrogel gelled only by temperature change without crosslinking.

As shown in FIG. 12, it was determined that the polymer irradiated by UV has G' values being 100 times higher than that of the polymers without UV irradiation. Also, it was confirmed that as the UV irradiation time increases, the hydrogel has a higher level of the solidity and thus it can be used as materials for plastic surgery including a filler, or tissue engineering materials including artificial joints or dental materials.

Example 55

Determination of the Gelation Behavior by Crosslinkings and Determination of Degradation of the Crosslinked Hydrogel Over Time when a Solution of the Poly(Organophosphazene) with a Methacrylate Substituent being UV-Irradiated at a Low Temperature and then being Injected into a Body In this example, a solution comprising a photoinitiator and a polymer with a methacrylate substituent was UV-irradiated at a low temperature and injected into a body to determine whether the crosslinkings were actually formed.

Figure 13:
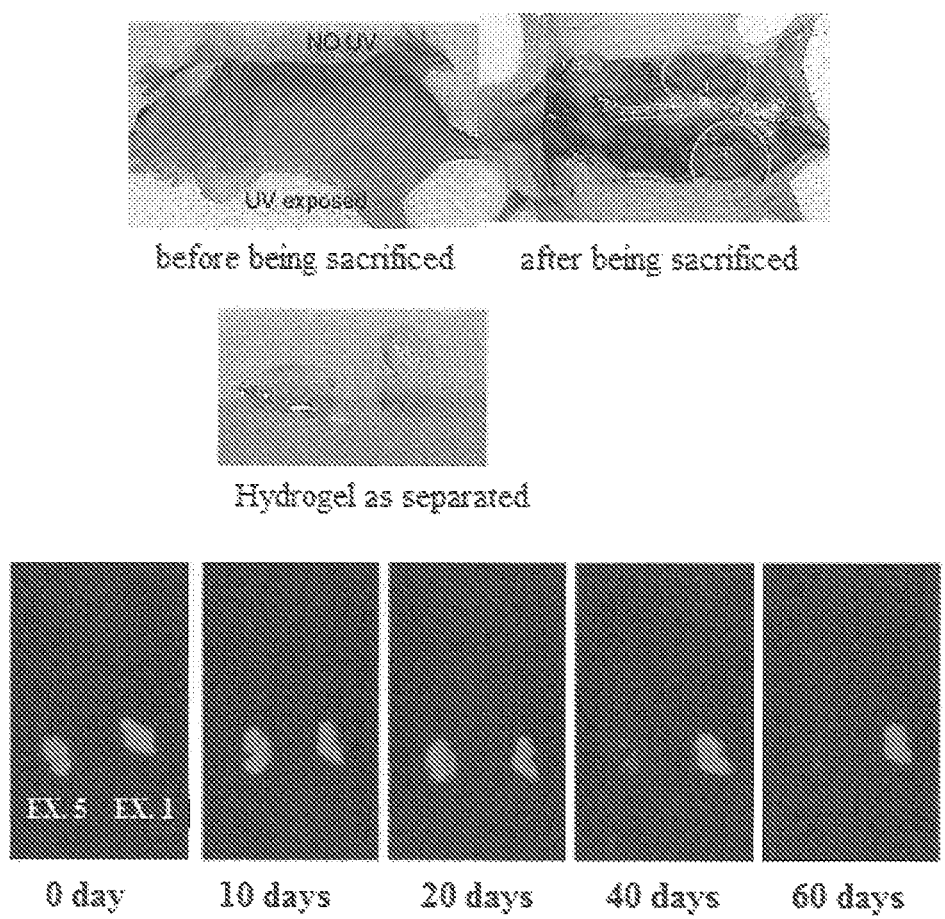
FIG. 13 is a photograph showing a condition of a Balb/c nude mouse when a solution comprising a photoinitiator and a poly(organophosphazene) having a methacrylate substituent according to an embodiment of the present invention is UV-irradiated at a low temperature (5° C.) and then injected subcutaneously to the mouse, which illustrates that the hydrogel was formed by crosslinkings and maintained even after 60 days and that the in-vivo degradation rate of the hydrogel could be controlled by changing the amount of the methacrylate substituent in the polymer.

First, a phosphate buffered saline solution of 10 wt % of the polymer of Example 1 was mixed with a photoinitiator, Irgacure 2919 at a concentration of 0.02 wt % and divided into two solutions, i.e., the one irradiated by UV at a low temperature (5° C.) and the other not irradiated by UV. Each of the two solutions was injected subcutaneously into a Balb/c nude mouse and the condition of the mouse was observed. The results are shown in FIG. 13. As shown in FIG. 13, both of the hydrogel were gelled in the body. However, unlike the hydrogel with no UV-irradiation, the hydrogel irradiated by UV maintained its gel phase at room temperature when the gel was taken out after the mouse was sacrificed, which verified the formation of the crosslinkings.

The rate of in vivo degradation was determined using a fluorescent image, and the experiments proceeded separately for the polymer of Example 1 having a large amount of the methacrylate substituent and for the polymer of Example 5 having a small amount of the methacrylate substituent. First, each of the polymers of Examples 1 and 5 was bonded to the fluoresceinamine and then dissolved respectively in a phosphate buffered saline solution at a concentration of 10 wt % at a low temperature (5° C.), and mixed with a photoinitiator, Irgacure 2919 with a concentration of 0.02 wt %. Then, each of the resulting solutions was irradiated with UV, and then subcutaneously injected to a Balb/c nude mouse to observe its condition. The results are shown in FIG. 13. As shown in FIG. 13, it was determined that both of the two solutions were gelled in a body, and that the hydrogel of Example 1 with a larger amount of the methacrylate substituent was crosslinked more and thus degraded more slowly than the hydrogel of Example 5 with a smaller amount of the methacrylate substituent and it maintained its hydrogel phase even after two months.

Example 56

Figure 14:
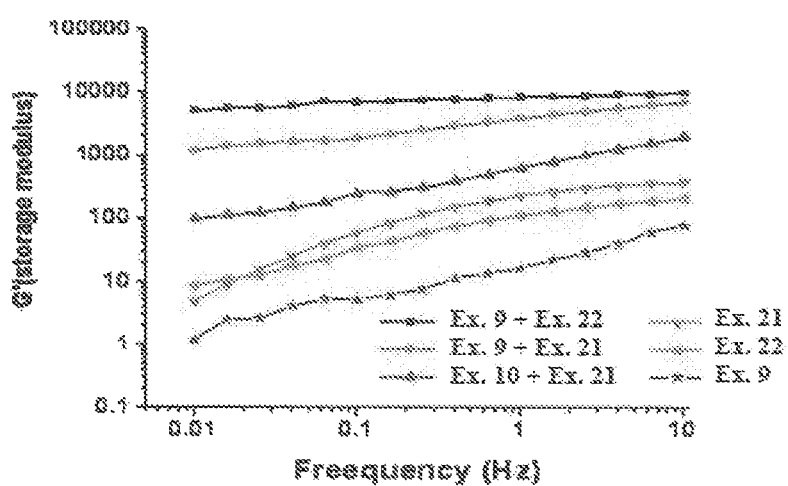
FIG. 14 is a graph showing the property (G') of the hydrogel according to the present invention prepared by mixing a solution of a poly(organophosphazene) having an acrylate substituent with the same amount of a solution of a poly (organophosphazene) having a thiol substituent and then crosslinking the same and the property (G') of a hydrogel gelled only by a temperature without crosslinking, which illustrates that the properties of the crosslinked hydrogel are superior to those of the hydrogel gelled only by temperature without crosslinking.

Rheological Characteristics of the Hydrogel Crosslinked by Mixing the Poly(Organophosphazene)s Having a Thiol Substituent with the Poly(Organophosphazene) Having an Acrylate Substituent In order to check whether the chemically crosslinked hydrogels have more enhanced properties than the hydrogel gelled only by a temperature, a mixture of the polymer solutions of Example 9 and Example 21, a mixture of the polymer solutions of Example 9 and Example 22, and a mixture of the polymer solutions of Example 10 and Example 21 were prepared and crosslinked, respectively, and then their properties were measured using a rheometer. The results are shown in FIG. 14. As shown in FIG. 14, it was determined that after a chemical crosslinking, the polymers of all the Examples have G' values being 100 times higher than that of the hydrogel gelled only by a temperature and thus they can be used as materials for plastic surgery including a filler, or tissue engineering materials including artificial joints or dental materials.

Example 57

Figure 15:
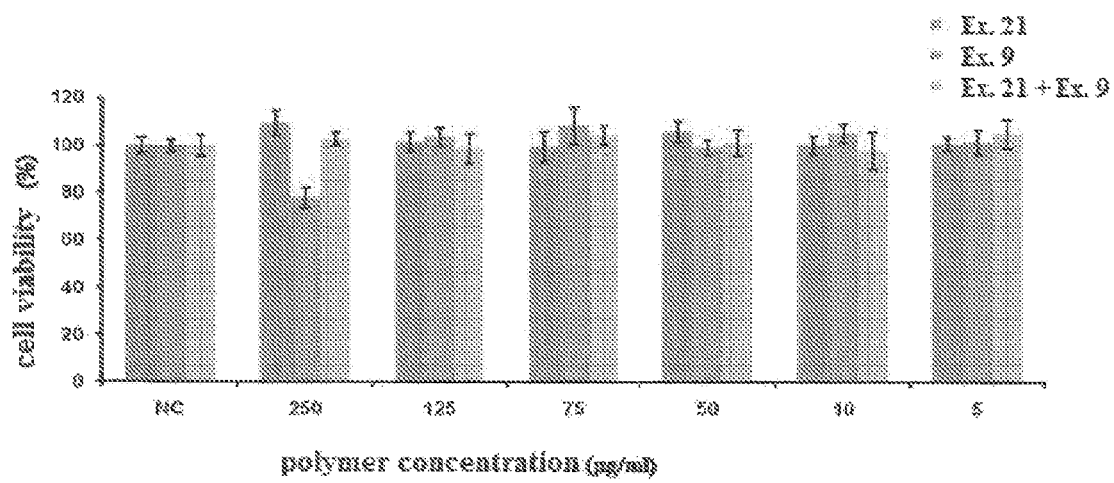
FIG. 15 is a graph showing cell viability when the cells are exposed in vitro to a solution of a poly(organophosphazene) having an acrylate substituent, a solution of a poly(organophosphazene) having a thiol substituent, and the mixture solution thereof according to an embodiment of the present invention at different concentrations, respectively, which illustrates that the polymer solution has no cytotoxicity regardless of the polymer concentration.

Test for Cytotoxicity of the Mixture of the Poly(Organophosphazene) Having a Thiol Substituent and the Poly(Organophosphazene) Having an Acrylate Substituent In order to check whether the mixture of the crosslinked hydrogels of the poly(organophosphazene) using the poly (organophosphazene) having a thiol substituent and the phosphazene polymer having an acrylate substituent have cytotoxicity, the polymers of Example 9 and Example 21 were dissolved in a medium at a different concentration and carried out MTT test in vitro for NIH3T3 cells and the results were shown in FIG. 15. As shown in FIG. 15, each of the two polymers and their mixture showed such a high viability as the cell alone, even at a high concentration, verifying its availability for biomaterials.

Example 58

Determination of In Vivo Gelation and In Vivo Degradation Experiment for a Mixture Solution of the Poly(Organophosphazene) Hydrogels Crosslinked by Using the Poly(Organophosphazene) Having a Thiol Substituent and the Poly(Organophosphazene) Having an Acrylate Substituent The in vivo gelation and the in vivo degradation rate for the crosslinked hydrogel of the poly(organophosphazene)s using the poly(organophosphazene) having a thiol substituent and the phosphazene polymer having an acrylate substituent were determined using a fluorescent image microscope.

Each of the polymers of Examples 9, 21, and 22 was bonded with fluoresceinamine and dissolved in a phosphate buffered saline solution at a concentration of 10 wt %. Then a mixture solution prepared by mixing a polymer solution of Example 9 with an equal amount of a polymer solution of Example 21 and the mixture solution prepared by mixing a polymer solution of Example 9 with an equal amount of a polymer solution of Example 22 were subcutaneously injected to a Balb/c nude mouse, respectively. The gel was taken out from the mouse after one day and after 60 days, respectively, and it was observed with a scanning electron microscope. The results are shown in FIG. 16.

Figure 16:
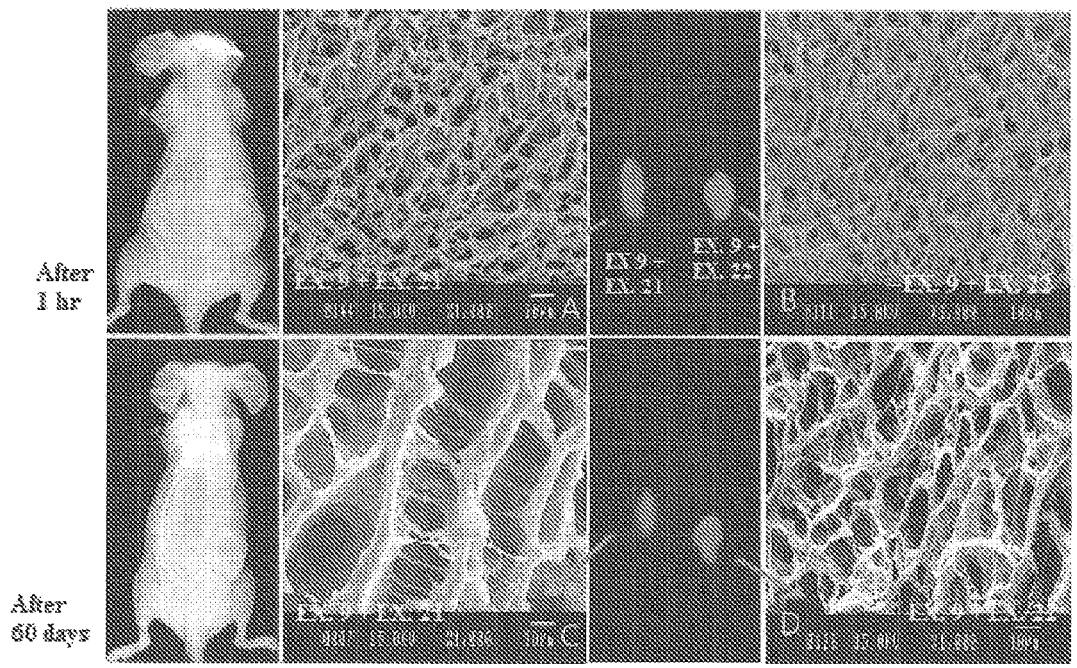
FIG. 16 is a photograph showing a condition of a mouse when a solution of a poly(organophosphazene) having an acrylate substituent and a solution of a poly(organophosphazene) having a thiol substituent are injected subcutaneously to the mouse in accordance with an embodiment of the present invention, which illustrates that the hydrogel was formed by crosslinkings in the body and maintained after 60 days.

As shown in FIG. 16, it was determined that both of the mixture solutions of the polymers formed a gel in a body and as the amount of the methacrylate substituent increased, the crosslinkings occurred more and thus the pore sizes became denser. Also, it was determined that after two months, the pore sizes of the hydrogel became larger due to degradation of the hydrogel and as the content of the methacrylate increased, the hydrogel degraded more slowly.

Example 59

Figure 17:
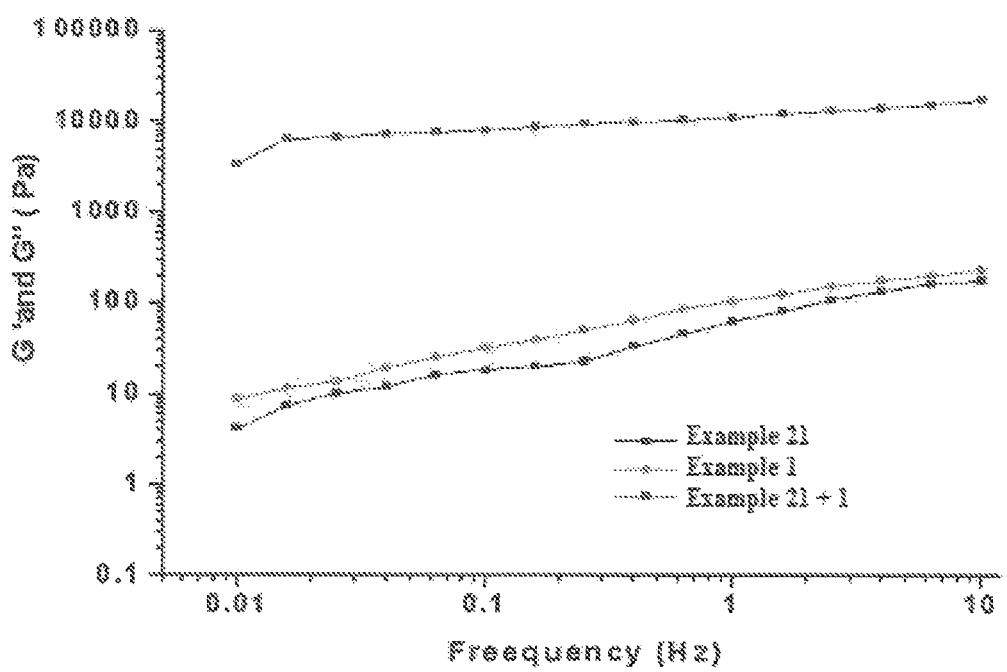
FIG. 17 is a graph showing the properties (G' and G'') of the hydrogel according to an embodiment of the present invention prepared by adjusting the pH of a solution of a poly (organophosphazene) having a thiol substituent to 8.74 and the hydrogel gelled only by a temperature without crosslinking, which illustrates that the properties of the crosslinked hydrogel are superior to those of the hydrogel gelled only by a temperature without crosslinking.

Rheological Characteristics of the Poly(Organophosphazene) Hydrogel Crosslinked by Mixing the Poly(Organophosphazene) Having a Thiol Substituent and the Poly(Organophosphazene) Having a Methacrylate Substituent In order to check whether the chemically crosslinked hydrogels have more enhanced properties than the hydrogel gelled only by a temperature, the polymer solution of Example 1 was mixed with an equal amount of the polymer solution of Example 21 and crosslinked by adjusting the pH of the mixture to 8.4 with 0.1N NaOH, and then their properties were measured using a rheometer. The results are shown in FIG. 17. As shown in FIG. 17, it was determined that after being chemically-crosslinked, the polymers of all the Examples have G' values being 100 times higher than that of the hydrogel gelled only by a temperature and thus they can be used as materials for plastic surgery including a filler, or tissue engineering materials including artificial joints or dental materials.

Example 60

Test for Cytotoxicity of the Poly(Organophosphazene) Having a Thiol Substituent

Figure 18:
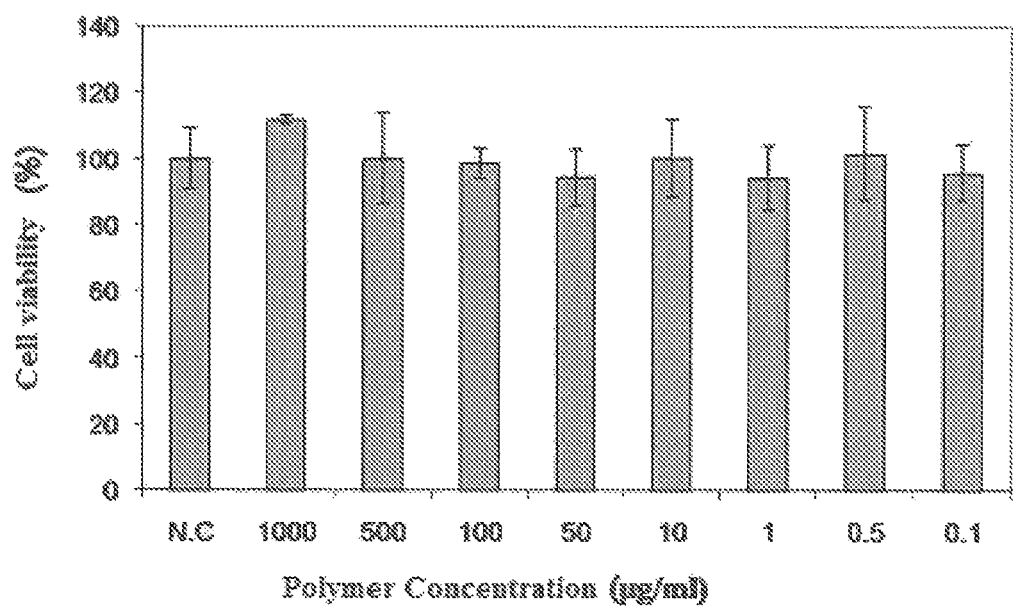
FIG. 18 is a graph showing cell viability when the cells are exposed in vitro to a solution of the poly(organophosphazene) with a thiol substituent in accordance with an embodiment of the present invention at different concentrations, which illustrates that the polymer solution has no cytotoxicity regardless of the polymer concentration.

In order to check whether the poly(organophosphazene) having a thiol substituent has cytotoxicity, the polymer of Example 22 was dissolved in a medium at a different concentration and carried out MTT test in vitro for NIH3T3 cells and the results were shown in FIG. 18. As shown in FIG. 18, the polymer having a thiol substituent showed such a high viability as the cell alone, even at a high concentration, verifying its availability for biomaterials.

Example 61

Experiment for the In Vivo Gelation Behavior for the Poly(Organophosphazene) Having a Thiol Substituent and a pH-Adjusting Additive In order to check whether a solution prepared by mixing the poly(organophosphazene) having a thiol substituent with a pH-adjusting additive formed a hydrogel by crosslinkings in a body, two types of experiments were conducted at a different pH.

The polymer of Example 22 was dissolved in a phosphate buffered saline at a concentration of 10% in each of two vials. After the pH of the solution in a first vial was adjusted to 8.75 with 0.1N NaOH solution and the pH of the solution in a second vial was adjusted to 6.8 with 0.1N HCl solution, each of the solutions in the first and the second vials was injected subcutaneously to a Balb/c nude mouse. In order to check whether the crosslinkings were formed, the mice were sacrificed in 48 hours and the gel was taken out therefrom and observed. The results are shown in FIG. 19.

Figure 19:
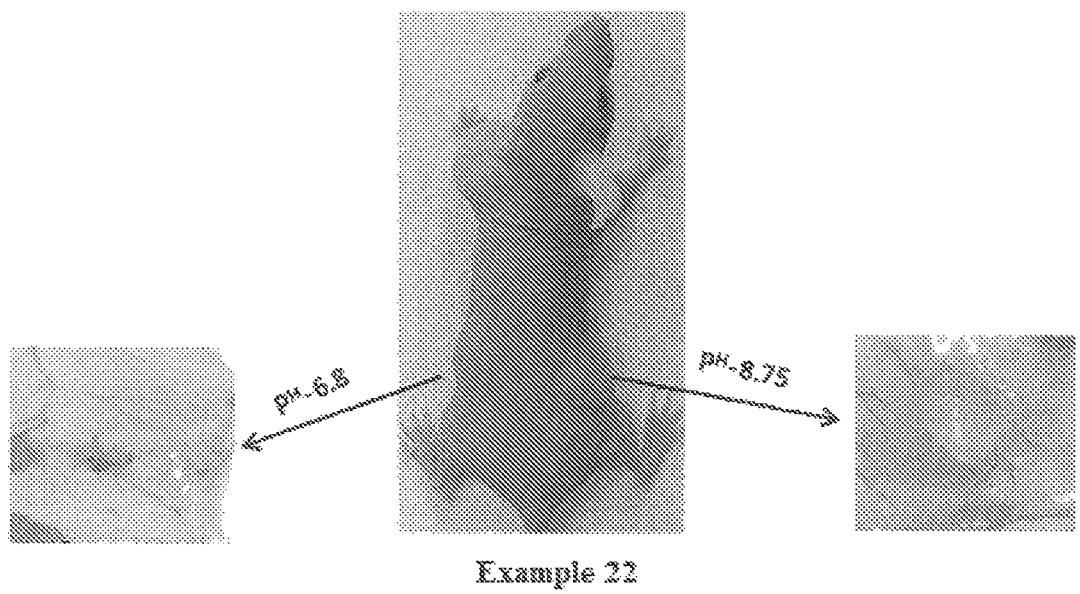
FIG. 19 is a photograph showing a condition of a mouse when according to an embodiment of the present invention, a solution of the poly(organophosphazene) with a thiol substituent is injected subcutaneously to the mouse, which illustrates that a hydrogel was formed by crosslinkings in the body as the solution was injected subcutaneously to the mouse after the pH of the solution had been adjusted to 8.75.

As shown in FIG. 19, the two mixed solution of the polymer formed a gel in a body. In case of the solution with a pH of 6.8, the gel was changed into a solution at room temperature, while in case of the solution with a pH of 8.75, the gel maintained its phase even at room temperature, which verified that chemical crosslinkings occurred at a pH of 8.75.

Example 62

Experiment for Degradation of the Hydrogel Crosslinked by Using a Vinyl Crosslinker and the Poly(Organophosphazene) Having a Thiol Substituent The biomaterials such as plastic surgery materials including a filler, tissue engineering materials including an artificial joint, and dental materials are required to have a high level of solidity and their degradation should proceed slowly over a long period of time. In order to check a long-period maintainability of the hydrogel formed by chemical crosslinkings, the hydrogel had been immersed in a phosphate buffered saline solution at 37° C. for one year and then its condition was compared with its original shape when being placed in the PBS.

Figure 20:
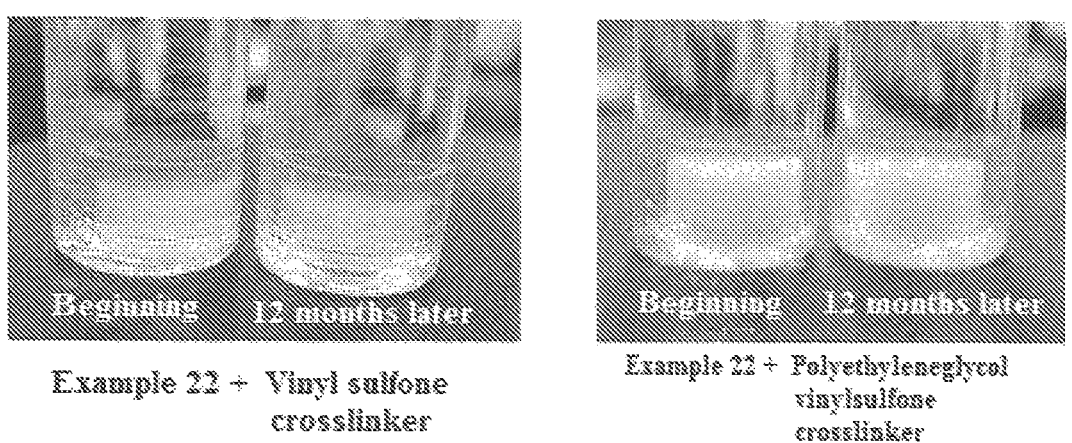
FIG. 20 is a photograph showing that the hydrogels according to an embodiment of the present invention maintained their shape even after one year when they had been crosslinked by mixing a solution of the poly(organophosphazene) having a thiol substituent with two types of vinyl crosslinkers, respectively and placed in a phosphate buffered saline solution at 37° C.

The polymer of Example 22 and two types of vinyl crosslinkers, i.e., vinyl sulfone and polyethylene glycol vinyl sulfone were used. To the phosphate buffered saline solution of 10 wt % of the poly(organophosphazene) of Example 22 was added and stirred vinyl sulfone or polyethyleneglycol vinyl sulfone at a concentration of 0.12 mol % based on the poly(organophosphazene) of Example 22, and then the resulting mixture was kept at 37° C. for 1 hour to form the crosslinkings. FIG. 20 shows the hydrogels that were crosslinked by two types of vinyl crosslinkers and then immersed in a phosphate buffered saline solution at 37° C. for one year. As shown in FIG. 20, it can be determined that the polymer of Example 22 was crosslinked by both types of the crosslinkers and the resulting hydrogels mostly maintained their original shape even after one year.

What is claimed is:

1. A poly(organophosphazene) with a physiologically active substance covalently-bonded thereto, which is chemically-crosslinkable and has Chemical Formula 1 as follows:

[Chemical Formula 1]

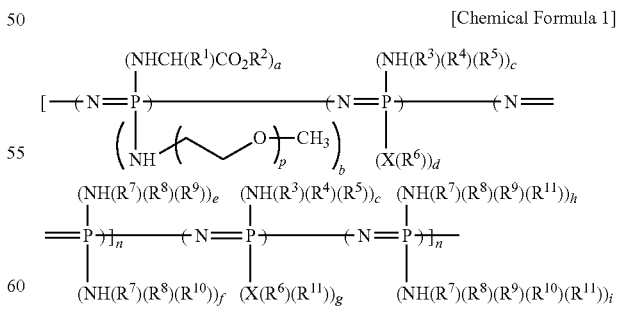

wherein,
p is from 7 to 50,
in $NHCH(R^1)CO_2R^2$, $R^1$ is selected from the group consisting of H, $CH_3$, $CH_2SH$, $CH_2OH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2H_2C_6H_4$, and $R^2$ is selected from the group consisting of $CH_3$, $C_2H_5$, $C_3H_7$, $C_4H_9$, $CH_2C_6H_5$ and $CH_2CHCH_2$ in $NH(R^3)(R^4)(R^5)$, $R^3$ is $CH(W)$, $R^4$ is selected from the group consisting of $CO_2$, $CONHCH(Q)CO_2CO_2$, $CH_2CO_2$ and $CO_2CH(CH_3)CO_2$, $R^5$ is selected from the group consisting of H, $CH_3$ and $C_2H_5$, in which each of W and Q is independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, in $XR^6$, X represents N or O, and $R^6$ is a compound that has a thiol group, a vinyl group, tyramine, tyrosine or a phenyl derivative, and is selected either from the group consisting of an acrylate compound, a methacrylate compound, an acrylamide compound, a vinyl sulfone compound, a thiol compound, a cysteine compound, a cisteamine compound, a mercaptic acid compound, an allyl pyrimidine compound and, a compound belonging to one of the foregoing compounds and having a thiol or vinyl group protected by a protecting group, or from the group consisting of a tyramine compound, a tyrosine compound, and a phenol derivative compound, $NH(R^7)(R^8)(R^9)$ represents a substituent having a functional group, in which $R^7$ is $CH(Y)$, $R^8$ is selected from the group consisting of $CH_2$, $C_2H_4$, $C_3H_6$, $C_4H_8$, $CH_2C_6H_4$, $CH_2CO_2$, $CH_2OCOCH_2CH_2CO$, $CH_2OCOCH_2CH_2CH_2CO$, $CH_2OCOCH_2CH_2CH_2CH_2CO$, $CH_2CH_2OCOCH_2CH_2CO$, $CH_2CH_2OCOCH_2CH_2CH_2CO$, $CH_2CH_2OCOCH_2CH_2CH_2CH_2CO$, O, $CONHCH(Z)O$, $CONHCH(Z)CONHCH(M)O$, $CONHCH(Z)CONHCH(N)CONHCH(L)O$, CO, $CO_2$, S, $CONHCH(Z)S$, $CONHCH(Z)CONHCH(M)S$, $CONHCH(Z)CONHCH(M)CONHCH(L)S$, N, $CONHCH(Z)N$, $CONHCH(Z)CONHCH(M)N$, $CONHCH(Z)CONHCH(M)CONHCH(L)N$, CON, $COCHNH(Z)CON$, $COCHNH(Z)CONHCH(M)CON$, $COCHNH(Z)CONHCH(M)CONHCH(L)CON$, $CONHCH(Z)CO$, $CONHCH(M)CO$, $CONHCH(Z)CONHCH(M)CO$, $CONHCH(L)CO$, $CONHCH(Z)CO_2$, $COCHNH(Z)CONHCH(M)CO_2$, $COCHNH(Z)CONHCH(M)CONHCH(L)CO_2$, $[OCH(CH_3)CO]_q$, $(OCH_2CO)_q$, $[(OCH(CH_3)CO]_q$, $[OCO(CH_2)_8CO]_q$, $[OCOC_6H_5O(CH_2)_3OC_6H_5CO]_q$ and $[OCOC_6H_6O(CH_2)_6OC_6H_6CO]_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_qH$, $[NHCH(C_4H_8NH_2)CO]_qOH$, $[NHCH[(CH_2)_3C(=NH)(NH_2)]CO]_qOH$, folic acid, hyaluronic acid, cyclodextrin, an imidazole compound, histidine, lysine, arginine, cysteine, thioalkyl amine, spermine, spermidine, TAT peptide, polyethyleneimine, polyhistidine, polylysine, polyarginine, heparin, chitosan, protamine, and a typical protecting group of a functional group, in which each of Y, Z, M, and L is independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$ and $CH_2SH$, and q represents the number of the repeating unit ranging from 1 to 18000, $R^{10}$ is a compound that has a thiol group, a vinyl group, tyramine, tyrosine or a phenyl derivative, and is selected either from the group consisting of an acrylate compound, a methacrylate compound, an acrylamide compound, a vinyl sulfone compound, a thiol compound, a cysteine compound, a cisteamine compound, a mercaptic acid compound, an allyl pyrimidine compound and, a compound belonging to one of the foregoing compounds and having a thiol or vinyl group protected by a protecting group, or from the group consisting of a tyramine compound, a tyrosine compound, and a phenyl derivative, $R^{11}$ represents a physiologically active substance and is at least one selected from the group consisting of a protein, a polypeptide, a peptide, a fusion protein, an antibody, a hormone, a vaccine, a gene, an anticancer drug, and an angiogenesis inhibitor that have at least one functional group selected from the group consisting of a hydroxyl, an amide, an amino, a carboxyl, a thiol, a vinyl, an aldehyde, a halogen, and a ketone groups, a, b, c, d, e, f, g, h, and i represent a content of each substituent, in which a and b range from 0.01 to 1.9, respectively, c, d, e, f, g, h, and i range from 0 to 1.9, respectively, d and f cannot be simultaneously zero, and g, h, and i cannot be simultaneously zero, and a+b+c+d+e+f+g+h+i=2.0, and n represents a degree of polymerization of the poly(organophosphazene), ranging from 5 to 100000.

2. The poly(organophosphazene) with a physiologically active substance covalently-bonded thereto in accordance with claim 1, wherein the protein, the polypeptide, the peptide, the fusion protein, and the antibody are at least one selected from the group consisting of erythropoietin (EPO), interferon-α, interferon-β, interferon-γ, a growth hormone releasing factor, a nerve growth factor (NGF), Granulocyte-colony stimulating factor (G-CSF), granulocyte macrophage-colony stimulating factor (GM-CSF), macrophage-colony stimulating factor (M-CSF), a blood clotting factor, insulin, albumin, botulinum toxin, oxytocin, vasopressin, a fibroblast growth factor (FGF), a epidermal growth factor (EGF), a platelet-derived growth factor (PDGF), a keratinocyte growth factor, an insulin-like growth factor (IGF), a vascular endothelial growth factor (VEGF), a transforming growth factor-beta (TGF-β), a nerve growth factor, a brain-derived neurotrophic factor (BDNF), neurotrophin-3 (NT-3), neurotrophin-4/5, prolactin, luliberin, LHRH agonists, LHRH antagonists, glucagon, interleukin-2 (IL-2), interleukin-11 (IL-11), gastrin, tetragastrin, pentagastrin, urogastrone, secretin, enkephalins, endorphins, angiotensins, tumor necrosis factor (TNF), tumor necrosis factor related apoptosis inducing ligand (TRAIL), heparinase, bone morphogenic proteins (BMPs), a human atrial natriuretic peptide (hANP), a glucagon-like peptide (GLP-1), exnatide, calcitonin (human or salmon), teriparatide, coagulation factors, hirudin, anakinra, renin, bradykinin, bacitracins, polymyxins, colistins, tyrocidine, gramicidins, cyclosporins, neurotensin, tachykinin, neuropeptide Y (NPY), peptide YY (PYY), vasoactive intestinal polypeptide (VIP), pituitray adenylate cyclase-activating polypeptide (PACAP) and synthetic analogues thereof, Arg-Gly-Asp, collagens, fibronectin, laminin, vitronectin, proteoglycan, monoclonal antibodies, fusion proteins, β-glucocerebrosidase, lactase, alglucosidase-α, α-galactosidase A, lipase, amylase, protease, hyaluronidase, $_L$-asparaginase and cytokines, the hormone is at least one selected from the group consisting of growth hormones, somatotropins, luteinizing hormone releasing hormone (LHRH), somatostatin, thyrotropin releasing hormone (TRH), adrenocorticotropic hormone, follicle-stimulating hormone (FSH), human chorionic gonadotropin (HCG), lutropin-α, testosterone, estradiol, progesterones, prostaglandins, and their synthetic analogues, and modified or equivalent efficacy substances, the vaccine is at least one selected from the group consisting of a hepatitis vaccine, an HPV vaccine, and a lime disease vaccine, the gene is at least one selected from the group consisting of small interference RNA (sRNA), small hairpin RNA (shRNA), micro RNA (miRNA), aptamer, plasmid DNA, and antisense oligodeoxynucleotide (AS-ODN), the anticancer drug is at least one selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxypogexterone acetate, epirubicin, letrozole, pirarubicin, topotecan, altretamine, toremifene citrate, BCNU, taxotere, actinomycin D, anasterozole, belotecan, imatinib, floxuridine, gemcitabine, hydroxyurea, zoledronate, vincristine, flutamide, valrubicin, streptozocin, silibinin, polyethyleneglygol conjugated anticancer drug, and synthetic analogues thereof, and modified or equivalent efficacy substances, and the angiogenesis inhibitor is at least one selected from the group consisting of L-Valinamide, N-[(2S)-2-mercapto-1-oxo-4-(3,4,4-trimethyl-2,5-dioxo-1-imidazolidinyl) butyl]-L-leucyl-N, 3-dimethyl, clodronate, 6-deoxy-6-demethyl-4-dedimethylaminotetracycline (COL-3), doxycycline, marimastat, 2-methoxyestradiol, squalamine, thalidomide, (Chloracetyl)carbamic acid (3R,4S,5S,6R)-5-methoxy-4-[(2R,3R)-2-methyl-3-(3-methyl-2-butenyl)oxiranyl]-1-oxaspiro[2.5]oct-6-yl ester, combretastatin A4, soy isoflavone, enzastaurin, (RS)-3-(4-Amino-1-oxo 1,3-dihydro-2H-isoindol-2-yl) piperidine-2,6-dione, celecoxib, N-(4-bromo-2-fluorophenyl)-6-methoxy-7-[(1-methylpiperidin-4-yl) methoxy]quinazolin-4-amine, halofuginone hydrobromide, interferon-α, bevacizumab, AE-941 (Neovastat), interleukin-12, vascular endothelial growth factor-trap (VEFG-trap), cetuximab, rebimastat, matrix metalloproteinases (MMP) inhibitor, protein kinase C beta inhibitor, endostatin, vatalanib (PTK787/ZK 222584), sunitinib malate (SU11248), cilenqitide (EMD-121974), humanized monoclonal antibody MEDI-522, volociximab, integrin alpha-5-beta-1-antagonist (ATN-161), and their synthetic analogs, and modified or equivalent efficacy substances.

3. The poly(organophosphazene) in accordance with claim 1, wherein in the definition of $R^6$ and $R^{10}$, the acrylate compound is an acrylate; an acrylate having a C1 to C30, substituted or unsubstituted, linear or branched alkyl group unsubstituted or substituted with at least one selected from the group consisting of a halogen atom, a C1 to C12 alkoxy, an acryloyloxy, and an amino acid; an acrylate having an amino acid group; ethyleneglycol acrylate; or polyethyleneglycol acrylate having polyethyleneglycol of the weight-average molecular weight of 200 to 2,500, the methacrylate compound is a methacrylate; a methacrylate having a C1 to C30, substituted or unsubstituted, linear or branched alkyl group unsubstituted or substituted with at least one selected from the group consisting of a halogen atom, a C1 to C12 alkoxy, an acryloyloxy, and an amino acid; a methacrylate having an amino acid group; ethyleneglycol methacrylate; or polyethyleneglycol methacrylate having polyethyleneglycol of the weight-average molecular weight of 200 to 2,500, the acrylamide compound is an acryl amide; an acryl amide having a C1 to C30, substituted or unsubstituted, linear or branched alkyl group unsubstituted or substituted with at least one selected from the group consisting of a halogen atom, a C1 to C12 alkoxy, acryloyloxy, and an amino acid; an acryl amide having an amino acid group; ethyleneglycol acrylamide; or polyethyleneglycol amide having polyethyleneglycol of the weight-average molecular weight of 200 to 2,500, the vinyl sulfone compound is a vinyl sulfone, vinyl sulfone-ethyleneglycol, vinyl sulfone-polyethyleneglycol having polyethyleneglycol of the weight-average molecular weight of 200 to 2,500, a vinyl sulfone-alkylate having a C1 to C30 alkyl group, a vinyl sulfone-amino acid, or a vinyl sulfone-peptide, the thiol compound is thiol-polyethylene glycol having polyethylene glycol of the weight-average molecular weight of 200 to 2,500, or a thiol-alkylate having a C1 to C30 alkyl group, the cysteine compound is cysteine, N-acetyl-cysteine, or an N-acetyl-cysteine alkyl ester having a C1 to C30 alkyl group, the cisteamine compound is cisteamine, or N-acetyl-cisteamine, the mercaptic acid compound is 2-mercapto succinic acid, the allyl pyrimidine compound is 1-allyl-2-amino-pyridinium, or 1-allyl-6-amino-3-ethyl-5-nitrosouracil, the tyramine compound is tyramine, or 3-methoxy-tyramine, the tyrosine compound is tyrosine, or tyrosine methylester, or tyrosine ethylester, and the phenol compounds is 2-amino-4-phenylphenol, 2-amino-4-teriaryamylphenol, 2-amino-4-tert-butylphenol, 8-amino-2-naphthol, 5-amino-1-naphthol, 4-amino-1-naphthol, 3-amino-2-naphthol, 1-amino-2-naphthol, 4-amino 2,5 dimethylphenol, 5-amino-2-methoxyphenol, 5-amino-2-methylphenol, 4-amino-3-methylphenol, 4-amino-2-methylphenol, 2-amino-5-methylphenol, 2-amino-4-methylphenol, 2-amino-3-methylphenol, 2,4-diaminophenol, 2,3-diaminophenol, 4-aminophenol, 3-aminophenol, 2-aminophenol, 4-amino-3-nitrophenol, 4-amino-2-nitrophenol, 2-amino-5-nitrophenol, 2-amino-4-nitrophenol, 2-amino-4-fluorophenol, 4-amino-3-chlorophenol, 4-amino-2-chlorophenol, 3-amino-4-chlorophenol, 2-amino-5-chlorophenol, 2-amino-4-chlorophenol, 5-amino-2,4-dichlorophenol, 4-amino-3,6-dichlorophenol, 2-amino-4-chloro-6-nitrophenol, or 4-amino-2,6-dibromophenol.

* * * * *